United States Patent
Fukumura et al.

(10) Patent No.: US 11,279,765 B2
(45) Date of Patent: Mar. 22, 2022

(54) COMPOSITIONS AND METHODS TO IMPROVE ANTI-ANGIOGENIC THERAPY AND IMMUNOTHERAPY

(71) Applicant: The General Hospital Corporation, Boston, MA (US)

(72) Inventors: Dai Fukumura, Newton, MA (US); Keehoon Jung, Boston, MA (US); Rakesh K. Jain, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/628,941

(22) PCT Filed: Jul. 9, 2018

(86) PCT No.: PCT/US2018/041284
§ 371 (c)(1),
(2) Date: Jan. 6, 2020

(87) PCT Pub. No.: WO2019/014122
PCT Pub. Date: Jan. 17, 2019

(65) Prior Publication Data
US 2020/0216549 A1    Jul. 9, 2020

Related U.S. Application Data

(60) Provisional application No. 62/530,124, filed on Jul. 8, 2017.

(51) Int. Cl.
*A61K 47/69* (2017.01)
*A61P 35/00* (2006.01)
*A61K 9/51* (2006.01)
*A61K 31/713* (2006.01)
*C12N 15/113* (2010.01)
*C07K 16/28* (2006.01)
*A61K 47/62* (2017.01)
*C07K 16/24* (2006.01)
*A61K 9/00* (2006.01)
*A61K 39/00* (2006.01)

(52) U.S. Cl.
CPC ........ *C07K 16/2866* (2013.01); *A61K 9/5123* (2013.01); *A61K 31/713* (2013.01); *A61K 47/62* (2017.08); *A61K 47/6935* (2017.08); *A61P 35/00* (2018.01); *C07K 16/24* (2013.01); *C12N 15/1136* (2013.01); *A61K 9/0019* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2012/0141471 A1 | 6/2012 | Salvino et al. | |
| 2013/0123347 A1 | 5/2013 | Kokkoli et al. | |

FOREIGN PATENT DOCUMENTS

| | | |
|---|---|---|
| WO | WO 2001/060406 | 8/2001 |
| WO | WO 2015/128849 | 9/2015 |

OTHER PUBLICATIONS

Ali et al., "Inactivation of PI(3)K p110delta breaks regulatory T-cell-mediated immune tolerance to cancer," Nature, Jun. 2014, 510(7505):407-411.
Auffray et al., "Monitoring of blood vessels and tissues by a population of monocytes with patrolling behavior," Science, Aug. 3, 2007, 317:666-670.
Baumeister et al., "Coinhibitory Pathways in Immunotherapy for Cancer," Annu Rev Immunol., May 20, 2016, 34:539-573.
Bronte et al., "Recommendations for myeloid-derived suppressor cell nomenclature and characterization standards," Nature Communications, 2016, 7(12150):1-10.
Buchbinder et al., "Melanoma in 2015: Immune-checkpoint blockade—durable cancer control," Nat Rev Clin Oncol., Feb. 2013, 13(2):77-78.
Carlin et al., "Nr4a1-dependent Ly6C(low) monocytes monitor endothelial cells and orchestrate their disposal," Cell, Apr. 2013, 153:362-375.
Carmeliet et al., "Molecular mechanisms and clinical applications of angiogenesis," Nature, May 19, 2011, 473(7347):298-307.
Casazza et al., "Impeding macrophage entry into hypoxic tumor areas by Sema3A/Nrp1 signaling blockade inhibits angiogenesis and restores antitumor immunity," Cancer Cell, Dec. 9, 2013, 24:695-709.
Chen et al., "Rapid discovery of potent siRNA-containing lipid nanoparticles enabled by controlled microfluidic formulation," Journal of the American Chemical Society, 2012, 134(16):6948-6851.
Chen et al., "VEGF siRNA delivered by polycation liposome-encapsulated calcium phosphate nanoparticles for tumor angiogenesis inhibition in breast cancer," International Journal of Nanomedicine, Aug. 21, 2017, 12:6075-6088.
Chiu et al., "Hypoxia induces myeloid-derived suppressor cell recruitment to hepatocellular carcinoma through chemokine (C-C motif) ligand 26," Hepatology, 2016, 64(3):797-813.

(Continued)

*Primary Examiner* — Elly-Gerald Stoica
(74) *Attorney, Agent, or Firm* — Fish & Richardson P.C.

(57) ABSTRACT

Agents that inhibit CX3CL1 in endothelial cells to reduce or inhibit immunosuppression mechanisms that are co-opted by cancer cells to evade host immune system, and that reduce immunosuppression in context of therapies that target VEGF-dependent signaling, and methods of use thereof.

16 Claims, 26 Drawing Sheets

Specification includes a Sequence Listing.

(56) References Cited

OTHER PUBLICATIONS

Chung et al., "An interleukin-17-mediated paracrine network promotes tumor resistance to anti-angiogenic therapy," Nature Medicine, Sep. 2013, 19(9):1114-1123.
Chung et al., "Enhanced systemic anti-angiogenic siVEGF delivery using PEGylated oligo-d-arginine," Molecular Pharmaceutics, Jul. 13, 2017, 14(9):1-36.
Chung et al., "Secreted Gaussia luciferase as a biomarker for monitoring tumor progression and treatment response of systemic metastases," PloS One, Dec. 2009, 4(12):1-8.
Dahlman et al., "In vivo endothelial siRNA delivery using polymeric nanoparticles with low molecular weight," Nat Nanotachnol., Aug. 2014, 9(8):648-655.
Damuzzo et al., "Complexity and challenges in defining myeloid-derived suppressor cells," Cytometry Part B, Clinical Cytometry, 2015, 88:77-91.
D'Angelo et al., "Efficacy and Safety of Nivolumab Alone or in Combination With Ipilimumab in Patients With Mucosal Melanoma: A Pooled Analysis," Journal of Clinical Oncology, Jan. 10, 2017, 35(2):226-235.
Ferrara et al., "Ten years of anti-vascular endothelial growth factor therapy," Nature Reviews, Jun. 2016, 15(6): 385-403.
Finisguerra et al., "MET is required for the recruitment of anti-tumoural neutrophils," Nature, Jun. 18, 2015, 522(7556):349-353.
Fong et al., "Fractalkine and CX3CR1 mediate a novel mechanism of leukocyte capture, firm adhesion, and activation under physiologic flow," J Exp Med, 1998, 188(8):1413-1419.
Franklin et al., "The cellular and molecular origin of tumor-associated macrophages," Science, May 23, 2014, 344(6168):921-925.
Gabrilovich et al., "Coordinated regulation of myeloid cells by tumours," Nat Rev Immunol, Mar. 2012, 12(4):253-268.
Geissmann et al., "Blood monocytes consist of two principal subsets with distinct migratory properties," Immunity, Jul. 2003, 19:71-82.
Hada et al., "Optimization of a siRNA carrier modified with a pH-sensitive cationic lipid and a cyclic RGD peptide for efficiently targeting tumor endothelial cells," Pharmaceutics, 2015, 7:320-333.
Haile et al., "Identification of discrete tumor-induced myeloid-derived suppressor cell subpopulations with distinct T cell-suppressive activity," J Immunol, 2010, 185:203-210.
Hanahan et al., "Accessories to the crime: functions of cells recruited to the tumor microenvironment," Cancer Cell, Mar. 20, 2012, 21:309-322.
Hanna et al., "Patrolling monocytes control tumor metastasis to the lung," Science, Nov. 20, 2015, 350(6263):985-990.
Haskell et al., "Molecular uncoupling of fractalkine-mediated cell adhesion and signal transduction. Rapid flow arrest of CX3CR1-expressing cells is independent of G-protein activation," Journal of Biological Chemistry, Apr. 9, 1999, 274(15):10053-10058.
Highfill et al., "Disruption of CXCR2-mediated MDSC tumor trafficking enhances anti-PD1 efficacy," Sci Transl Med, May 2014, 6(237):1-14.
Hu et al., "Hypoxia-induced autophagy promotes tumor cell survival and adaptation to antiangiogenic treatment in glioblastoma," Cancer Research, Apr. 2012, 72(7):1773-1783.
Huang et al., "Vascular normalizing doses of antiangiogenic treatment reprogram the immunosuppressive tumor microenvironment and enhance immunotherapy," Proceedings of the National Academy of Sciences of the United States of America, Oct. 23, 2012, 109(43):17561-17566.
Jain et al., "Antiangiogenesis Strategies Revisited: From Starving Tumors to Alleviating Hypoxia," Cancer Cell, Nov. 10, 2014, 26(5):605-622.
Jung et al., "Analysis of fractalkine receptor CX(3)CR1 function by targeted deletion and green fluorescent protein reporter gene insertion," Molecular and Cellular Biology, Jun. 2000, 20(11):4106-4114.
Jung et al., "Endoscopic time-lapse imaging of immune cells in infarcted mouse hearts," Circulation Research, Mar. 15, 2013, 6(15):891-899.
Jung et al., "Ly6Clo Monocytes Drive Immunosuppression and Confer Resistance to Anti-VEGFR2 Cancer Therapy," Journal of Clinical Investigation, 127(8):3039-3051.
Katoh et al., "CXCR2-expressing myeloid-derived suppressor cells are essential to promote colitis-associated tumorigenesis," Cancer Cell, Nov. 2013, 24(5):631-644.
Khan et al., "Dendrimer-Inspired Nanomaterials for the in vivo delivery of siRNA to lung vasculature," Nano Lett., May 13, 2015, 15(5):3008-3016.
Kim et al., "Combination Therapy with Anti-PD-1, Anti-TIM-3, and Focal Radiation Results in Regression of Murine Gliomas," Clinical Cancer Research, 2017, 23:124-136.
Kim et al., "Eradication of metastatic mouse cancers resistant to immune checkpoint blockade by suppression of myeloid-derived cells," Proceedings of the National Academy of Sciences of the United States of America, Aug. 2014, 111(32):11774-9.
Kim et al., "In vivo structure/function and expression analysis of the CX3C chemokine fractalkine," Blood, Nov. 24, 2011, 118(22):157-167.
Kim et al., "In vivo wide-area cellular imaging by side-view endomicroscopy," Nat Methods, Apr. 2010, 7(4): 303-305.
Kim et al., "Vascular RhoJ is an effective and selective target for tumor angiogenesis and vascular disruption," Cancer Cell, Jan. 13, 2014, 25(1):102-117.
Kirkpatrick et al., "Video-rate resonant scanning multiphoton microscopy: An emerging technique for intravital imaging of the tumor microenvironment," IntraVital, 2012, 1(1):60-68.
Kowalski et al., "Anti-VCAM-1 and Anti-E-selectin SAINT-O-Somes for selective delivery of siRNA into inflammation-activated primary endothelial cells," Mol Pharm., Aug. 5, 2013, 10(8):3033-3044.
Kumar et al., "The Nature of Myeloid-Derived Suppressor Cells in the Tumor Microenvironment," Trends Immunol, 2016, 37(3):208-220.
Landsman et al., "CX3CR1 is required for monocyte homeostasis and atherogenesis by promoting cell survival.," Blood, 2009, 113:963-972.
Lee et al., "VEGF siRNA delivery by a cancer-specific cell-penetrating peptide," J. Microbiol. Biotechnol, 2018, 28(3):367-374.
Leus et al., "Effective siRNA delivery to inflamed primary vascular endothelial cells by anti-E-selectin and anti-VCAM-1 PEGylated SAINT-based lipoplexes," International Journal of Pharmaceutics, 2014, 459:40-50.
Milosevic et al., "Sorafenib Increases Tumor Hypoxia in Cervical Cancer Patients Treated With Radiation Therapy: Results of a Phase 1 Clinical Study," International Journal of Radiation Oncology, Biology, & Physics, 2016, 94(1):111-117.
Mitri et al., "Tumour-infiltrating Gr-1+ myeloid cells antagonize senescence in cancer," Nov. 2016, 515(7525):134-137.
Morari et al., "Fractalkine (CX3CL1) is involved in the early activation of hypothalamic inflammation in experimental obesity," Diabetes, Nov. 2014, 63:3770-3784.
Morimoto-Tomita et al., "Mouse colon carcinoma cells established for high incidence of experimental hepatic metastasis exhibit accelerated and anchorage-independent growth," Clinical & Experimental Metastasis, 2005, 22(6):513-521.
Nahrendorf et al., "The healing myocardium sequentially mobilizes two monocyte subsets with divergent and complementary functions," J Exp Med, 2007, 204(12):3037-3047.
Noy et al., "Tumor-associated macrophages: from mechanisms to therapy," Immunity, Jul. 17, 2014, 41(1):49-61.
Palmer et al., "In vivo optical molecular imaging and analysis in mice using dorsal window chamber models applied to hypoxia, vasculature and fluorescent reporters," Nat Protoc., Aug. 2011, 6(9):1355-1366.
Pardoll, "The blockade of immune checkpoints in cancer immunotherapy," Nat Rev Cancer, Apr. 2012, 12(4):252-264.

(56) References Cited

OTHER PUBLICATIONS

PCT International Preliminary Report on Patentability in International Appln. No. PCT/US2018/041284, dated Nov. 2, 2018, 6 pages.
PCT International Search Report and Written Opinion in International Appln. No. PCT/US2018/041284, dated Nov. 2, 2018, 9 pages.
Peranzoni et al., "Myeloid-derived suppressor cell heterogeneity and subset definition," Curr Opin Immunol, Apr. 2010, 22(2):238-244.
Pernot et al., "Colorectal cancer and immunity: what we know and perspectives," World Journal of Gastroenterology, Apr. 14, 2014, 20(14):3738-3750.
Qian et al., "CCL2 recruits inflammatory monocytes to facilitate breast-tumour metastasis," Nature, 2011, 475(7355):222-225.
Qin et al., "Generation of a new therapeutic peptide that depletes myeloid-derived suppressor cells in tumor-bearing mice," Nat Med, Jun. 2014, 20(6):676-681.
Rahbart et al., "Anti-VEGF therapy induces ECM remodeling and mechanical barriers to therapy in colorectal cancer liver metastases," Science Translational Medicine, Oct. 12, 2016, 8(360):1-25.
Ratcliff et al., "Agreement between Programmed Cell Death Ligand-1 Diagnostic Assays across Multiple Protein Expression Cut-Offs in Non-Small Cell Lung Cancer," Clinical Cancer Research, 2017, 23:3585-3591.
Ries et al., "Targeting tumor-associated macrophages with anti-CSF-1R antibody reveals a strategy for cancer therapy," Cancer Cell, Jun. 2014, 25(6):846-859.
Rigamonti et al., "Role of angiopoietin-2 in adaptive tumor resistance to VEGF signaling blockade," Cell Reports, Aug. 7, 2014, 8:696-706.
Ritsma et al., "Surgical implantation of an abdominal imaging window for intravital microscopy," Nat Protoc, Mar. 2013, 8(3):583-594.
Rivera et al., "Escape mechanisms from antiangiogenic therapy: an immune cell's perspective" Advances in Experimental Medicine and Biology, 2014, 772:83-99.
Rivera et al., "Intertwined regulation of angiogenesis and immunity by myeloid cells," Trends in Immunology, Apr. 2015, 36(4):240-249.
Rivera et al., "Intratumoral myeloid cells regulate responsiveness and resistance to antiangiogenic therapy," Cell Reports, Apr. 28, 2015, 11(4):577-591.
Saja et al., "Triglyceride-Rich Lipoproteins Modulate the Distribution and Extravasation of Ly6C/Grl(low) Monocytes," Cell Reports, Sep. 2015, 21(11):1802-1815.
Schiffelers et al., "Cancer siRNA therapy by tumor selective delivery with ligand-targeted sterically stabilized nanoparticle," Nucleic Acids Research, 2004, 32(19):1-10.
Schmid et al., "Myeloid cells in tumor inflammation," Vascular Cell, 2012, 4(14):1-7.
Shojaei et al., "Tumor refractoriness to anti-VEGF treatment is mediated by CD11b+Gr1+ myeloid cells," Nature Biotechnology, Aug. 2007, 25(8): 911-920.
Sithoy et al., "Anti-VEGF/VEGFR therapy for cancer: reassessing the target," Cancer Research, 2012, 72(8):1909-1914.
Stromnes et al., "Targeted depletion of an MDSC subset unmasks pancreatic ductal adenocarcinoma to adaptive immunity," Gut, Nov. 2014, 63(11):1769-1781.
Suzuki et al., "Inhibition of CX3CL1 (Fractalkine) Improves Experimental Autoimmune Myositis in &RAMice," Journal of Immunology, Nov. 15, 2005, 175(10):6987-6996.
Talmadge et al., "History of myeloid-derived suppressor cells," Nat Rev Cancer, Oct. 2013, 13(10):739-752.
Tannous et al., "Gaussia luciferase reporter assay for monitoring biological processes in culture and in vivo," Nature Protocols, 2009, 4(4):582-591.
Tong et al., "Vascular normalization by vascular endothelial growth factor receptor 2 blockade induces a pressure gradient across the vasculature and improves drug penetration in tumors," Cancer Research, Jun. 2004, 64:3731-3736.
Topalian et al., "Mechanism-driven biomarkers to guide immune checkpoint blockade in cancer therapy," Nat Rev Cancer, May 2016, 16(5):275-287.
Weis et al., "Tumor angiogenesis: molecular pathways and therapeutic targets," Nature Medicine, 2011, 17(11):1359-1371.
Willett et al., "Efficacy, safety, and biomarkers of neoadjuvant bevacizumab, radiation therapy, and fluorouracil in rectal cancer: a multidisciplinary phase II study," Journal of Clinical Oncology, Jun. 20, 2009, 27(18):3020-3026.
Xu et al., "Direct evidence that bevacizumab, an anti-VEGF antibody, up-regulates SDF1alpha, CXCR4, CXCL6, and neuropilin 1 in tumors from patients with rectal cancer," Cancer Research, Oct. 15, 2009, 69(20):7905-7910.
Yang et al., "Abrogation of TGF beta signaling in mammary carcinomas recruits Gr-1+CD1 1b+ myeloid cells that promote metastasis," Cancer Cell, Jan. 2008, 13(1):23-35.
Youn et al., "Subsets of myeloid-derived suppressor cells in tumor-bearing mice," J Immunol, 2008, 181:5791-5802.
Yousefi et al., "Anginex lipoplexes for delivery of anti-angiogenic siRNA," Int J Pharm, Sep. 10, 2014, 472:175-184.
Zhang et al., "Development and characterization of a reliable mouse model of colorectal cancer metastasis to the liver," Clinical & Experimental Metastasis, Oct. 2013, 30(7):903-918.

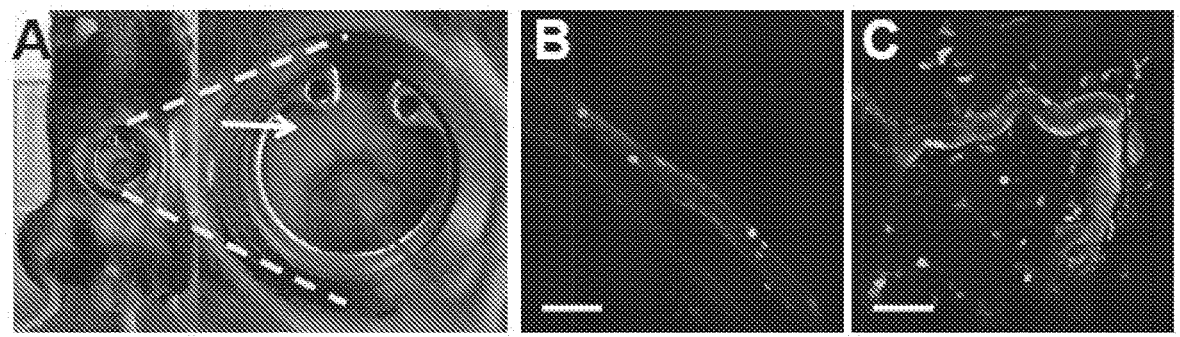
FIGs. 2A-2C
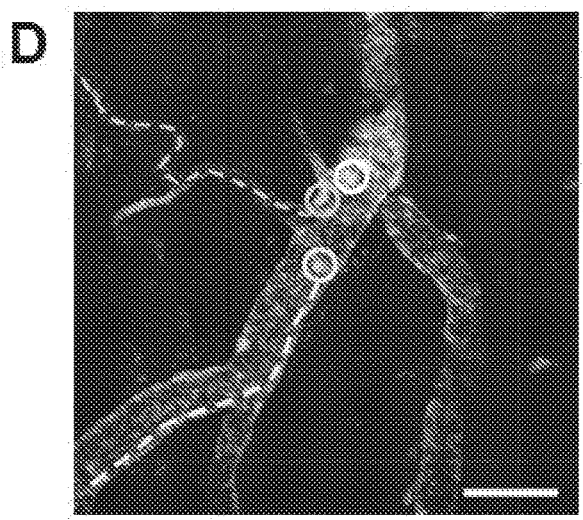 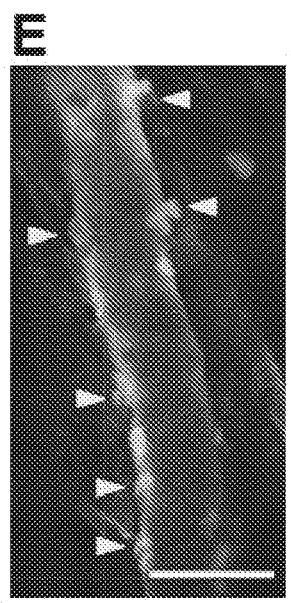
FIG. 2D  FIG. 2E

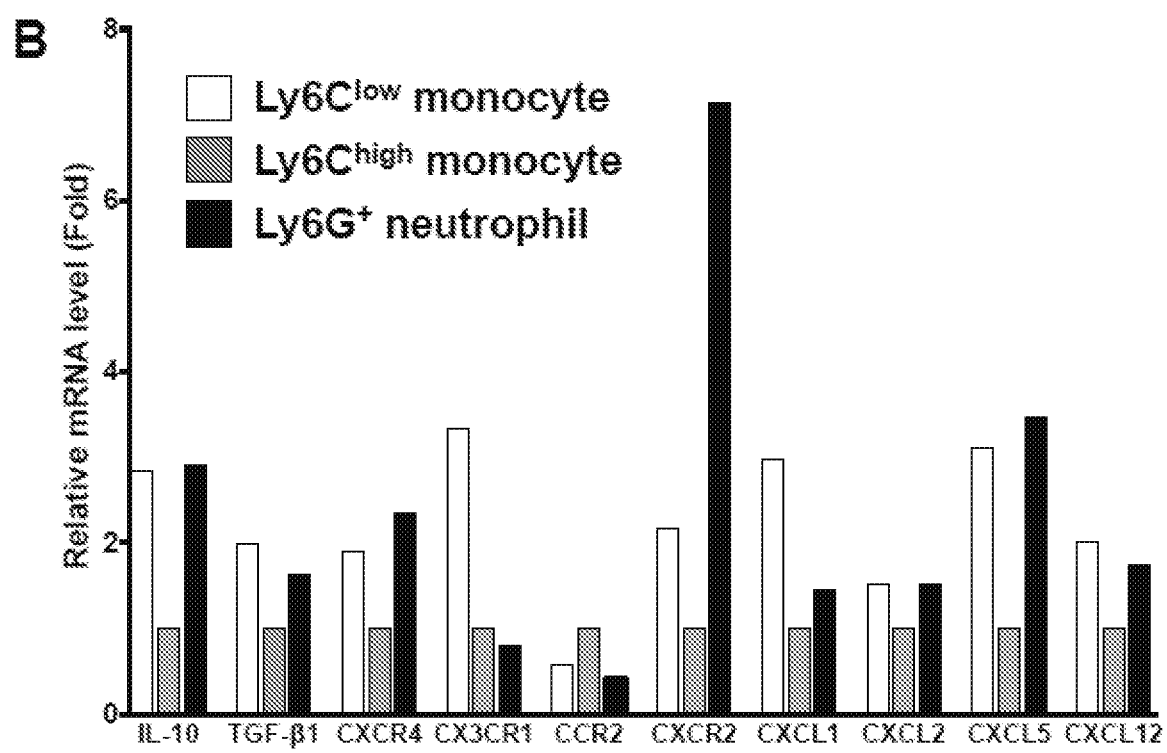
FIG. 10B
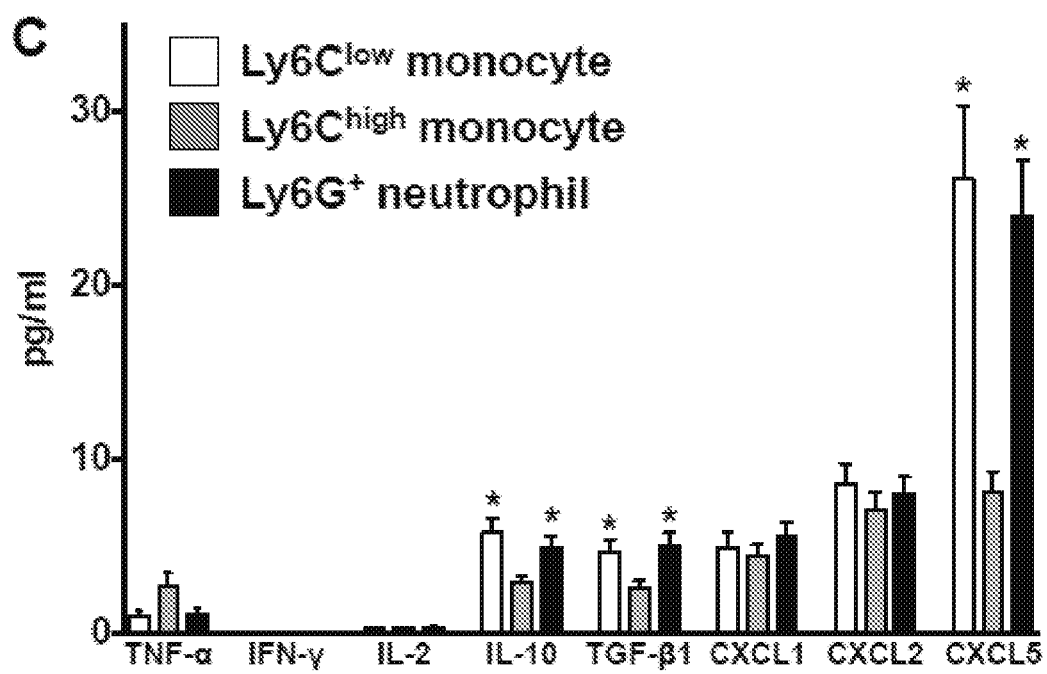

| D | Protein concentration (pg/mg) | |
|---|---|---|
| | Control | DC101 |
| TNF-α | 42.26 ± 2.80 | 15.70 ± 2.16 |
| IFN-γ | 4.13 ± 0.81 | 2.13 ± 0.49 |
| IL-2 | 4.52 ± 0.66 | 2.03 ± 0.26 |
| IL-10 | 6.60 ± 1.18 | 25.20 ± 3.81 |
| TGF-β1 | 204.07 ± 14.35 | 352.87 ± 34.01 |
| CXCL1 | 223.77 ± 42.73 | 263.53 ± 72.42 |
| CXCL2 | 230.05 ± 40.82 | 165.43 ± 37.38 |
| CXCL5 | 186.14 ± 32.39 | 391.18 ± 41.57 |
| CXCL12 | 79.329 ± 7.78 | 146.62 ± 20.78 |
| CX3CL1 | 52.70 ± 10.45 | 157.9 ± 18.67 |
| CCL2 | 55.32 ± 3.65 | 47.72 ± 7.28 |

FIG. 10D

SEQUENCE LISTING

<160> NUMBER OF SEQ ID NOS: 42

<210> SEQ ID NO 1
<211> LENGTH: 19
<212> TYPE: DNA
<213> ORGANISM: Artificial Sequence
<220> FEATURE:
<223> OTHER INFORMATION: Bv8 forward primer

<400> SEQUENCE: 1
gccccgctac tgctacttc                                           19

<210> SEQ ID NO 2
<211> LENGTH: 21
<212> TYPE: DNA
<213> ORGANISM: Artificial Sequence
<220> FEATURE:
<223> OTHER INFORMATION: Bv8 reverse primer

<400> SEQUENCE: 2
ccccgtgcag acactaactt t                                        21

<210> SEQ ID NO 3
<211> LENGTH: 22
<212> TYPE: DNA
<213> ORGANISM: Artificial Sequence
<220> FEATURE:
<223> OTHER INFORMATION: Tie2 forward primer

<400> SEQUENCE: 3
gagtcagctt gctcctttat gg                                       22

<210> SEQ ID NO 4
<211> LENGTH: 23
<212> TYPE: DNA
<213> ORGANISM: Artificial Sequence
<220> FEATURE:
<223> OTHER INFORMATION: Tie2 reverse primer

<400> SEQUENCE: 4
agacacaaga ggtagggaat tga                                      23

<210> SEQ ID NO 5
<211> LENGTH: 20
<212> TYPE: DNA

```
<213> ORGANISM: Artificial Sequence
<220> FEATURE:
<223> OTHER INFORMATION: Cx3cl1 forward primer

<400> SEQUENCE: 5
cgcgttcttc catttgtgta                                               20

<210> SEQ ID NO 6
<211> LENGTH: 20
<212> TYPE: DNA
<213> ORGANISM: Artificial Sequence
<220> FEATURE:
<223> OTHER INFORMATION: Cx3cl1 reverse primer

<400> SEQUENCE: 6
ctgtgtcgtc tccaggacaa                                               20

<210> SEQ ID NO 7
<211> LENGTH: 19
<212> TYPE: DNA
<213> ORGANISM: Artificial Sequence
<220> FEATURE:
<223> OTHER INFORMATION: CX3CL1 ssRNA sense

<400> SEQUENCE: 7
gcuugcgaga ggguuuaaa                                                19

<210> SEQ ID NO 8
<211> LENGTH: 19
<212> TYPE: DNA
<213> ORGANISM: Artificial Sequence
<220> FEATURE:
<223> OTHER INFORMATION: CX3CL1 ssRNA anti-sense

<400> SEQUENCE: 8
uuuaaacccu cucgcaagc                                                19

<210> SEQ ID NO 9
<211> LENGTH: 16
<212> TYPE: DNA
<213> ORGANISM: Artificial Sequence
<220> FEATURE:
<223> OTHER INFORMATION: siRNA against CX3CL1 sense

<400> SEQUENCE: 9
gccgcguucu uccauu                                                   16

<210> SEQ ID NO 10
<211> LENGTH: 16
<212> TYPE: DNA
<213> ORGANISM: Artificial Sequence
<220> FEATURE:
<223> OTHER INFORMATION: siRNA against CX3CL1 anti-sense

<400> SEQUENCE: 10
acaaauggaa gaacgc                                                   16

<210> SEQ ID NO 11
<211> LENGTH: 19
<212> TYPE: DNA
<213> ORGANISM: Artificial Sequence
<220> FEATURE:
<223> OTHER INFORMATION: siRNA against Tie2 sense

<400> SEQUENCE: 11
gaagaugcag ugauuuaca                                                19
```

```
<210> SEQ ID NO 12
<211> LENGTH: 19
<212> TYPE: DNA
<213> ORGANISM: Artificial Sequence
<220> FEATURE:
<223> OTHER INFORMATION: siRNA against Tie2 anti-sense

<400> SEQUENCE: 12
uguaaaucac ugcaucuuc                                                    19

<210> SEQ ID NO 13
<211> LENGTH: 19
<212> TYPE: DNA
<213> ORGANISM: Artificial Sequence
<220> FEATURE:
<223> OTHER INFORMATION: siRNA against Luciferase sense

<400> SEQUENCE: 13
cuuacgcuga guacuucga                                                    19

<210> SEQ ID NO 14
<211> LENGTH: 19
<212> TYPE: DNA
<213> ORGANISM: Artificial Sequence
<220> FEATURE:
<223> OTHER INFORMATION: siRNA against Luciferase anti-sense

<400> SEQUENCE: 14
ucgaaguacu cagcguaag                                                    19

<210> SEQ ID NO 15

<400> SEQUENCE: 15

000

<210> SEQ ID NO 16

<400> SEQUENCE: 16

000

<210> SEQ ID NO 17
<211> LENGTH: 19
<212> TYPE: DNA
<213> ORGANISM: Artificial Sequence
<220> FEATURE:
<223> OTHER INFORMATION: siRNA_0001 sense

<400> SEQUENCE: 17
ccgcgaguga cuacuagga                                                    19

<210> SEQ ID NO 18
<211> LENGTH: 19
<212> TYPE: DNA
<213> ORGANISM: Artificial Sequence
<220> FEATURE:
<223> OTHER INFORMATION: siRNA_0002 sense

<400> SEQUENCE: 18
ccuccuggcc cgccgaauu                                                    19

<210> SEQ ID NO 19
<211> LENGTH: 19
<212> TYPE: DNA
```

```
<213> ORGANISM: Artificial Sequence
<220> FEATURE:
<223> OTHER INFORMATION: siRNA_0003 sense

<400> SEQUENCE: 19
caccucggca ugacgaaau                                              19

<210> SEQ ID NO 20
<211> LENGTH: 19
<212> TYPE: DNA
<213> ORGANISM: Artificial Sequence
<220> FEATURE:
<223> OTHER INFORMATION: siRNA_0004 sense

<400> SEQUENCE: 20
ugcgaaauca ugugcgaca                                              19

<210> SEQ ID NO 21
<211> LENGTH: 19
<212> TYPE: DNA
<213> ORGANISM: Artificial Sequence
<220> FEATURE:
<223> OTHER INFORMATION: siRNA_0005 sense

<400> SEQUENCE: 21
guggcaguaa cucauacgu                                              19

<210> SEQ ID NO 22
<211> LENGTH: 19
<212> TYPE: DNA
<213> ORGANISM: Artificial Sequence
<220> FEATURE:
<223> OTHER INFORMATION: siRNA_0006 sense

<400> SEQUENCE: 22
gcuugcgaga ggguuuaaa                                              19

<210> SEQ ID NO 23
<211> LENGTH: 19
<212> TYPE: DNA
<213> ORGANISM: Artificial Sequence
<220> FEATURE:
<223> OTHER INFORMATION: siRNA_0007 sense

<400> SEQUENCE: 23
gcuugagagu gcagaucgu                                              19

<210> SEQ ID NO 24
<211> LENGTH: 19
<212> TYPE: DNA
<213> ORGANISM: Artificial Sequence
<220> FEATURE:
<223> OTHER INFORMATION: siRNA_0008 sense

<400> SEQUENCE: 24
ggccacaaac ccaauuuca                                              19

<210> SEQ ID NO 25
<211> LENGTH: 19
<212> TYPE: DNA
<213> ORGANISM: Artificial Sequence
<220> FEATURE:
<223> OTHER INFORMATION: siRNA_0009 sense

<400> SEQUENCE: 25
guacuugcau agucagaca                                              19
```

<210> SEQ ID NO 26
<211> LENGTH: 19
<212> TYPE: DNA
<213> ORGANISM: Artificial Sequence
<220> FEATURE:
<223> OTHER INFORMATION: siRNA_0010 sense

<400> SEQUENCE: 26
gaagccaacc cuugucga                                                 19

<210> SEQ ID NO 27
<211> LENGTH: 19
<212> TYPE: DNA
<213> ORGANISM: Artificial Sequence
<220> FEATURE:
<223> OTHER INFORMATION: siRNA_0011 sense

<400> SEQUENCE: 27
cccgucaucg gacuuuguu                                                 19

<210> SEQ ID NO 28
<211> LENGTH: 19
<212> TYPE: DNA
<213> ORGANISM: Artificial Sequence
<220> FEATURE:
<223> OTHER INFORMATION: siRNA_0012 sense

<400> SEQUENCE: 28
gaaugugggc cguaacaau                                                 19

<210> SEQ ID NO 29
<211> LENGTH: 19
<212> TYPE: DNA
<213> ORGANISM: Artificial Sequence
<220> FEATURE:
<223> OTHER INFORMATION: siRNA_0001 antisense

<400> SEQUENCE: 29
uccuaguagu cacucgcgg                                                 19

<210> SEQ ID NO 30
<211> LENGTH: 19
<212> TYPE: DNA
<213> ORGANISM: Artificial Sequence
<220> FEATURE:
<223> OTHER INFORMATION: siRNA_0002 antisense

<400> SEQUENCE: 30
aauucggcgg gccaggagg                                                 19

<210> SEQ ID NO 31
<211> LENGTH: 19
<212> TYPE: DNA
<213> ORGANISM: Artificial Sequence
<220> FEATURE:
<223> OTHER INFORMATION: siRNA_0003 antisense

<400> SEQUENCE: 31
auuucgucau gccgaggug                                                 19

<210> SEQ ID NO 32
<211> LENGTH: 19
<212> TYPE: DNA
<213> ORGANISM: Artificial Sequence
<220> FEATURE:

<223> OTHER INFORMATION: siRNA_0004 antisense

<400> SEQUENCE: 32
ugucgcacau gauuucgca                                                    19

<210> SEQ ID NO 33
<211> LENGTH: 19
<212> TYPE: DNA
<213> ORGANISM: Artificial Sequence
<220> FEATURE:
<223> OTHER INFORMATION: siRNA_0005 antisense

<400> SEQUENCE: 33
acguaugagu uacugccac                                                    19

<210> SEQ ID NO 34
<211> LENGTH: 19
<212> TYPE: DNA
<213> ORGANISM: Artificial Sequence
<220> FEATURE:
<223> OTHER INFORMATION: siRNA_0006 antisense

<400> SEQUENCE: 34
uuuaaacccu cucgcaagc                                                    19

<210> SEQ ID NO 35
<211> LENGTH: 19
<212> TYPE: DNA
<213> ORGANISM: Artificial Sequence
<220> FEATURE:
<223> OTHER INFORMATION: siRNA_0007 antisense

<400> SEQUENCE: 35
acgaucugca cucucaagc                                                    19

<210> SEQ ID NO 36
<211> LENGTH: 19
<212> TYPE: DNA
<213> ORGANISM: Artificial Sequence
<220> FEATURE:
<223> OTHER INFORMATION: siRNA_0008 antisense

<400> SEQUENCE: 36
ugaaauuggg uuuguggcc                                                    19

<210> SEQ ID NO 37
<211> LENGTH: 19
<212> TYPE: DNA
<213> ORGANISM: Artificial Sequence
<220> FEATURE:
<223> OTHER INFORMATION: siRNA_0009 antisense

<400> SEQUENCE: 37
ugucugacua ugcaaguac                                                    19

<210> SEQ ID NO 38
<211> LENGTH: 19
<212> TYPE: DNA
<213> ORGANISM: Artificial Sequence
<220> FEATURE:
<223> OTHER INFORMATION: siRNA_0010 antisense

<400> SEQUENCE: 38
ucgacaaagg guuggcuuc                                                    19

-continued

```
<210> SEQ ID NO 39
<211> LENGTH: 19
<212> TYPE: DNA
<213> ORGANISM: Artificial Sequence
<220> FEATURE:
<223> OTHER INFORMATION: sirna_0011 antisense

<400> SEQUENCE: 39
aacaaagucc gaugacggg                                                       19

<210> SEQ ID NO 40
<211> LENGTH: 19
<212> TYPE: DNA
<213> ORGANISM: Artificial Sequence
<220> FEATURE:
<223> OTHER INFORMATION: siRNA_0012 antisense

<400> SEQUENCE: 40
auuguuacgg cccacauuc                                                       19

<210> SEQ ID NO 41
<211> LENGTH: 1368
<212> TYPE: PRT
<213> ORGANISM: Streptococcus pyogenes

<400> SEQUENCE: 41

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255
```

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe

```
            675                 680                 685
Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
                1025                1030                1035

Tyr Ser Asn Ile Met Asn Phe Phe Lys Thr Glu Ile Thr Leu Ala
                1040                1045                1050

Asn Gly Glu Ile Arg Lys Arg Pro Leu Ile Glu Thr Asn Gly Glu
                1055                1060                1065

Thr Gly Glu Ile Val Trp Asp Lys Gly Arg Asp Phe Ala Thr Val
                1070                1075                1080

Arg Lys Val Leu Ser Met Pro Gln Val Asn Ile Val Lys Lys Thr
                1085                1090                1095
```

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 42
<211> LENGTH: 1053
<212> TYPE: PRT
<213> ORGANISM: Staphylococcus aureus

<400> SEQUENCE: 42

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu

```
            85                  90                  95
Ser Gln Lys Leu Ser Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
        210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
            275                 280                 285

Lys Gln Lys Lys Lys Pro Thr Leu Lys Gln Ile Ala Lys Glu Ile Leu
        290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
            355                 360                 365

Thr Asn Leu Asn Ser Glu Leu Thr Gln Glu Glu Ile Glu Gln Ile Ser
        370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
        450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
                500                 505                 510
```

```
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
    530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
    595                 600                 605
Leu Asn Leu Ala Lys Gly Lys Gly Arg Ile Ser Lys Thr Lys Lys Glu
    610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
            660                 665                 670
Val Lys Ser Ile Asn Gly Gly Phe Thr Ser Phe Leu Arg Arg Lys Trp
    675                 680                 685
Lys Phe Lys Lys Glu Arg Asn Lys Gly Tyr Lys His His Ala Glu Asp
    690                 695                 700
Ala Leu Ile Ile Ala Asn Ala Asp Phe Ile Phe Lys Glu Trp Lys Lys
705                 710                 715                 720
Leu Asp Lys Ala Lys Lys Val Met Glu Asn Gln Met Phe Glu Glu Lys
                725                 730                 735
Gln Ala Glu Ser Met Pro Glu Ile Glu Thr Glu Gln Glu Tyr Lys Glu
            740                 745                 750
Ile Phe Ile Thr Pro His Gln Ile Lys His Ile Lys Asp Phe Lys Asp
    755                 760                 765
Tyr Lys Tyr Ser His Arg Val Asp Lys Lys Pro Asn Arg Glu Leu Ile
    770                 775                 780
Asn Asp Thr Leu Tyr Ser Thr Arg Lys Asp Asp Lys Gly Asn Thr Leu
785                 790                 795                 800
Ile Val Asn Asn Leu Asn Gly Leu Tyr Asp Lys Asp Asn Asp Lys Leu
                805                 810                 815
Lys Lys Leu Ile Asn Lys Ser Pro Glu Lys Leu Leu Met Tyr His His
            820                 825                 830
Asp Pro Gln Thr Tyr Gln Lys Leu Lys Leu Ile Met Glu Gln Tyr Gly
    835                 840                 845
Asp Glu Lys Asn Pro Leu Tyr Lys Tyr Glu Glu Thr Gly Asn Tyr
    850                 855                 860
Leu Thr Lys Tyr Ser Lys Lys Asp Asn Gly Pro Val Ile Lys Lys Ile
865                 870                 875                 880
Lys Tyr Tyr Gly Asn Lys Leu Asn Ala His Leu Asp Ile Thr Asp Asp
                885                 890                 895
Tyr Pro Asn Ser Arg Asn Lys Val Val Lys Leu Ser Leu Lys Pro Tyr
            900                 905                 910
Arg Phe Asp Val Tyr Leu Asp Asn Gly Val Tyr Lys Phe Val Thr Val
    915                 920                 925
```

-continued

```
Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr  Tyr Arg Glu Tyr Leu  Glu Asn Met
            995                 1000                1005

Asn Asp Lys Arg Pro Pro Arg  Ile Ile Lys Thr Ile  Ala Ser Lys
        1010                1015                1020

Thr Gln Ser Ile Lys Lys Tyr  Ser Thr Asp Ile Leu  Gly Asn Leu
        1025                1030                1035

Tyr Glu  Val Lys Ser Lys Lys  His Pro Gln Ile Ile  Lys Lys Gly
        1040                1045                1050
```

COMPOSITIONS AND METHODS TO IMPROVE ANTI-ANGIOGENIC THERAPY AND IMMUNOTHERAPY

CLAIM OF PRIORITY

This application is a national stage application of PCT/US2018/041284, filed Jul. 9, 2018, which claims the benefit of U.S. Provisional Application Ser. No. 62/530,124, filed on Jul. 8, 2017. The entire contents of the foregoing are incorporated herein by reference.

FEDERALLY SPONSORED RESEARCH OR DEVELOPMENT

This invention was made with Government support under Grant Nos. CA080124, CA126642, CA197743, CA096915, OD008780, CA137167 awarded by the National Institutes of Health, and Grant No. W81XWH-10-1-0016 awarded by the Department of Defense. The Government has certain rights in the invention.

TECHNICAL FIELD

This invention relates to agents that inhibit CX3C chemokine ligand 1 (CX3CL1, also known as Fractalkine) in endothelial cells to reduce or inhibit immunosuppression mechanisms that are co-opted by cancer cells to evade host immune system, and more particularly to agents that reduce immunosuppression in the context of therapies that target vascular endothelial growth factor (VEGF)-dependent signaling, and methods of use thereof.

BACKGROUND

Cancer cells are known to co-opt angiogenesis—the physiological process of generating and integrating new blood vessels from pre-existing vessels—for competitive advantage—e.g. to obtain nutrients and to metastasize to distal sites. (1). The VEGF signaling pathway is a key component of pathological angiogenesis in most cancers (2-5). Targeting the down-regulation of VEGF-dependent signaling in cancers may reduce the likelihood of angiogenesis and thereby also reduce the likelihood of metastasis. Direct inhibitors of VEGF have been developed as a new class of anti-cancer therapy and approved by the Food and Drug Administration (FDA) to treat various solid tumors, starting with metastatic colorectal cancer (CRC) in 2004 (1). The current anti-VEGF drugs confer modest increases in patient lifespan. The low efficacy of current anti-VEGF drugs has been attributed to cancers evolving resistance to the anti-VEGF drugs, however confirmation of this and detailed understanding of particular resistance mechanisms remain active areas of research (3, 4, 6-13).

SUMMARY

The present invention is based, at least in part, on the discovery that inhibiting CX3C chemokine ligand 1 (CX3CL1, aka Fractalkine) in endothelial cells reduces immunosuppression mechanisms that are co-opted by cancer cells to evade host immune system. Thus, described herein are agents that target CX3CL1 to reduce immunosuppression in the context of therapies that target vascular endothelial growth factor (VEGF)-dependent signaling, and methods of use thereof.

Thus, provided herein are compositions comprising an inhibitory agent that reduces expression or activity of C-X3-C chemokine ligand 1 (CX3CL1, also known as Fractalkine), encapsulated within an endothelial cell delivery vehicle and/or linked to an endothelial cell targeting agent.

In some embodiments, the inhibitory nucleic acid comprises a siRNA, shRNA, guide RNA, or antisense oligonucleotide sequence that targets CX3CL1. In some embodiments, the siRNA is chemically modified—e.g. with 2'-O-methyl modification—that confers increased siRNA half-life.

In some embodiments, the inhibitory agent comprises a peptide nucleic acid (PNA), locked nucleic acid (LNA), or bridged nucleic acid (BNA) that binds select genomic sites and reduces CX3CL1 expression.

In some embodiments, the inhibitory agent is an antibody against CX3CL1 or CX3 chemokine receptor 1 (CX3CR1).

In some embodiments, one or more of the inhibitory agents are encapsulated within a lipid nanoparticle, e.g., a nanoparticle that targets endothelial cells and has composition known as 7C1, SAINT-C18 lipoplexes, PEGylated SAINT-C18 lipoplexes, RPP-nanoplexes, or PLCP.

In some embodiments, one or more inhibitory agents as described herein are linked to a cell-penetrating peptide, i.e., that can penetrate cell membranes.

Also provided herein are pharmaceutical compositions comprising the compositions described herein, and a pharmaceutically acceptable carrier.

In some embodiments, the pharmaceutical compositions include an anti-angiogenic agent, e.g., a VEGF inhibitor.

Also provided herein are methods for treating cancer. The methods include administering to a subject in need thereof a therapeutically effective amount of a pharmaceutical composition as described herein.

In some embodiments, the methods include administering a therapeutically effective amount of an anti-angiogenic agent to the subject. In some embodiments, the subject has been treated with an anti-angiogenic agent prior to administration of the pharmaceutical composition described herein.

In some embodiments, the cancer is resistant to the anti-angiogenic agent, e.g., is resistant to the anti-angiogenic agent such that the cancer cells evade action by the host immune system and/or continue to express VEGF-dependent signaling.

In some embodiments, the anti-angiogenic agent is a VEGF inhibitor.

In some embodiments, the anti-angiogenic agent is administered prior to or concurrently with a pharmaceutical composition described herein.

In some embodiments, the cancer is a carcinoma, e.g., a colorectal, breast, or lung carcinoma.

Also provided herein are the compositions and pharmaceutical compositions described herein for use in the treatment of cancer. In some embodiments, the cancer is a carcinoma, e.g., a colorectal, breast, or lung carcinoma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-2G. Ly6C$^{low}$ monocytes require CX3CL1/CX3CR1 signaling to infiltrate into tumors during anti-VEGFR2 therapy. (A) Abdominal imaging window on a live mouse bearing syngeneic SL4 CRC (filled in arrow) in the cecum (clear arrow). (B and C) Images of crawling CX3CR1$^+$ leukocytes inside the post-capillary venule (highlighted with TRITC-Dextran) in a normal cecum (B) and in the tumor (C) of a Cx3cr1$^{gfp/+}$ mouse, which labels Ly6C$^{low}$ monocytes with EGFP. Ly6C$^{low}$ monocytes are also observed in the tumor (C). (D) Snapshot image taken at 8 sec of a movie showing flowing, rolling, and crawling CX3CR1$^+$ Ly6C$^{low}$ monocytes inside the blood vessels in an SL4 tumor. (E) Snapshot image showing CX3CR1$^+$ Ly6C$^{low}$ monocytes undergoing extravasation in an SL4 tumor. Blood vessels were contrast enhanced with TRITC-Dextran. (F) Flux of flowing, rolling, and crawling CX3CR1$^+$ Ly6C$^{low}$ monocytes in blood circulation in SL4 tumor-bearing Cx3cr1$^{gfp/+}$ mice treated with either control rat IgG (C) or DC101 (D). (G) Flux of flowing, rolling, and crawling Ly6C$^{low}$ monocytes in blood circulation in SL4 tumor-bearing C57BL/6 wild-type mice at 5 days after DC101 treatment. Ly6C$^{low}$ monocytes were isolated from C57BL/6 WT (WT) or Cx3cr1$^{-/-}$ mice (KO), fluorescently labeled, and adoptively transferred into DC101-treated SL4 tumor-bearing C57BL/6 WT animals. n=7/group. Data are represented as mean±SEM. Two-tailed t tests. *, p<0.05. Data are representative of three independent experiments (F, G). Scale bars=100 μm (B-E).

FIGS. 10A-10D. Identification of three distinct subsets of innate immune cells in CRCs. (A) CD11b+Gr1+ cells in SL4 tumors. C57BL/6 WT mice bearing SL4 tumors were treated with either control rat IgG or DC101. CD11b+Gr1+ cells in tumor infiltrate were analyzed on day 12 by flow cytometry. Data are represented as mean±SEM. n=8/group. Two-tailed t tests. *, p<0.05 versus control. Data are representative of three independent experiments. The graph depicts data for CD11b+Gr1+ population relative to total viable cells. (B) Relative gene expression level of tumor-isolated each subset of myeloid cells compared to Ly6Chigh monocytes. 4 samples were pooled into a PCR array plate. (C) Protein levels measured from conditioned media from culture of tumor-isolated each subset of myeloid cells. Data are represented as mean±SEM. n=5/group. ANOVA with Holm-Sidak post-hoc test. *, p<0.05 versus Ly6Chigh monocytes. The expression level of immunosuppressive cytokines (IL-10 and TGF-β1) are high in both Ly6Clow monocytes and Ly6G+ neutrophils, and relatively low in Ly6Chigh monocytes. Ly6Chigh monocytes do not seem to play an important role in immunosuppression in this model shown by their low number and less-immunosuppressive phenotype. A chemokine known to attract CXCR2+ granulocytic cells (e.g., Ly6G+ neutrophils) is upregulated in Ly6Clow monocytes and neutrophils (i.e., CXCL5). (D) C57BL/6 WT mice bearing syngeneic orthotopic SL4 tumors were treated with either control rat IgG or DC101. Protein levels were measured from tumor tissue lysates. Relative protein expression level of DC101-treated tumors compared to control tumors is shown in FIG. 6A. Data are represented as mean±SEM. n=5/group FIGS. 11A-11B. Anti-VEGFR2 therapy facilitates early infiltration of Ly6Clow monocytes into spontaneous rectal tumors. (A and B) Monocytes and neutrophils in spontaneous rectal tumors. Conditional Apc knock-out mice bearing spontaneous rectal tumors were treated with either control rat IgG ("C"), DC101 ("D"), or anti-Ly6G antibody+DC101 ("G+D"). Each subset of myeloid cells in tumor infiltrate was analyzed on day 7 (A) and 14 (B) by flow cytometry. Top row, Ly6Clow monocyte; center row, Ly6Chigh monocyte; bottom row, Ly6G+ neutrophil. Data are represented as mean±SEM. n=7/group. *, p<0.05 versus control. #, p<0.05 versus DC101. The graphs depict data for the absolute number of cells per mg of tumor tissue.

DETAILED DESCRIPTION

Figures 1A, 1B, 1C:
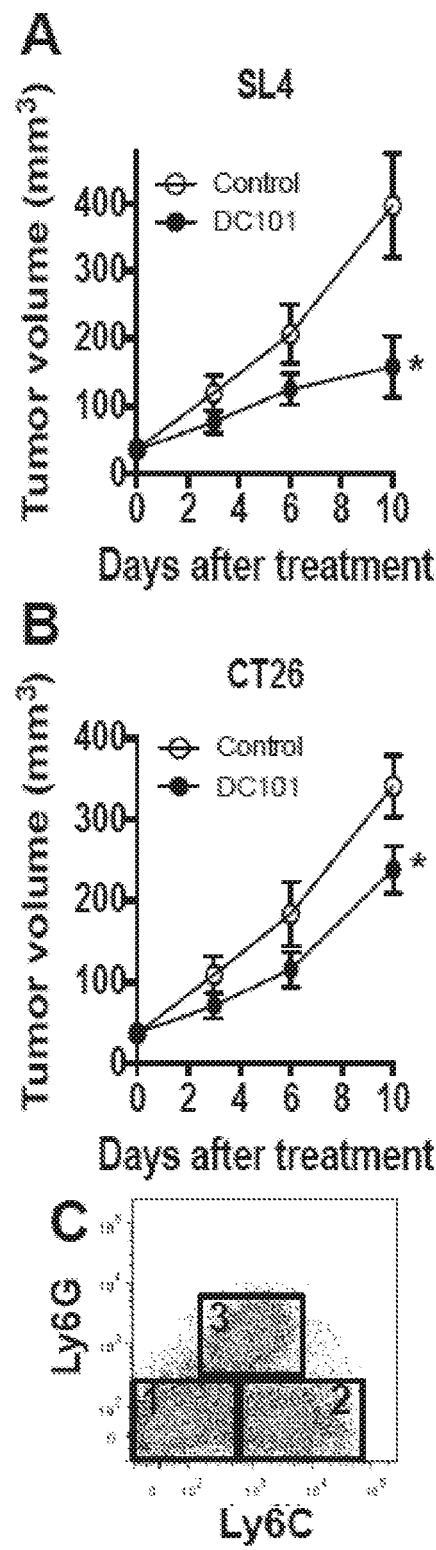
FIGS. 1A-1G. Anti-VEGFR2 therapy facilitates early infiltration of Ly6C$^{low}$ monocytes into tumors. (A and B) Tumor volume was measured using a high-frequency ultrasound imaging system for syngeneic SL4 tumors orthotopically grown in the colon of C57BL/6 mice (A) and CT26 tumors in BALB/c mice (B). Tumors were treated with either non-specific rat IgG (Control) or monoclonal anti-VEGFR2 antibody, DC101 (40 mg/kg, every 3 days). n=8/group. (C) A representative flow cytometry plot depicting the three different subsets of myeloid cell populations. 1, Ly6C$^{low}$ monocyte. 2, Ly6C$^{high}$ monocyte. 3, Ly6G$^+$ neutrophil. wild-type (WT) C57BL/6 mice bearing orthotopic SL4 tumors were treated with DC101, and immune cells in the tumor infiltrate were analyzed on day 5 by flow cytometry. Gated on CD45$^+$ Lin$^-$ F4/80$^-$ CD11c$^-$ CD11b$^+$. As these cells were defined as F4/80$^-$, tumor-associated macrophages (TAMs: F4/80$^+$) are excluded. (D and E) C57BL/6 WT mice bearing SL4 tumors were treated with either control rat IgG (C) or DC101. Each subset of myeloid cells in tumor infiltrate was analyzed on day 5 (D) and 12 (E) by flow cytometry. Top row, Ly6C$^{low}$ monocyte; center row, Ly6C$^{high}$ monocyte; bottom row, Ly6G$^+$ neutrophil. n=8/group. (F and G) BALB/c WT mice bearing syngenic CT26 tumors in the colon were divided into control (C, rat IgG)) and DC101 treatment groups, and the myeloid cell subsets in the tumor infiltrate were analyzed on day 5 (F) and 12 (G) by flow cytometry. The graphs depict the absolute number of cells per mg of tumor tissue. Top row, Ly6C$^{low}$ monocyte; center row, Ly6C$^{high}$ monocyte; bottom row, Ly6G$^+$ neutrophil. n=8/group. Data are represented as mean±SEM. Two-tailed t tests. * p<0.05 versus control. Data are representative of four (A-B) or three (D-G) independent experiments.

The local chemical and cellular environment of tumors can impact tumor pathophysiology—e.g. cell growth rate, likelihood of metastasis, gene and protein expression (7, 8, 10, 12, 14-22). Host immune cells are recruited to the tumor and these immune cells can impact refractoriness to anti-angiogenic therapy (13, 23, 24). Among various types of leukocytes, a growing body of evidence suggests that immunosuppressive innate immune cells contribute to this resistance, in addition to cancer cell immune evasion (6, 25-27). However, these myeloid cells are a collection of diverse subsets of CD11b$^+$ monocytic and granulocytic cells (27-30), which have been often studied together rather than as clearly defined sub-populations. Furthermore, the role of Ly6C$^{low}$ monocytes, also known as non-classical monocytes, have not yet been clearly characterized or extensively investigated in the context of anti-VEGF cancer therapy or immunosuppression.

Moreover, mechanistic studies on the role of chemokines/chemokine receptors in each specific sub-population of innate immune cells in cancers have not been conducted, even though the importance of chemokines in leukocyte trafficking has long been widely accepted (31, 32). The lack of suitable methods for in vivo longitudinal cellular-level monitoring of leukocytes in CRCs of small animal models has limited previous efforts to elucidate the highly dynamic immune microenvironment. Thus, the role and kinetics of specific subsets of innate immune cells in conferring resistance to anti-VEGF therapy is not known.

Herein the immunosuppressive role of Ly6C$^{low}$ monocytes recruited to tumors in the context of anti-VEGF therapy is disclosed. Without wishing to be bound by theory, anti-VEGF therapy triggers a sequence of molecular events that culminate in immunosuppressive action of Ly6C$^{low}$ monocytes via activated vascular endothelial cells in tumors and evasion of the cancer cells from surveillance—e.g., identification of specific cells and the selective killing of those cells—by the host immune system. In brief, first anti-VEGF therapy induces CX3CL1 expression in tumor vascular endothelial cells. The CX3CL1 protein is secreted and at a sufficiently high extracellular concentration serves to recruit Ly6C$^{low}$ monocytes expressing CX3CR1, the only receptor for CX3CL1, on the surface. The recruited Ly6C$^{low}$ monocytes produce CXCL5, a secreted ligand for CXCR2 that is sufficient to recruit CXCR2 expressing neutrophils to the local environment. The recruited neutrophils and/or additional neutrophil secreted factors mediate immunosuppression of the local environment, which significantly reduce the rate that cancer cells are recognized and targeted by anti-tumor host immune system.

Herein compositions and methods to reduce CX3CL1 expression and/or CX3CL1 activity in tumor vascular endothelial cells are detailed. These compositions and methods improve the efficacy of anti-VEGF agents by reducing recruitment of Ly6C$^{low}$ monocytes expressing CX3CR1 to tumors through activated tumor vascular endothelium. In one embodiment the composition is a nanoparticle containing chemically modified siRNAs targeting CX3CL1 and the nanoparticle possesses a targeting moiety that biases recruitment of the nanoparticle to endothelial cells. One such composition is termed 7C1-Axo-siCX3CL1. Results of experiments with mice treated with DC101, a monoclonal anti-VEGFR2 antibody, and 7C1-Axo-siCX3CL1 compared to the mice treated with anti-VEGFR2 alone show that the former combination treatment confers significantly reduced tumor growth.

Myeloid-derived suppressor cells (MDSCs), which is defined by the positivity of Gr1 cell surface marker, are major innate cell population conferring immunosuppression. However, Gr1 is not a single surface marker, but rather a complex of proteins Ly6C and Ly6G. Due to the complexity of Gr1, previous studies that utilized Gr1 staining were not able to provide a clear separation of the sub-populations (62). Recent reports that adopted Ly6C and Ly6G for sub-population separation focused only on Gr1$^{high}$ myeloid cells, which include Ly6C$^{high}$ monocytes and Ly6G$^+$ granulocytes (39)(25-27, 42, 62). Moreover, the definition of the myeloid cell sub-populations using surface markers has been ambiguous among research groups (35-38, 42, 43). Unlike Gr1$^{high}$Ly6C$^{high}$ monocytic and Gr1$^{high}$Ly6G$^+$ granulocytic MDSCs (6, 23, 24), Ly6C$^{low}$ monocytes represent a distinct cell population (FIG. 1C) that has never been studied for its role in conferring resistance to anti-VEGF therapy.

As discussed above, there have been reports on the presence of several different myeloid cell subsets (i.e. Gr1$^+$, Ly6C$^{high}$, or Tie2$^+$ monocytes and granulocytic cells) and their respective roles in resistance to anti-angiogenic therapy. Here we found that Ly6C$^{low}$ monocytes along with their immunosuppressive functions form a distinct population of myeloid cells, which are immunophenotypically different from the Gr1$^+$ or Tie2$^+$ monocytes and granulocytic cells described previously. Furthermore, we identified Ly6C$^{low}$ monocyte infiltration after anti-VEGFR2 therapy, while these cells have not been observed in previous reports in the context of anti-VEGF therapy. Ours is the first report that investigates the ability of Ly6C$^{low}$ monocytes to confer resistance to anti-VEGF therapy in tumors.

Furthermore, we found immunosuppression—rather than alternative angiogenesis mechanisms—in the tumor microenvironment is the key mechanism conferring resistance to anti-VEGF therapy exerted by Ly6C$^{low}$ monocytes. OIn the other hand, previous reports implicated proangiogenic functions of myeloid cells or monocytes (i.e. CD11b$^+$ Gr1$^+$ cells or Ly6G$^+$ granulocytes) in anti-VEGF therapy resistance in some tumors, but not their immune-regulatory functions.

We have previously shown that low doses of anti-VEGF therapy can alleviate abnormal morphology and function of tumor vasculature (normalization) resulting in improvement of tumor microenvironment and anti-tumor immunity (63, 64). On the other hand, high-dose or prolonged treatment of anti-VEGF therapy promotes hypoxia and immunosuppression in the tumor microenvironment in both clinical and preclinical studies (1, 6, 24, 71-74). The latter case explains one mechanism of anti-VEGF therapy resistance in patients, which is consistent with our observations in colorectal cancer (CRC) models. Indeed, the therapeutic dose of bevacizumab currently used in the clinic is often considered as a high-dose (65), which is comparable to the dose we used in our study (maximum effective dose). These findings imply that immune-resistance may hinder responsiveness to anti-VEGF/VEGFR therapy. Here, we claim that high-dose anti-VEGFR2 therapy induces immunosuppression and that this is occurring via the interaction of CX3CL1 producing endothelial cells and CX3CR1 expressing Ly6C$^{low}$ monocytes.

In this study, we clearly distinguished three different innate immune cell sub-populations based on their immunophenotype (i.e., Ly6C and Ly6G) (FIG. 1C). Although Ly6C$^{low}$ monocytes have been described and characterized in previous publications, studies on their roles in vivo have been mostly in non-cancer settings (32, 48, 49). Interestingly, Hanna et al. recently reported that patrolling Ly6C$^{low}$ monocytes are important in recruiting NK cells to prevent cancer metastasis in the lung, which is characterized by an exceptionally abundant NK cell population compared to other tissues (66). However, the immunosuppressive functions of Ly6C$^{low}$ monocytes have not been reported in any context, especially in primary tumors during the process of anti-angiogenic therapy resistance. Of note, we observed only a negligible number of NK cells in our CRC models (FIG. 15A), similar to other tumor models available in our laboratory.

Figure 6A:
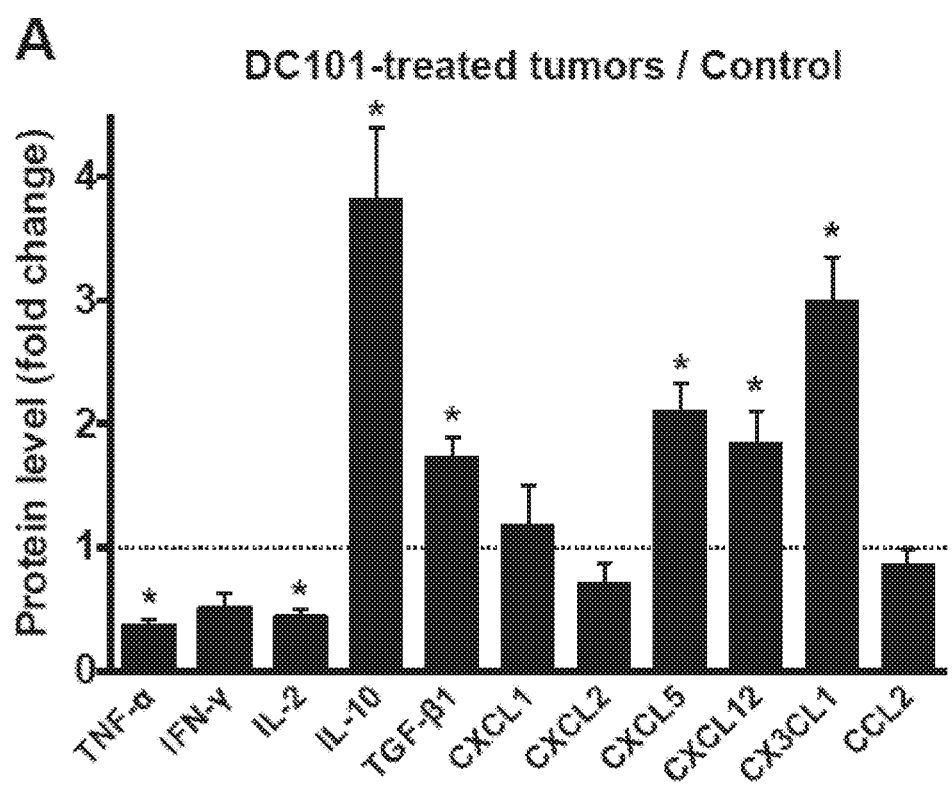
FIGS. 6A-6G. Ly6C$^{low}$ monocytes drive immunosuppression during anti-VEGFR2 treatment in CRCs. (A) C57BL/6 WT mice bearing syngeneic orthotopic SL4 tumors were treated with either control rat IgG or DC101. Protein levels were measured on day 12 after treatment from tumor tissue lysates (FIG. 10D). (B and C) Flow cytometric analysis of CD4$^+$ (B) and CD8$^+$ T cells (C) in SL4 tumors as indicated: WT mice bearing SL4 tumors treated with control rat IgG; WT mice bearing SL4 tumors treated with DC101; $Cx_3cr1^{-/-}$ mice bearing SL4 tumors treated with DC101 without cell transfer; DC101-treated $Cx_3cr1^{-/-}$ mice received adoptive transfer of tumor-isolated WT Ly6C$^{low}$ monocytes. The graphs depict data for the absolute number of cells per mg of tumor tissue (B-C). The lymphocyte infiltrate in the tumor was analyzed on day 12 by flow cytometry. (D and E) Flow cytometric analysis of CD8$^+$ T cells. The graphs depict data for Granzyme B$^+$ (D) or PD-1$^+$ (E) populations relative to total CD8$^+$ T cells. The lymphocyte infiltrate in the tumor was analyzed on day 12 by flow cytometry. n=8/group. Data are represented as mean± SEM. *, p<0.05. (F and G) CFSE-based T cell proliferation assays. CellTrace™-labeled splenic CD8$^+$ (F) or CD4$^+$ T cells (G) from syngeneic mice were activated and co-incubated with either tumor-isolated Ly6C$^{low}$ monocytes, Ly6C$^{high}$ monocytes, or neutrophils with or without anti-IL-10 neutralizing antibody as indicated. n=3/group. Data are represented as mean±SEM. (B-G) Comparison between groups was made using ANOVA with Holm-Sidak post-hoc test. *, p<0.05. Data are representative of three independent experiments.
Figures 6B, 6C, 6D, 6E:
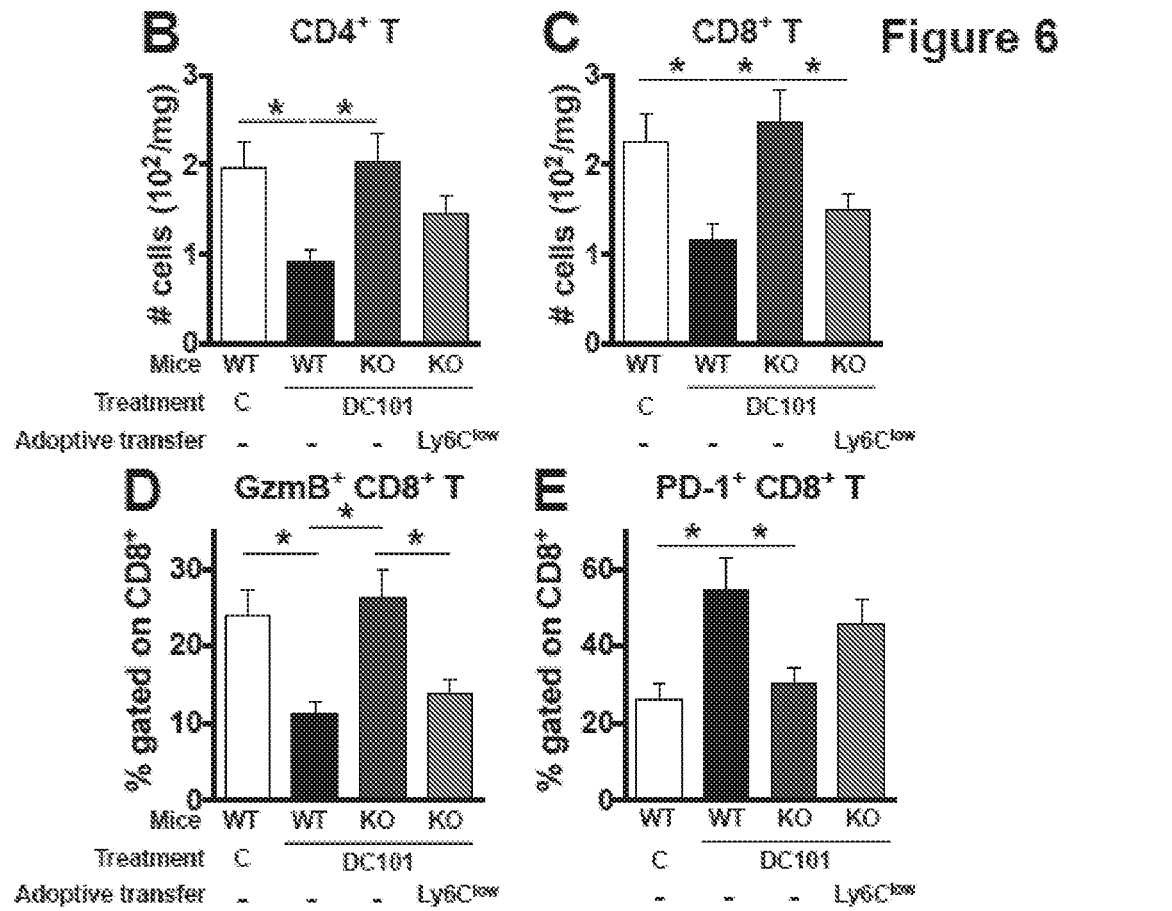
Figures 6F, 6G:
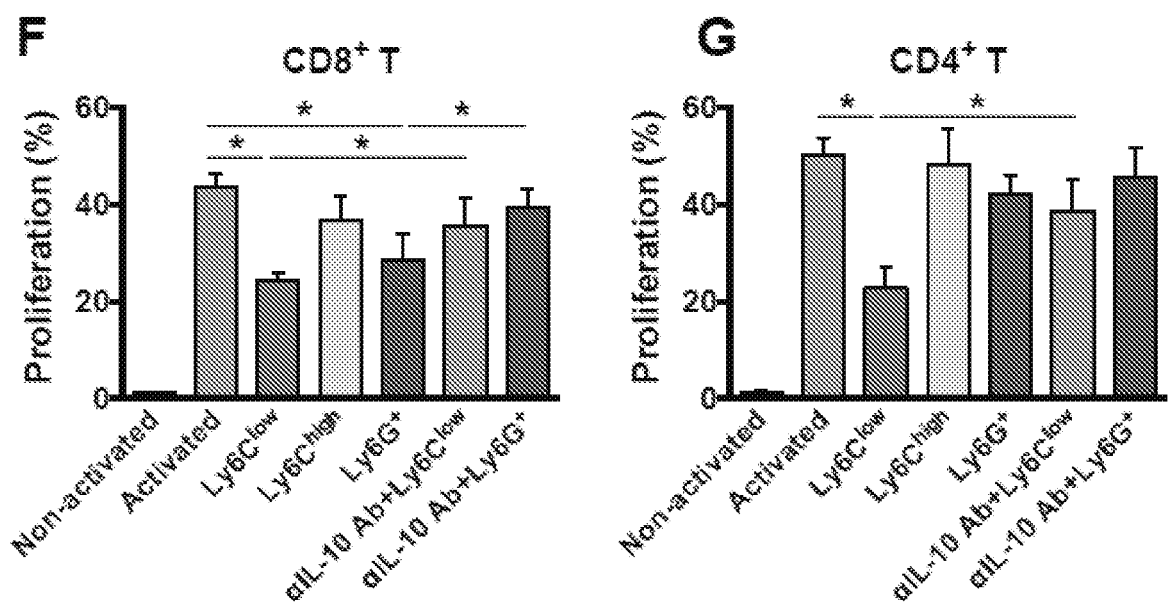

In our CRC models, the expression levels of immunosuppressive cytokines (i.e., IL-10 and TGF-β1) were high in both Ly6C$^{low}$ monocytes and neutrophils. DC101-treated tumors—abundantly infiltrated by Ly6C$^{low}$ monocytes and neutrophils—were composed of significantly fewer effector CD4$^+$ and CD8$^+$ T cells and those T cells that were present expressed more PD-1 and less Granzyme B. This phenotype was ablated in Cx3cr1$^{-/-}$ mice. An in vitro CFSE assay revealed that Ly6C$^{low}$ monocytes inhibited CD4$^+$ and CD8$^+$ T cell proliferation—a phenotype reversed by using an anti-IL-10 neutralizing antibody (FIGS. 6F and 6G). Thus, DC101-induced recruitment of IL-10-producing Ly6C$^{low}$ monocytes and neutrophils shifted the tumor microenvironment towards immunosuppression, leading to less infiltration of cytotoxic effector T lymphocytes. Recently, our group showed that modulation of innate immune cells (i.e. TAMs) subsequently regulates the activity of cytotoxic T cells in breast cancer models, and that depletion of the cytotoxic T cells using anti-CD8 neutralizing antibody abrogated the effect of TAM modulation (63). Therefore, if we deplete CD8$^+$ T cells in our colon cancer model after blocking Ly6C$^{low}$ monocyte infiltration, we would expect abrogated anti-tumor immunity even with decreased number of Ly6C$^{low}$ monocytes in tumors.

By genetically or pharmacologically depleting one specific subset of myeloid cells at a time, we found that Ly6C$^{low}$ monocyte infiltration promoted subsequent neutrophil recruitment during anti-VEGFR2 treatment (FIG. 4). We also confirmed that the adoptive transfer of Ly6C$^{low}$ monocytes alone increased the numbers of both Ly6C$^{low}$ monocytes and neutrophils in tumors of Cx3cr1$^{-/-}$ mice. Furthermore, these early-infiltrating Ly6C$^{low}$ monocytes overexpressed the chemokine CXCL5, which attracted CXCR2+ neutrophils. Other chemokines known to bind to CXCR2 (i.e. CXCL1 and CXCL2) did not seem to be important in attracting neutrophils in our models (FIGS. 4H, 6A and 10D), even though CXCL1 was previously proposed as a neutrophil attractant secreted from Ly6C$^{low}$ monocytes in non-tumor models (49).

Based on our findings, we sought to develop a novel therapeutic strategy with the potential for clinical translation. We hypothesized that therapeutic targeting of CX3CL1 would selectively and potently block the infiltration of Ly6C$^{low}$ monocytes and improve the efficacy of anti-VEGF/VEGFR2 cancer therapy. To specifically and effectively silence CX3CL1, we utilized a gene therapy approach, taking advantage of the recent advances in siRNA design and chemistry that allows the identification of specific and highly potent sequences with minimal immune-stimulation and maximal siRNA stability. We further benefited from the utilization of novel nanoparticle formulations capable of efficacious siRNA delivery to tumor endothelial cells with clinically suitable delivery materials (7C1).

Tumor growth was significantly delayed in combined 7C1-Axo-siCX3CL1 and DC101-treated mice compared to the DC101 single treatment group. Based on the promising therapeutic benefits observed in this study, we look forward to further applications of 7C1 nanoparticles for treatment strategies of various diseases.

While it is clear that endothelial cells in CRC microenvironment produce and upregulate CX3CL1 expression upon anti-VEGFR2 treatment, it is conceivable that there may be other cell types expressing CX3CL1 in the tumor microenvironment. Here, we demonstrate that targeting CX3CL1 in endothelial cells is sufficient to block the infiltration of Ly6C$^{low}$ monocytes and improve survival (FIG. 7). These data indicate endothelial cell-derived CX3CL1 plays a key functional role in the recruitment of Ly6C$^{low}$ monocytes in CRCs during anti-VEGFR2 treatment.

Tumors often escape anti-tumor immune responses through critical immune checkpoint molecules. The recent approval of drugs targeting PD-1 or CTLA-4 shows the potential for inhibiting these pathways. However, this strategy is effective only in some tumor types and in only a portion of patients. Recently, two studies revealed that inhibition of granulocyte recruitment into tumors improves the efficacy of the immune checkpoint blockade (35, 41). Our data describing the immunosuppressive functions of Ly6C$^{low}$ monocytes identify another path for the development of novel therapeutic strategies that can create synergy with the FDA-approved immune checkpoint inhibitors.

In addition, our unique cecum-imaging window developed in this study enabled quantification of dynamic mobilization of Ly6C$^{low}$ monocytes with various types of behaviors over time, unveiling their CX3CR1-dependent infiltration into the tumor from the blood. The cecum window allowed longitudinal imaging for over 4 weeks, unparalleled by other imaging windows for the gut that are applicable only for acute or short-term monitoring. The cecum window can be more broadly applied for investigations of both malignant and non-malignant chronic diseases of the gut, such as inflammatory bowel disease and disorders related to the gut microbiota.

Figure 8:
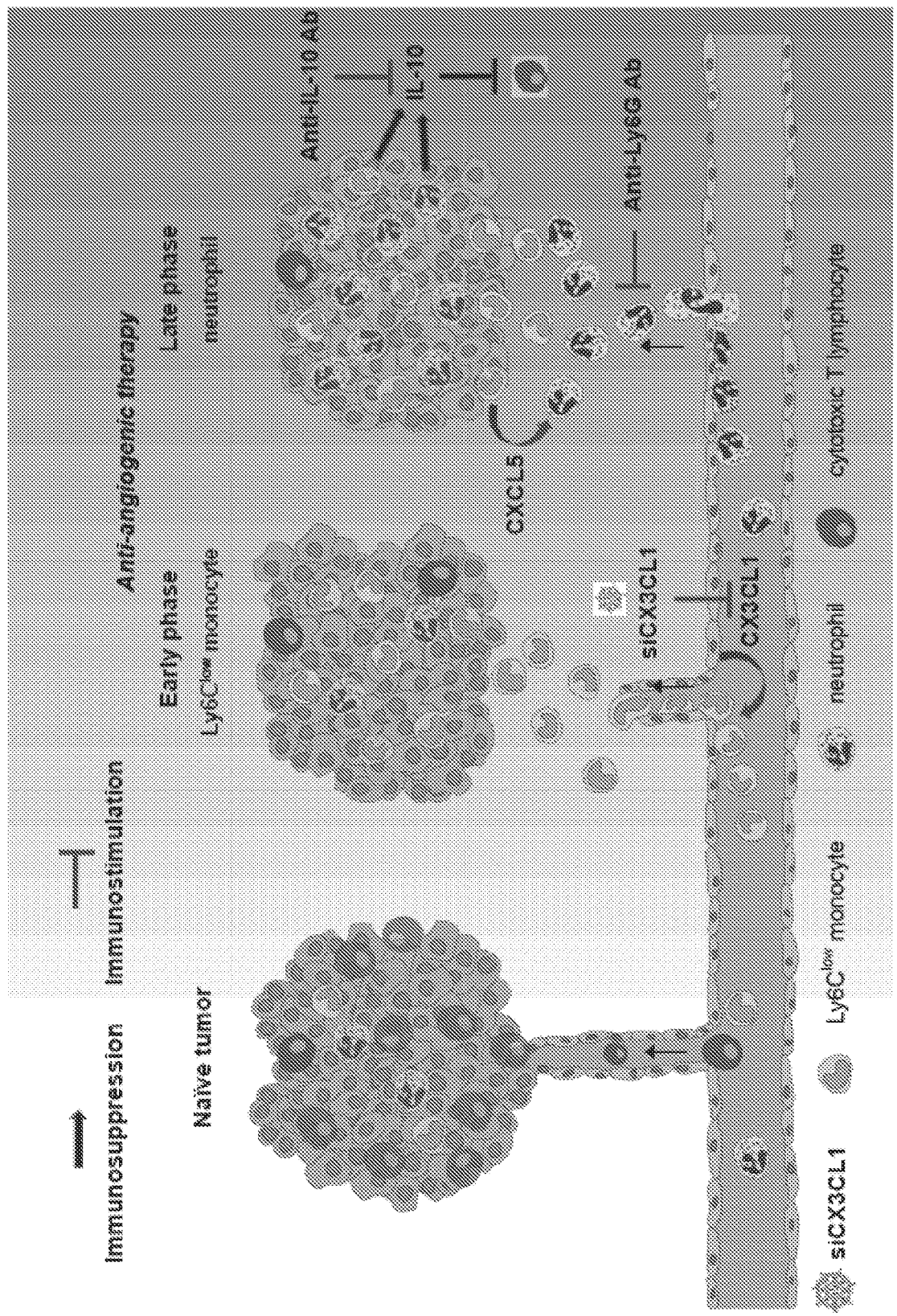
FIG. 8. Graphical cartoon depicts a potential mechanism of anti-angiogenic therapy-induced immunosuppression. Anti-VEGFR2 therapy upregulates the expression of CX3CL1 that recruits CX3CR1$^+$ Ly6C$^{low}$ monocytes (center, "Early phase"), which subsequently attracts neutrophils via CXCL5 (right, "Late phase"), resulting in the formation of an immunosuppressive microenvironment with a reduction of cytotoxic T lymphocytes in the tumor. The multi-step process provides multiple points of intervention to prevent immune resistance and improve the effectiveness of anti-VEGF therapy; arrow reflects immunosuppression and bar-headed arrows reflects immunostimulation.

In summary, we found that Ly6C$^{low}$ monocytes are important drivers of resistance to anti-angiogenic therapy in CRCs through their immunosuppressive functions. Moreover, the increase in CX3CL1 after anti-angiogenic therapy in mouse models mirrored the findings in human tumor specimens. This supports our model that CX3CL1 upregulation results in the recruitment of Ly6C$^{low}$ monocytes, which attract neutrophils to the tumor via CXCL5 and inhibit effector T cell formation (FIG. 8). The multi-step process provides multiple points of intervention to prevent immune suppression and improve the effectiveness of anti-VEGF therapy by modulating the immune microenvironment.

Methods of Treatment

The methods described herein include methods for the treatment of cancer. In some embodiments the cancer is a solid tumor, e.g., a carcinoma. In some embodiments, the disorder is colon cancer. Generally, the methods include administering a therapeutically effective amount of a composition that reduces CX3CL1 expression or activity in endothelial cells as described herein, to a subject who is in need of, or who has been determined to be in need of, such treatment.

As used in this context, to "treat" means to ameliorate at least one symptom of the disorder associated with cancer—e.g. aberrant proliferation, gene expression, signaling, translation, and/or secretion of factors. Often, anti-VEGF therapy has limited efficacy due to immunosuppression local to the cancer cells that is dependent on anti-VEGF induction of CX3CL1 expression in endothelial cancer cells, an initial step that confers recruitment of factors that reduce recruitment and/or activity of host immune system local to the cancer cells. Thus, treatment with compositions and methods described herein can result in a reduction of CX3CL1 expression in endothelial cancer cells that confers a reduction in CX3CL1-mediated immunosuppression in and around the local environment of the cancer cells. Administration of a therapeutically effective amount of a compound described herein for the treatment of a condition associated with CX3CL1-mediated immunosuppression will result in decreased immunosuppression in and around the local environment of the cancer cells and potentially confer reduced or slowed growth of the cancer cells mediated by host immune system and/or anti-VEGF therapies.

The compositions and methods herein described are useful in the treatment of disorders associated with abnormal apoptotic or differentiative processes, e.g., cellular proliferative disorders or cellular differentiative disorders, e.g., cancer, e.g., by producing an active or passive immunity. Examples of cellular proliferative and/or differentiative disorders include cancer, e.g., carcinoma, sarcoma, and metastatic disorders. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

Chemokine (C-X3-C Motif) Ligand 1 (CX3CL1) Inhibitory Nucleic Acids

The present compositions and methods include inhibitory nucleic acids targeting mouse CX3CL1 transcript (genomic sequence NCBI Gene ID 20312) or targeting human CX3CL1 transcript (genome sequence NCBI Gene ID 6376). Exemplary sequences for CX3CL1 are as follows:

| Species | mRNA | Protein | Genomic |
|---|---|---|---|
| Mouse | NM_009142.3 | NP_033168.2 | NC_000074.6 Range 94772180-94782427 (Reference GRCm38.p4 C57BL/6J) |
|  | NM_002996.5 (var. 1) | NP_002987.1 (isoform 1) | NC_000016.10 Range 57372458-57385048 (GRCh38.p12 Primary Assembly) |
|  | NM_001304392.2 (var 2) | NP_001291321.1 (isoform 2) |  |

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics which hybridize to at least a portion of the target nucleic acid and modulate its function. In some embodiments, the inhibitory nucleic acids include CRISPR/Cas9 and guide sequences targeting CX3CL1, antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are those with sequences listed in Table 1 or commercially available (e.g. siRNA ID s12631, siRNA ID s12630, siRNA ID s12629, or siRNA ID 226987 from Thermo Fisher Scientific).

TABLE 1

Sequences of siRNAs targeting mouse CX3CL1.

| Unique Identifer | Sequence of core sense strand (5'-3') | SEQ ID NO: | Sequence of core antisense strand (5'-3') | SEQ ID NO: |
|---|---|---|---|---|
| siRNA_0001 | CCGCGAGUGACUACUAGGA | 17 | UCCUAGUAGUCACUCGCGG | 29 |
| siRNA_0002 | CCUCCUGGCCCGCCGAAUU | 18 | AAUUCGGCGGGCCAGGAGG | 30 |
| siRNA_0003 | CACCUCGGCAUGACGAAAU | 19 | AUUUCGUCAUGCCGAGGUG | 31 |
| siRNA_0004 | UGCGAAAUCAUGUGCGACA | 20 | UGUCGCACAUGAUUUCGCA | 32 |
| siRNA_0005 | GUGGCAGUAACUCAUACGU | 21 | ACGAUGAGUUACUGCCAC | 33 |
| siRNA_0006 | GCUUGCGAGAGGGUUUAAA | 22 | UUUAAACCCUCUCGCAAGC | 34 |
| siRNA_0007 | GCUUGAGAGUGCAGAUCGU | 23 | ACGAUCUGCACUCUCAAGC | 35 |
| siRNA_0008 | GGCCACAAACCCAAUUUCA | 24 | UGAAAUUGGGUUUGUGGCC | 36 |

TABLE 1-continued

Sequences of siRNAs targeting mouse CX3CL1.

| Unique Identifer | Sequence of core sense strand (5'-3') | SEQ ID NO: | Sequence of core antisense strand (5'-3') | SEQ ID NO: |
|---|---|---|---|---|
| siRNA_0009 | GUACUUGCAU AGUCAGACA | 25 | UGUCUGACUA UGCAAGUAC | 37 |
| siRNA_0010 | GAAGCCAACC CUUUGUCGA | 26 | UCGACAAAGG GUUGGCUUC | 38 |
| siRNA_0011 | CCCGUCAUCG GACUUUGUU | 27 | AACAAAGUCC GAUGACGGG | 39 |
| siRNA_0012 | GAAUGUGGGC CGUAACAAU | 28 | AUUGUUACGG CCCACAUUC | 40 |

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin"

structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 rnM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; Fluiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; Ørom et al., Gene. 2006 May 10; 372( ):137-41). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH,~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O— P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH3, F, OCN, OCH3 OCH3, OCH3 O(CH2)n CH3, O(CH2)n NH2 or O(CH2)n CH3 where n is from 1 to about 10; Ci to C10 lower alkyl, alkoxyalkoxy, substituted lower alkyl, alkaryl or aralkyl; C1; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098;

5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jensen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

CRISPR Gene Editing Complexes

The present methods include the use of CRISPR gene editing complexes. The methods can include the use of expression vectors for in vivo transfection and expression of a Cas9 protein and suitable guide RNAs targeting CX3CL1. Alternatively or in addition, the methods can include the use of purified Cas9 proteins complexed with suitable guide RNAs targeting CX3CL1.

Nucleic Acids Encoding a CRISPR CX3CL1Gene Editing Complex

The present methods include the delivery of nucleic acids encoding a CRISPR CX3CL1 gene editing complex. The gene editing complex includes a Cas9 editing enzyme and one or more guide RNAs directing the editing enzyme to CX3CL1

Guide RNAs Directing the Editing Enzyme to CX3CL1

The gene editing complex also includes guide RNAs directing the editing enzyme to CX3CL1, i.e., comprising a sequence that is complementary to the sequence of a nucleic acid encoding CX3CL1, and that include a PAM sequence that is targetable by the co-administered Cas9 editing enzyme. In some embodiments, the precursor sequence is targeted by the guide RNA., i.e., comprising a sequence that is complementary to the sequence of a nucleic acid encoding CX3CL1. In some embodiments, the precursor sequence is targeted by the guide RNA.

Exemplary CX3CL1 target sequences are shown herein.

Cas9 from *S. pyogenes* or other species can also be used, including those shown in the following Table. Suitable target sequences for use with those Cas9s can readily be determined using known methods.

Additional Cas9s from Various Species

| Species/Variant of Cas9 | PAM Sequence |
| --- | --- |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| *Streptococcus thermophilus* (ST) | NNAGAAW |
| *Treponema denticola* (TD) | NAAAAC |
| *Streptococcus pyogenes* (SP); SpCas9 | NGG |
| *Staphylococcus aureus* (SA); SaCas9 | NNGRRT or NNGRR(N) |
| *Neisseria meningitidis* (NM) | NNNNGATT |

Cas9 Editing Enzymes

The methods include the delivery of Cas9 editing enzymes to the cancer cells. The editing enzymes can include one or more of SpCas9 D1135E variant; SpCas9 VRER variant; SpCas9 EQR variant; SpCas9 VQR variant; *Streptococcus thermophilus* (ST) Cas9 (StCas9); *Treponema denticola* (TD) (TdCas9); *Streptococcus pyogenes* (SP) (SpCas9); *Staphylococcus aureus* (SA) Cas9 (SaCas9); or *Neisseria meningitidis* (NM) Cas9 (NmCas9), as well as variants thereof that are at least 80%, 85%, 90%, 95%, 99% or 100% identical thereto that retain at least one function of the parent case, e.g., the ability to complex with a gRNA, bind to target DNA specified by the gRNA, and alter the sequence of the target DNA.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared.

When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

The PAM sequences of these Cas9s are listed in Table D, above. The sequences of the Cas9s are known in the art; see, e.g., Kleinstiver et al., Nature. 2015 Jul. 23; 523(7561): 481-485; WO 2016/141224; U.S. Pat. No. 9,512,446; US-2014-0295557; WO 2014/204578; and WO 2014/144761. The methods can also include the use of the other previously described variants of the SpCas9 platform (e.g., truncated sgRNAs (Tsai et al., Nat Biotechnol 33, 187-197 (2015); Fu et al., Nat Biotechnol 32, 279-284 (2014)), nickase mutations (Mali et al., Nat Biotechnol 31, 833-838 (2013); Ran et al., Cell 154, 1380-1389 (2013)), FokI-dCas9 fusions (Guilinger et al., Nat Biotechnol 32, 577-582 (2014); Tsai et al., Nat Biotechnol 32, 569-576 (2014); WO2014144288).

The SpCas9 wild type sequence is as follows:

(SEQ ID NO: 41)
MDKKYSIGLDIGTNSVGWAVITDEYKVPSKKFKVLGNTDRHSIKKNLI

GALLFDSGETAEATRLKRTARRRYTRRKNRICYLQEIFSNEMAKVDDS

FFHRLEESFLVEEDKKHERHPIFGNIVDEVAYHEKYPTIYHLRKKLVD

STDKADLRLIYLALAHMIKFRGHFLIEGDLNPDNSDVDKLFIQLVQTY

NQLFEENPINASGVDAKAILSARLSKSRRLENLIAQLPGEKKNGLFGN

LIALSLGLTPNFKSNFDLAEDAKLQLSKDTYDDDLDNLLAQIGDQYAD

LFLAAKNLSDAILLSDILRVNTEITKAPLSASMIKRYDEHHQDLTLLK

ALVRQQLPEKYKEIFFDQSKNGYAGYIDGGASQEEFYKFIKPILEKMD

GTEELLVKLNREDLLRKQRTFDNGSIPHQIHLGELHAILRRQEDFYPF

LKDNREKIEKILTFRIPYYVGPLARGNSRFAWMTRKSEETITPWNFEE

VVDKGASAQSFIERMTNFDKNLPNEKVLPKHSLLYEYFTVYNELTKVK

YVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLT

LFEDREMIEERLKTYAHLFDDKVMKQLKRRRYTGWGRLSRKLINGIRD

KQSGKTILDFLKSDGFANRNFMQLIHDDSLTFKEDIQKAQVSGQGDSL

HEHIANLAGSPAIKKGILQTVKVVDELVKVMGRHKPENIVIEMARENQ

TTQKGQKNSRERMKRIEEGIKELGSQILKEHPVENTQLQNEKLYLYYL

QNGRDMYVDQELDINRLSDYDVDHIVPQSFLKDDSIDNKVLTRSDKNR

GKSDNVPSEEVVKKMKNYWRQLLNAKLITQRKFDNLTKAERGGLSELD

KAGFIKRQLVETRQITKHVAQILDSRMNTKYDENDKLIREVKVITLKS

KLVSDFRKDFQFYKVREINNYHHAHDAYLNAVVGTALIKKYPKLESEF

VYGDYKVYDVRKMIAKSEQEIGKATAKYFFYSNIMNFFKTEITLANGE

IRKRPLIETNGETGEIVWDKGRDFATVRKVLSMPQVNIVKKTEVQTGG

FSKESILPKRNSDKLIARKKDWDPKKYGGFDSPTVAYSVLVVAKVEKG

KSKKLKSVKELLGITIMERSSFEKNPIDFLEAKGYKEVKKDLIIKLPK

YSLFELENGRKRMLASAGELQKGNELALPSKYVNFLYLASHYEKLKGS

PEDNEQKQLFVEQHKHYLDEIIEQISEFSKRVILADANLDKVLSAYNK

HRDKPIREQAENIIHLFTLTNLGAPAAFKYFDTTIDRKRYTSTKEVLD

ATLIHQSITGLYETRIDLSQLGGD

The SaCas9 wild type sequence is as follows:

(SEQ ID NO: 42)
MKRNYILGLDIGITSVGYGIIDYETRDVIDAGVRLFKEANVENNEGRR

SKRGARRLKRRRRHRIQRVKKLLFDYNLLTDHSELSGINPYEARVKGL

SQKLSEEEFSAALLHLAKRRGVHNVNEVEEDTGNELSTKEQISRNSKA

LEEKYVAELQLERLKKDGEVRGSINRFKTSDYVKEAKQLLKVQKAYHQ

LDQSFIDTYIDLLETRRTYYEGPGEGSPFGWKDIKEWYEMLMGHCTYF

PEELRSVKYAYNADLYNALNDLNNLVITRDENEKLEYYEKFQIIENVF

KQKKKPTLKQIAKEILVNEEDIKGYRVTSTGKPEFTNLKVYHDIKDIT

ARKEIIENAELLDQIAKILTIYQSSEDIQEELTNLNSELTQEEIEQIS

NLKGYTGTHNLSLKAINLILDELWHTNDNQIAIFNRLKLVPKKVDLSQ

QKEIPTTLVDDFILSPVVKRSFIQSIKVINAIIKKYGLPNDIIIELAR

EKNSKDAQKMINEMQKRNRQTNERIEEIIRTTGKENAKYLIEKIKLHD

MQEGKCLYSLEAIPLEDLLNNPFNYEVDHIIPRSVSFDNSFNNKVLVK

QEENSKKGNRTPFQYLSSSDSKISYETFKKHILNLAKGKGRISKTKKE

YLLEERDINRFSVQKDFINRNLVDTRYATRGLMNLLRSYFRVNNLDVK

VKSINGGFTSFLRRKWKFKKERNKGYKHHAEDALIIANADFIFKEWKK

LDKAKKVMENQMFEEKQAESMPEIETEQEYKEIFITPHQIKHIKDFKD

YKYSHRVDKKPNRELINDTLYSTRKDDKGNTLIVNNLNGLYDKDNDKL

KKLINKSPEKLLMYHHDPQTYQKLKLIMEQYGDEKNPLYKYYEETGNY

LTKYSKKDNGPVIKKIKYYGNKLNAHLDITDDYPNSRNKVVKLSLKPY

RFDVYLDNGVYKFVTVKNLDVIKKENYYEVNSKCYEEAKKLKKISNQA

EFIASFYNNDLIKINGELYRVIGVNNDLLNRIEVNMIDITYREYLENM

NDKRPPRIIKTIASKTQSIKKYSTDILGNLYEVKSKKHPQIIKKG

See also Hou, Z. et al. Efficient genome engineering in human pluripotent stem cells using Cas9 from *Neisseria meningitidis*. Proc Natl Acad Sci USA (2013); Fonfara, I. et al. Phylogeny of Cas9 determines functional exchangeability of dual-RNA and Cas9 among orthologous type II CRISPR-Cas systems. Nucleic Acids Res 42, 2577-2590 (2014); Esvelt, K. M. et al. Orthogonal Cas9 proteins for RNA-guided gene regulation and editing. Nat Methods 10, 1116-1121 (2013); Cong, L. et al. Multiplex genome engineering using CRISPR/Cas systems. Science 339, 819-823

(2013); Horvath, P. et al. Diversity, activity, and evolution of CRISPR loci in *Streptococcus thermophilus*. J Bacteriol 190, 1401-1412 (2008).

As noted above, the Cas9 can be delivered as a purified protein (e.g., a recombinantly produced purified protein, prefolded and optionally complexed with the sgRNA) or as a nucleic acid encoding the Cas9, e.g., an expression construct. Purified Cas9 proteins can be produced using methods known in the art, e.g., expressed in prokaryotic or eukaryotic cells and purified using standard methodology. See, e.g., Liang et al., Journal of Biotechnology 208:44-53 (2015); Kim et al., Genome Res. 2014 June; 24(6): 1012-1019. Efficiency of protein delivery can be enhanced, e.g., using electroporation (see, e.g., Wang et al., Journal of Genetics and Genomics 43(5):319-327 (2016)); cationic or lipophilic carriers (see, e.g., Yu et al., Biotechnol Lett. 2016; 38: 919-929; Zuris et al., Nat Biotechnol. 33(1):73-80 (2015)); or even lentiviral packaging particles (see, e.g., Choi et al., Gene Therapy 23, 627-633 (2016)).

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy,* 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by KrUtzfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

Gene Therapy

The nucleic acids described herein, e.g., nucleic acids encoding an inhibitory nucleic as described herein, can be incorporated into a gene construct to be used as a part of a gene therapy protocol. The methods can include the use of targeted expression vectors for in vivo transfection and expression of the inhibitory nucleic acids in particular cell types, especially endothelial cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology,* Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22): 1896-905 (2000); or Tam et al., Gene Ther. 7(21):1867-74 (2000).

In some embodiments, a gene encoding a compound described herein is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Endothelial Cell Delivery Vehicles

The compositions described herein include vehicles or targeting moieties that deliver the CX3CL1 inhibitors to endothelial cells; in some embodiments, the vehicles are lipid nanoparticles. Lipid nanoparticle (LNP) refers to any lipid composition that can be used to deliver a therapeutic product, preferably siRNAs or an siRNA, including, but not limited to, liposomes or vesicles, wherein an aqueous volume is encapsulated by amphipathic lipid bilayers (i.e. single; unilamellar or multiple; multilamellar), or where the lipids coat an interior comprising a therapeutic product, or lipid aggregates or micelles, wherein the lipid encapsulated therapeutic product is contained within a relatively disordered lipid mixture.

As used herein, "lipid encapsulated" can refer to a lipid formulation which provides a therapeutic product with full encapsulation, partial encapsulation, or both.

The term "lipid" refers to a group of organic compounds that are esters of fatty acids and are characterized by being insoluble in water but soluble in many organic solvents. They are usually divided in at least three classes: (1) "simple lipids" which include fats and oils as well as waxes; (2) "compound lipids" which include phospholipids and glycolipids; (3) "derived lipids" such as steroids.

The term "amphipathic lipid" refers, in part, to any suitable material wherein the hydrophobic portion of the lipid material orients into a hydrophobic phase, while a hydrophilic portion orients toward the aqueous phase. Amphipathic lipids are usually the major component of lipid nanoparticles. Hydrophilic characteristics derive from the presence of polar or charged groups such as carbohydrates, phosphate, carboxylic, sulfate, amino, sulfhydryl, amine, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleryl phosphatidylcholine, lysophosphatidylcholine, lysophosphatidylethanolamine, dipalmitoylphosphatidylcholine, dioleoylphospbatidylcholine, dstearoylphosphatidylcholine or dilinoleoylphosphatidylcholine. Other compounds lacking in phosphorus, such as sphingolipid, giycosphingolipid families, diacylglycerols and S-acyloxyacids, are also within the group designated as amphipathic lipids. Additionally, the amphipathic lipid described above can be mixed with other lipids including triglycerides and sterols.

The term "neutral lipid" refers to any of a number of lipid species that exist either in an uncharged or neutral zwitterionic form at a selected pH. At physiological H, such lipids include, for example, diacylphosphatidylcholine, diacylphosphatidyletbanolamine, ceramide, sphingomyelin, cephalin, cholesterol, cerebrosides and diacylglycerols.

The term "noncationic lipid" refers to any neutral lipid as described above as well as anionic lipids. Useful noncationic lipids include, for example, distearoylphos-phatidylcholine (DSPC), dioleoylphosphatidylcholine (DOPC), dipalmitoylphosphatidylcholine (OPEC), dioleoylphospbatidylglycerol (DOPG), MRL-MIS-00024 dipahnitoylphosphatidylglycerol (DPPG), dioleoyl-phosphatidyle-thanolamine (DOPE), palmitoyloleoylphosphatidy lcholine (POPC), palmitoylolmyl-phosphati dylethanolamine (POPE) and dioleoyl-phosphatidylethanolamine 4-(4-maleimidomethyl)cyelohexane-1-carboxylate (DOPE-teal), dipahnitoyl phosphatidyl ethanolamine (DPPE), dimyristoylphosphoetbanolamine (DMPE), distearoyl-phosphatidylethanolamine (DSPE), 16-O-monomethyl PE, 16-0dimethyl PE, 18-1-trans PE, 1-stearoyl-2-oleoyl-phosphatidyethanolamine (SOPS), and 1,2-dielaidoyl-sn-glycero-3-phophoethanolamine (transDOPE).

The term "anionic lipid" refers to any lipid that is negatively charged at physiological pH. These lipids include, but are not limited to, phosphatidylglycerol, car-diolipin, diacylphosphatidylserine, diacylphosphatidic acid, N-dodecanoyl phosphatidylethanolamines, N-succinyl phosphatidylethanolamines, N-glutarylphosphatidylethanolarnines, lysylphosphatidylglycerols, palmitoyloleyolphos-phatidylg-lyeerol (POPG), and other anionic modifying groups joined to neutral lipids.

The term "cationic lipid" refers to any of a number of lipid species which carry a net positive charge at a selective pH, such as physiological pH. Such lipids include, but are not limited to, N,N-dioleyl-N,N-dimethylammonium chloride ("DODAC"); N~(2,3dioleyloxy)propyl)-N,N,Ntrimethylammonium chloride ("DOTMA"); N,NdistearylN,N-dim-ethylammonium bromide fDDAB"); N-(2,3dioleyloxy) propyl)-N,N,N-trimethylamntonium chloride ("DODAP"); 3-(N—(N,N-dimethylaminoethane)-carbam-oyl)cholesterol (DC-Chol") and N-(1,2-dimyristyloxyprop-3-yl)-N,N-dimethyl-N-hydmxyethyl ammonium bromide ("DMRIE"). Additionally, a number of commercial preparations of cationic lipids are available which can be used in the present invention. These include, for example, LIPOFECTIN® (commercially available cationic lipid nanoparticles comprising DOTMA and 1,2dioleoyl-sn-3-phosphoethanolamine ("DOPE"), from GIBCOBRL, Grand Island, N.Y, USA); LIPOFECTAMINE® (commercially available cationic lipid nanoparticles comprising N-(1-(2,3dioleyloxy) propyl)N-(2-(sperminecarboxamido)ethyl)-N,N-dimethylammonium trifluoroacetate ("DOSPA') and ("DOPE"), from (3IBCOBRL); and TRANSFECTAM® (commercially available cationic lipids comprising diocmdecylamidoglycyl carboxy spermine ("DOGS") in ethanol from Promega Corp., Madison, Wis., USA). The following lipids are cationic and have a positive charge at below physiological pH: DODAP, DODMA, DMDMA, 1,2-DiLinoleyloxy-N,N-dimethylaminopropane (DLinDMA), 4-(2,2-diocta-9,12-di-enyl-[1,3]dioxolan-4-ylmethyl)-dimethylaraine, DLinKDMA (WO 2009/132131 A1), DLin-K-C2-DMA (WO2010/042877), DLin-M-C3-DMA (WO2010/146740 and/or WO2010/105209), 2~{4-[(3p)-cholest-5-en-3-yloxy]butoxy}-NSN-dimethyl-3-[(9Z, 12Z)-octadeca-9, 12-dienlyloxy 1]propan-1-amine) (CLinDMA), and the like. M L-MIS-00024

In addition to cationic and non-cationic lipids, the lipid nanoparticles of the present invention may comprise bilayer stabilizing component (BSC) such as an ATTA-lipid or a PEG-lipid, such as PEG coupled to dialkyloxypropyls (PEG-DA A) as described in, e.g., WO 05/026372, PEG coupled to diacylglycerol (PEG-DAG) as described in, e.g., U.S. Patent Publication Nos. 20030077829 and 2005008689, PEG coupled to dimyristoylglecerol (PEG-DMG) as described in, e.g., Abrams et. al, Molecular Therapy 2010, 18(1), 171, PEG coupled to phosphatidylethanolamine (PE) (PEG-PE), or PEG conjugated to 1,2-Di-O-hexadecyl-sn-glyceride (PEG-DSG), or a mixture thereof (see, U.S. Pat. No. 5,885,613). In one preferred embodiment, the BSC is a conjugated lipid that inhibits aggregation of the lipid nanoparticle.

In certain aspects, the cationic lipid typically comprises from about 2% to about 70%, from about 5% to about 50%, from about 10% to about 45%, from about 20% to about 40%, or from about 30% to about 40% of the total lipid present in said particle. The non-cationic lipid typically comprises from about 5% to about 90%, from about 10% to about 85%, from about 20% to about 80%, from about 30% to about 70%, from about 40% to about 60% or about 48% of the total lipid present in said particle. The PEG-lipid conjugate typically comprises from about 0.5% to about 20%, from about 1.5% to about 18%, from about 4% to about 15%, from about 5% to about 12%, or about 2% of the total lipid present in said particle. The nucleic acid-lipid particles of the present invention may further comprise cholesterol. If present, the cholesterol typically comprises from about 0% to about 10%, about 2% to about 1%, about 10% to about 60%, from about 12% to about 58%, from about 20% to about 55%, or about 48% of the total lipid present in said particle. It will be readily apparent to one of skill in the art that the proportions of the components of the nucleic acid-lipid particles may be varied.

In some embodiments, the nucleic acid to lipid ratios (mass/mass ratios) in a formed nucleic acid-lipid particle will range from about 0.01 to about 0.3. The ratio of the starting materials also falls within this range.

Some exemplary siRNA delivery vehicles targeting endothelial cells in tumors are shown in the following table.

| siRNA delivery carrier | Type of siRNA delivery system | Target | Note (cells used in experiments) |
|---|---|---|---|
| [1]anti-E-selectin-SAINTPEGargs | PEGylated cationic amphiphile SAINT-C18 based lipoplexes | Inflamed primary vascular endothelial cells | Human endothelial cells (HUVEC/HAEC/HHSEC) |
| [1]anti-VCAM-1-SAINTPEGargs | PEGylated cationic amphiphile SAINT-C18 based lipoplexes | Inflamed primary vascular endothelial cells | Human endothelial cells (HUVEC/HAEC/HHSEC) |
| [2]anti-E-selectin-SAINT-O-Somes | Cationic amphiphile SAINT-C18 based lipoplexes | Inflamed primary vascular endothelial cells | Human endothelial cells (HUVEC/HAEC) |

-continued

| siRNA delivery carrier | Type of siRNA delivery system | Target | Note (cells used in experiments) |
|---|---|---|---|
| [2] anti-VCAM-1 SAINT-O-Somes | Cationic amphiphile SAINT-C18 based lipoplexes | Inflamed primary vascular endothelial cells | Human endothelial cells (HUVEC/HAEC) |
| [3] PEG500-CR9C | oligopeptoplexes with PEGylated oligo-D-arginine based cationic peptide | Squamous cell carcinoma | Squamous cell carcinoma 7 (SCC-7) |
| [4] Rpp-nanoplexes | Nanoparticles with PEGylated polyethyleneimine (PEI) and an Arg-Gly-Asp (RGD) peptide (RGD-PEG-PEI) | Activated endothelial cells in tumor vasculature (targeting integrins) | Human endothelial cell (HUVEC), Murine neuroblastoma cell (N2A), Murine endothelial cell (SVR-bag 4) |
| [5] Angiplexes | Anginex targeted PEGylated lipoplexes | Tumor vascular endothelial cells | Human vascular endothelial cell (HUVEC) |
| [6] BR2 | siRNA conjugation with Cell Penetrating Peptide (CPP) | Cancer cells | Human cervical cancer cells (HeLa), Human colon cancer cells (HCT116), Mouse fibroblast cells (NIH3T3), Human keratinocyte cells (HaCat) |
| [7] PLCP | Polycation Liposome-encapsulated Calcium Phosphate nanoparticles (PLCP); CaP/siRNA nanoparticles combined with polycation liposomes (PCLs). | Breast cancer cells | Human breast adenocarcinoma cell lines (MCF-7) |
| [8] RGD-MEND | PEGylated cyclic RGD peptide-equipped lipoplexes | Tumor endothelial cells | Human renal cell carcinomas (OS-RC-2), Murine breast cancer (4T1 cells) |
| [9] PG1.C15 | Modified dendrimer nanoparticles; generation 1 poly (amido amine) dendrimer with $C_{15}$ lipid tails | Tie2 expressing lung endothelial cells | Human microvascular endothelial cell (HMVEC) |
| [9] DG1.C15 | Modified dendrimer nanoparticles; generation 1 poly (propylenimine) dendrimers with $C_{15}$ | Tie2 expressing lung endothelial cells | Human microvascular endothelial cell (HMVEC) |
| [10] 7C1 | polymeric nanoparticle made of polyamines and lipids | endothelial cells | HeLa and HMVEC and bEnd.3 cells |

[1] Leus N.G.J, et al. Effective siRNA delivery to inflamed primary vascular endothelial cells by anti-E-selectin and anti-VCAM-1 PEGylated SAINT-based lipoplexes. International Journal of Pharmaceutics. 2014
[2] Kowalski P.S, et al. Anti-VCAM-1 and Anti-E-selectin SAINT-O-Somes for selective delivery of siRNA into inflammation-activated primary endothelial cells. Molecular Pharmaceutics. 2013
[3] Chung J, et al. Enhanced systemic anti-angiogenic siVEGF delivery using PEGylated oligo-d-arginine. Molecular Pharmaceutics. 2017
[4] Schiffelers RM, et al. Cancer siRNA therapy by tumor selective delivery with ligand-targeted sterically stabilized nanoparticle. Nucleic Acids Research. 2004
[5] Yousefi A, et al. Anginex lipoplexes for delivery of anti-angiogenic siRNA. International Journal of Pharmaceutics. 2014
[6] Lee Y, et al. VEGF siRNA delivery by a cancer-specific cell-penetrating peptide. Journal of Microbiology and Biotechnology. 2017.
[7] Chen J, et al. VEGF siRNA delivered by polycation liposome-encapsulated calcium phosphate nanoparticles for tumor angiogenesis inhibition in breast cancer. International Journal of Nanomedicine. 2017
[8] Hada T, et al. Optimization of a siRNA Carrier Modified with a pH-Sensitive Cationic Lipid and a Cyclic RGD Peptide for Efficiently Targeting Tumor Endothelial Cells. Pharmaceutics. 2015
[9] Khan OF, et al. Dendrimer-Inspired Nanomaterials for the in vivo delivery of siRNA to lung vasculature. Nano letters. 2015
[10] Dahlman et al., In vivo endothelial siRNA delivery using polymeric nanoparticles with low molecular weight. Nature Nanotechnology. 2014

Antibodies

In some embodiments, the methods and compositions described herein can include the use of antibodies that bind to CX3CR1.

The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume 1* (*Springer Protocols*) (Springer; 2nd ed., May 21, 2010); Lo, *Antibody Engineering: Methods and Protocols* (*Methods in Molecular Biology*) (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

The antibody can be coupled to a detectable or imaging agent. Such agents are well known in the art and include paramagnetic agents, bioluminescent or fluorescent labels (e.g., GFP, FITC, rhodamine, or Texas Red), radioactive isotopes, and colorimetric/enzymatic agents (e.g., HRP, B-galactosidase). In a preferred embodiment, the antibody is coupled to a paramagnetic agent, e.g., a paramagnetic nanoparticle, e.g., cross-linked iron oxide (CLIO) nanoparticles; see, e.g., US 20110046004; Josephson et al., Bioconjug. Chem., 10(2):186-91 (1999).

Cell-Penetrating Peptides

In some embodiments, the composition includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, *Cell-Penetrating Peptides: Processes and Applications*, (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, antibodies nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140).

Anti-Angiogenic Therapies

In some embodiments, the methods and compositions described herein can include the use of anti-angiogenic therapies. Anti-angiogenic therapies related to compositions of agents that inhibit angiogenesis or reduce angiogenic-dependent signaling. In some embodiments the compositions contain one or more antibodies that bind VEGF protein and reduce VEGF-dependent signaling. Such antibodies against VEGF include bevacizumab, aflibercept, ramucirumab, sorafenib, sunitinib, regorafenib, pazopanib, axitinib, vandetanib, lenvatinib, or cabozantinib. In other embodiments, the compositions contain one or more antibodies that bind PDGF family of proteins, FGF family of proteins, ANG/TIE2 family of proteins, HG/MET family of proteins, and/or RET family of proteins.

The anti-angiogenic therapies can be administered before, after, or concurrently with (e.g., within 1-3 hours of administration of a dose of) the CX3CL1 inhibitors described herein. When administered at the same time, they can be administered in the same composition or in separate compositions.

Pharmaceutical Compositions and Methods of Administration

The methods described herein include the use of pharmaceutical compositions comprising a CX3CL1 inhibitor, e.g., a composition that reduces CX3CL1 expression or activity in endothelial cells as an active ingredient, alone or in combination with an anti-angiogenic agent.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., Anti-angiogenic agents as known in the art or described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable micropar-ticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Dosage

An "effective amount" is an amount sufficient to effect beneficial or desired results. For example, a therapeutic amount is one that achieves the desired therapeutic effect. This amount can be the same as or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Materials and Methods

The following materials and methods were used in the Examples set forth herein.

Animals $Cx_3cr1^{gfp/gfp}$ mice were originally provided by Dr. Dan R. Littman at the New York University School of Medicine (New York, N.Y.) (51). $Ccr2^{-/-}$ mice were purchased from Jackson Laboratories (Stock number 004999). Homozygous $Cx_3cr1^{gfp/gfp}$ mice were used for the $Cx_3cr1$-deficient model. $Cx_3cr1^{gfp/+}$ mice were obtained by breeding $Cx_3cr1^{gfp/gfp}$ mice with C57BL/6 WT mice. $Cx_3cr1^{gfp/+}$ mice have one $Cx_3cr1$ allele replaced with cDNA encoding Egfp. Mice were 8-10 weeks old.

CRC Cell Preparation

SL4 (67) murine colorectal cancer (CRC) cells were cultured in DMEM/F12 1:1 mixture medium supplemented with 10% fetal bovine serum (FBS), and CT26 (68) murine CRC cells were cultured in RPMI-1640 medium supplemented with 10% FBS prior to implantation. Sub-confluent SL4 or CT26 cells were harvested, washed with phosphate-buffered saline (PBS), and counted. Tumor cell suspension was mixed with Matrigel (Product #354262, Corning, Tewksbury, M A) in a one to one proportion by volume.

Orthotopic CRC and Spontaneous Rectal Tumor Model and Treatment Regimen

For orthotopic CRC model, eight to ten-week-old male C57BL/6J (for SL4 implantation) and BALB/c (for CT26) mice were anesthetized with intraperitoneal injection of ketamine (100 mg/kg) and xylazine (10 mg/kg). Abdominal hair was removed, and a 10 mm mid-line incision was made. The cecum was exteriorized, and $5\times10^5$ cells in 10 µL of PBS/Matrigel complex were injected into the cecal wall between the serosa and mucosa from the serosal side using an insulin syringe with a 27G needle (67, 68). The cecum was returned to the abdominal cavity and the abdominal wall was closed with 5-0 polysorb sutures (Covidien, Dublin, Ireland), followed by skin closure with surgical staples. Tumor size was monitored either by measuring the activity of secreted Gaussia Luciferase (69, 70) or by imaging with ultrasound twice a week. For spontaneous rectal tumor model, conditional Apc knock-out mice were used as described previously (33).

When tumor diameter reached 4 mm, tumor-bearing mice were randomly assigned into different treatment groups and treated accordingly. 40 mg/kg of DC101 (ImClone Systems/Eli Lilly), a monoclonal anti-VEGFR2 antibody, was administrated intraperitoneally every 3 days. Control mice received 40 mg/kg of rat IgG intraperitoneally every 3 days. To deplete neutrophils, 5 mg/kg of anti-Ly6G antibody (BioXcell) was administered intraperitoneally every 3 days. To silence Tie2 mRNA, 1 mg/kg of 7C1-siTie2 was injected intravenously. To silence CX3CL1 mRNA, 1 mg/kg of 7C1-Axo-siCX3CL1 was administered intravenously every 3 days. 5 or 12 days after treatment, mice were sacrificed and tumor samples were taken, measured, weighed and used for further analyses.

Blood Gluc Assay

In order to monitor SL4 tumor size in the orthotopic implantation model, blood Gluc activity was measured as described previously (69, 70). In short, the SL4-Gluc cell line was established by transduction of lentivirus encoding Gluc gene and the cells were implanted orthotopically. Blood was collected from the tumor bearing mice twice a week and blood Gluc activity was measured using a GloMax 96 Microplate Luminometer (Promega, Madison, Wis.).

Ultrasound Imaging

Ultrasound imaging was performed to measure tumor size twice a week until the end of the study using the Vevo 2100 system (VisualSonic Toronto, Canada) with M1350S probe (frequency 40 MHz). Tumor-bearing mice were anesthetized with intraperitoneal injection of ketamine (100 mg/kg) and xylazine (10 mg/kg), and secured to a heated platform. Abdominal hair was removed and the exposed skin was covered with ultrasound gel. The probe was applied to the skin and images were acquired. Tumor tissue in abdominal cavity was identified as a low echoic mass on ultrasound image. The long diameter (LD) and short diameter (SD) were measured. Tumor volume was calculated using the following formula: Tumor volume=(LD×SD$^2$)/2.

Statistics

The measured values were presented as mean±standard error of mean (SEM). Data are representative of three independent experiments unless otherwise stated. Comparison between groups was made using ANOVA with Holm-Sidak post-hoc test. Two-tailed t tests were used between data comparing only two groups. Statistical significance was considered significant when P<0.05.

Study Approval

All animal procedures followed Public Health Service Policy on Humane Care of Laboratory Animals guidelines and were approved by the Massachusetts General Hospital Institutional Animal Care and Use Committee.

Immunohistochemistry and Quantification

For hypoxia analysis, mice were injected with 60 mg/kg of pimonidazole 1 h before tumor removal. Tumor tissue samples were harvested and fixed for 2 hours in 4% formaldehyde. After fixation, tissue was incubated in 30% sucrose solution overnight at 4° C. Then, samples were embedded in OCT compound (Tissue-Tek) and kept at −80° C. Frozen blocks were cut at 20 µm thickness, and stained for CD31 (1:100, BD Biosciences) or fractalkine (CX3CL1) (1:100, Abcam), and counterstained with DAPI (Vector Labs) according to the manufacture's protocol. Whole tumor tissue images were taken using an Olympus FV1000 confocal laser-scanning microscope. Fractalkine positive area and hypoxic area were quantified using custom codes in MATLAB (The MathWorks). For vascular analysis, vessels were skeletonized and segmented using a custom, semi-automated tracing program developed in MATLAB (The MathWorks), allowing the removal of structures under 30 pixels and regions of auto-fluorescence.

Clinical Specimens Immunohistochemistry

We obtained biopsies of rectal carcinomas from patients before and 12 days after bevacizumab treatment (75, 76). Formalin-fixed paraffin-embedded rectal carcinoma biopsy samples were cut at 5-µn thickness. The sections were stained with anti-fractalkine (CX3CL1) antibody (R&D Systems) according to the manufacture's protocol. Fractalkine positive area was quantified using custom codes in MATLAB (The MathWorks).

Flow Cytometry

Flow cytometry was performed as described previously (77). Briefly, tumor tissues were resected, chopped, and digested in a 37° C. incubator for 1 hour with culture medium containing collagenase type 1A (1.5 mg/mL), hyaluronidase (1.5 mg/mL), and DNase (2 mg/ml). Digested tissue was filtered through 70-µm cell strainers. The single cell suspensions were incubated with a rat anti-mouse CD16/CD32 antibody and then were stained with the following monoclonal antibodies according to the manufacturer's protocols: CD45 (clone 30-F11), B220 (clone RA3-6B2), CD49b (clone DX5), CD90 (clone 53-2.1), Ter119 (clone TER-119), I-A/I-E (clone M5/114.15.2), NK1.1 (clone PK136), CD4 (clone RM4-5), CD8 (clone 53-6.7), Granzyme B (clone NGZB), PD-1 (clone J43), FoxP3 (clone FJK-16s), CD25 (clone PC61), CD11b (clone M1/70), F4/80 (clone BM8), CD11c (clone HL3), Gr1 (clone RB6-8C5), Ly6C (clone HK1.4), Ly6G (clone 1A8) (BD Biosciences). 7-Amino-actinomycin D (7AAD) reagent (eBioscience) was added to the stained tubes just before running the flow cytometer. We defined CD45$^+$ Lin$^-$ F4/80$^-$ CD11c$^-$ CD11b$^+$ Ly6G$^-$ (Ly6C$^{low}$ or Ly6C$^{high}$) population as Ly6C$^{low}$ or Ly6C$^{high}$ monocytes. We defined CD45$^+$ Lin$^-$ F4/80$^-$ CD11c$^-$ CD11b$^+$ Ly6G$^+$ population as neutrophils. After staining, flow cytometry was performed using an LSRII flow cytometer (Becton Dickinson, Franklin Lakes, N.J.), and the data were analyzed with FlowJo software (Tree Star, Ashland, Oreg.).

Gene Expression Polymerase Chain Reaction (PCR) Array

Total RNA was extracted from each sorted subset of myeloid cells by RNeasy Mini Kit (QIAGEN, Venlo, Netherlands). Relative gene expression was determined using RT$^2$ Profiler PCR Arrays system (QIAGEN, Venlo, Netherlands) on a Mx3000P qPCR System (Stratagene, La Jolla, Calif.). The pre-made pathway-focused arrays used (mouse genes) were "Chemokines & Receptors (PAMM022Z)" and "T-Cell & B-Cell Activation (PAMM053Z)".

Quantitative Reverse-Transcription PCR

Total RNA was extracted from resected tumor tissues by RNeasy Mini Kit (QIAGEN, Venlo, Netherlands). cDNA products were synthesized by iScript reverse transcription supermix (Bio-Rad Laboratories, Hercules, Calif.). Relative gene expressions of Bv8 (forward primer: GCCCCGC-TACTGCTACTTC; SEQ ID NO:1); reverse primer: CCCCGTGCAGACACTAACTTT; SEQ ID NO:2), Tie2 (forward primer: GAGTCAGCTTGCTCCTTTATGG; SEQ ID NO:3; reverse primer: AGACACAAGAGGTAGG-GAATTGA; SEQ ID NO:4), and Cx3cl1 (forward primer: CGCGTTCTTCCATTTGTGTA; SEQ ID NO:5; reverse primer: CTGTGTCGTCTCCAGGACAA; SEQ ID NO:6) were determined using the specific primers, Real-Time SYBR Green PCR master mix (Applied Biosystems, Branchburg, N.J.), and a Mx3000P qPCR System (Stratagene, La Jolla, Calif.). All values were normalized by GAPDH as a reference gene.

Western Blot Analysis

Serum-starved mouse primary lung microvascular endothelial cells (LMVECs) were treated with control buffer or recombinant VEGF-A protein (50 ng/ml) in the absence or presence of 2 µg/ml DC101 for 12 hrs. After treatment, the cells were lysed with RIPA buffer (Thermo Scientific) with protease and phosphatase inhibitors. Total protein concentration was determined by the Pierce BCA protein assay kit (Thermo Scientific). Each lane was loaded with equal amounts of total protein. Blots were probed with goat anti-mouse CX3CL1 antibody (R&D Systems) and donkey anti-goat IgG-HRP (Santa Cruz Biotechnology) antibody, and developed with Amersham ECL Prime Western blotting detection reagents (GE-Healthcare Life Sciences). Each tumor sample was homogenized directly in lysis buffer for protein extraction. 30 µg of denatured protein per sample was loaded on 10% SDS-polyacrylamide gels. Membranes were blotted with antibodies against CX3CL1 (R&D Systems) and GAPDH (Cell Signaling). Antibodies were diluted 1:1000.

Protein Expression Measurement

For multiplex array, each tumor sample was homogenized directly in lysis buffer for protein extraction. 2 µg/µl of sample was used for the pre-made inflammatory multiple cytokines protein array (V-PLEX Proinflammatory Panel 1 mouse kit, Cat. #K15048D). To measure other cytokine/chemokine expression levels, we used mouse Quantikine ELISA kits for TGF-β1, CXCL2, CXCL5, CX3CL1, and CCL2 (R&D systems) following the manufacturer's protocols. Ly6C$^{low}$ monocytes, Ly6C$^{high}$ monocytes, and neutrophils were sorted (FACS Aria) from SL4 tumor-bearing C57BL/6 mice treated with DC101. The sorted cells were cultured for 24 h, and their conditioned media were collected for cytokine/chemokine level measurement according to the manufacturer's protocols.

In Vitro Migration Assay

Ly6C$^{low}$ monocytes, Ly6C$^{high}$ monocytes, and neutrophils were sorted (FACS Aria) from SL4 tumor-bearing C57BL/6 mice treated with DC101. 2×10$^4$ neutrophils were seeded on 3 µm pore size PET membrane transwell inserts (Corning) in the upper chamber. The lower chamber included either 8×10$^4$ Ly6C$^{low}$ monocytes, Ly6C$^{high}$ monocytes, or their conditioned media with or without neutralizing antibodies for the chemokine/chemokine receptor. Anti-CXCR2 antibody (10 µg/ml), anti-CXCL1 antibody (2 µg/ml), anti-CXCL2 antibody (2 µg/ml), and anti-CXCL5 antibody (2 µg/ml) were used (R&D systems). After 5 h, non-migrated cells were removed with a cotton tip and the membranes were fixed and stained with Protocol HEMA 3 staining solutions (Fisher Scientific) to identify cells that had migrated to the lower surface of the membrane. The number of migrated cells was determined using 200× magnification.

CFSE T Cell Proliferation Assay

CD8$^+$ T cells and CD4$^+$ T cells were sorted (FACS Aria) from spleens of C57BL/6 wild-type mice. The sorted CD8$^+$ and CD4$^+$ T cells were incubated with CellTrace CFSE (5 µM) at 37° C. for 15 min and washed with pre-warmed RPMI-1640 media with 5% FBS. CFSE-labeled CD8$^+$ or CD4$^+$ T cells (2×10$^4$ cells) were co-cultured with Ly6C$^{low}$ monocytes, Ly6C$^{high}$ monocytes, or neutrophils (1:2 ratio) for 2 days with or without anti-IL-10 neutralizing antibody (10 µg/ml, Clone JESS-2A5) in the presence of anti-CD28 antibody (2 µg/ml, clone 37.51) in a 96 well plate pre-coated with anti-CD3e antibody (clone 145-2C11). Ly6C$^{low}$ monocytes, Ly6C$^{high}$ monocytes, and neutrophils were sorted (FACS Aria) from SL4 tumor-bearing C57BL/6 mice treated with DC101. CFSE levels were assessed in CD8$^+$ and CD4$^+$ T cells by flow cytometry using an LSRII flow cytometer.

Adoptive Transfer

For the rescue effect of adoptive transfer, Ly6C$^{low}$ monocytes and Ly6C$^{high}$ monocytes were sorted (FACS Aria) from SL4 tumor-bearing C57BL/6 wild-type or Cx$_3$cr1$^{-/-}$ mice treated with DC101. 1×10$^6$ of sorted Ly6C$^{low}$ monocytes (i.e., WT Ly6C$^{low}$ monocytes or CX3CR1-deficient Ly6C$^{low}$ monocytes) or WT Ly6C$^{high}$ monocytes were intravenously injected twice a week into Cx$_3$cr1$^{-/-}$ mice treated with DC101 from the beginning of DC101 treatment. For intravital microscopy, Ly6C$^{low}$ monocytes were sorted (FACS Aria) from SL4 tumor-bearing C57BL/6 wild-type or Cx$_3$cr1$^{-/-}$ mice treated with DC101. 1×10$^6$ of sorted wild-type Ly6C$^{low}$ monocytes (WT Ly6C$^{low}$ monocytes) and CX3CR1-deficient Ly6C$^{low}$ monocytes (KO Ly6C$^{low}$ monocytes) were fluorescently labeled with Vybrant DiO cell-labeling solution (Thermo Scientific) according to the manufacturer's protocol, and then intravenously injected into C57BL/6 wild-type mice treated with DC101.

Cecum Window

Eight to ten-week-old male mice were anesthetized with intraperitoneal injection of ketamine (100 mg/kg) and xylazine (10 mg/kg). Abdominal hair was removed, and 10 mm mid-line incision was made to expose the cecum. A glass coverslip was put in a metal ring and fixed with a coverslip holder, and the metal ring was glued to the cecum. Using a purse-string suture (Ethicon, Somerville, N.J.), the abdominal wall and skin were placed in the side groove of the metal ring, and the purse-string suture loop was tightened.

Optical System and In Vivo CRC Imaging

The imaging platform was a previously described custom-built video-rate multi-photon fluorescence microscope (78). The system acquired three-color images (512×512 pixels) at 30 frames per second. The images are displayed in real time on a computer monitor and streamed to a hard disk. The custom data acquisition program can also display and record images averaged over an arbitrary number of consecutive frames in real time. A three-axis translation stage was used to move the mouse. To visualize the blood vessels, 100 µl of tetramethylrhodamine-isothiocyanate (TRITC)-Dextran (5 mg/ml) was injected intravenously.

Cell Counting and Cellular Perfusion Rate In Vivo

To determine the number of CX3CR1$^+$ cells and adoptively transferred Ly6C$^{low}$ monocytes, images were acquired at arbitrarily chosen sites with a FOV of 512 µm each. The image acquisition took approximately 1 minute at each site. The average number of cells was counted and divided by the image area (i.e., 512 µm×512 µm) to calculate the cell density per 1 mm$^2$ in area of tissue. The number of flowing (at a speed of >0.2 mm/s), rolling (15-50 µm/s) and crawling (<15 µm/s) cells in the blood vessels was counted from the acquired video-rate movies. The cellular perfusion rate, or flux, was defined as the total number of moving cells per unit area per unit time (i.e., divided by the recording time period).

Synthesis and In Vitro Screening of siRNA

Twelve siRNAs with the lowest predicted off-target potentials and 100% homology with mouse CX3CL1 gene sequence NM_009142.3 were selected for synthesis and screening. Single-strand RNAs were produced and annealed at Axolabs GmbH and used as duplexes. Mouse primary lung microvascular endothelial cells (LMVECs) were transfected with siRNA by using Lipofectamine 2000 reagent (Thermo Scientific) according to the manufacturer's protocol at 0.1 nM and 10 nM concentrations. CX3CL1 mRNA levels were quantified 24 hours after transfection by quantitative RT-PCR and normalized to GAPDH mRNA. Duplexes showing best knockdown at both concentrations (indicated by red box in FIG. 7B) were selected for 6-point dose-response ranging from 6 pM up to 20 nM. The best duplex with the sequence 5'-gcuuGcGAGAGG-GuuuAAAdTsdT-3' (sense; SEQ ID NO:7) and 5'-UUuAAACCCUCUCGcAAGCdTsdT-3' (anti-sense; SEQ ID NO:8) was selected for large-scale synthesis, nanoparticle formulation, and subsequent in vivo work. Lower case represents 2'-O-methyl modification. These modifications protect siRNA from endonucleolytic degradation and repress potential immune-stimulatory properties of the siRNA, which are crucial for in vivo applications. The sulfur modification in dTsdT residue protects the oligonucleotide from 3'-5'-exonucleolytic degradation. Also, siRNA against CX3CL1 from a recent publication (Moran et al., 2014) was used for the knockdown efficiency comparison with the following sequence: 5'-GCCGCGUUCUUCCAUU-3' (sense; SEQ ID NO:9) and 5'-ACAAAUGGAAGAACGC-3' (anti-sense; SEQ ID NO:10). For silencing Tie2 (siTIE2), we used a duplex with the following sequence: 5'-GAAGAuGcAGuGAuuuAcAdTsdT-3' (sense; SEQ ID NO:11) and 5'-UGuAAAUcACUGcAUCUUCdTsdT-3' (anti-sense; SEQ ID NO:12). For the control siRNA against Luciferase (siLUC), we used a duplex with the following sequence: 5'-cuuAcGcuGAGuAcuucGAdTsdT-3' (sense; SEQ ID NO:13) and 5'-UCGAAGuA-CUcAGCGuAAGdTsdT-3' (anti-sense; SEQ ID NO:14).

siRNA Formulation into 7C1 Nanoparticles

Purified 7C1 nanoparticles were synthesized and formulated as previously described (79). Specifically, polyethyleneimine with a number molecular weight of 600 (PEI$_{600}$, Sigma Aldrich) was combined with 200 proof anhydrous ethanol (Koptec) and an epoxide-terminated $C_{15}$ lipid at a lipid:PEI molar ratio equal to 14:1. The mixture was heated at 90° C. for 48 hours before purification was performed with a silica column as previously described (79). To formulate nanoparticles, purified 7C1 was combined with 200 proof ethanol and (1,2-dimyristoyl-sn-glycero-3-phospho-ethanolamine-N4methoxy(polyethylene glycol)-20001 (Avanti Polar Lipids) at a 7C1:lipid-PEG molar ratio equal to 4:1 in a glass syringe. siRNA was dissolved in pH 3 10 mM citrate solution (Teknova) in a separate syringe. The two syringes were connected to a syringe pump and the fluid was pushed through a microfluidic device as previously described (80). The resulting nanoparticles were dialyzed in 1×PBS and sterilized using a 0.22 μm poly(ether sulfone) syringe filter (Genesee Scientific).

Nanoparticle Characterization

Nanoparticle size and structure was analyzed by dynamic light scattering (DLS) (Zetasizer NanoZS, Malvern Instruments) or cryogenic transmission electron microscopy (cryo-TEM) as previously described (79). DLS samples were measured in sterile 1×PBS at an approximate siRNA concentration of 1.0-3.0 μg/mL. Cryo-transmission electron microscopy (TEM) samples were prepared in a controlled environment vitrification system at 25° C. and ~100% relative humidity.

Example 1. Anti-VEGFR2 Therapy Induces Accumulation of Monocytes and Neutrophils in CRCs FACs based assays were performed using murine CRC models and rectal tumors in conditional Apc mutant mice to quantify how accumulation of monocytes near tumors is altered when mice or tumors are treated with anti-VEGF therapy.

Results

To examine the role of the immune microenvironment in CRCs, we utilized two syngeneic murine CRC models—SL4 and CT26—orthotopically implanted in C57BL/6 and BALB/c mice, respectively. We also studied spontaneous rectal tumors in conditional Apc mutant mice (33). We used DC101, a monoclonal antibody against VEGF receptor 2 (VEGFR2), to inhibit angiogenesis (34). We observed vessel regression and increased hypoxia on Day 5 and 12 after DC101 treatment compared to the control, while there were no observable changes in MVD or hypoxia on Day 2 (FIGS. 9A-9D). Interestingly, there were differences in responses to DC101 between the two orthotopic CRC models with SL4 being more sensitive than CT26 to anti-angiogenic therapy. After DC101 monotherapy, the SL4 tumor size was ~40% of that of the control, while CT26 tumor size was ~70% (FIGS. 1A and 1B).

Figure 10A:
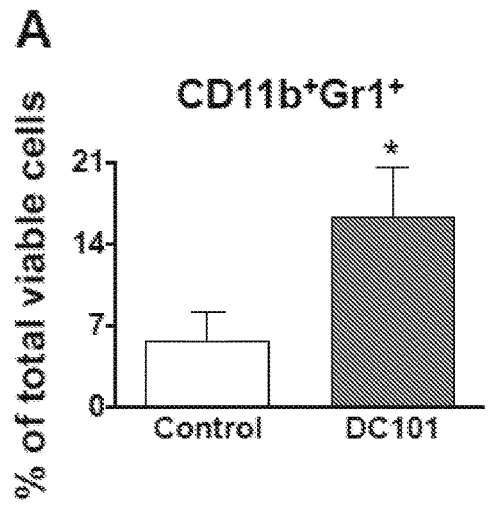

Consistent with published data from anti-VEGF therapies in other tumor models (23), we found a significant increase in $CD11b^+Gr1^+$ myeloid cells in our CRC models after DC101 treatment (FIG. 10A). However, the $CD11b^+Gr1^+$ cells represent a heterogeneous mixture of monocytic and granulocytic myeloid cells (28-30, 35). Although separate analyses for the different sub-populations of myeloid cells are essential for better understanding of the biology, the definition of $CD11b^+Gr1^+$ cell sub-populations using surface markers has been ambiguously defined among research groups. Previous studies have focused on $Gr1^{high}$ ($Ly6C^{high}$ or $Ly6G^+$) myeloid cells (26, 28, 35-43). In this study, we clearly discriminate between $Ly6C^{high}$ and $Ly6G^+$ myeloid cell subsets based on their immunophenotype (i.e. $Ly6C^{high}$ monocytes and $Ly6G^+$ neutrophils, respectively) (FIG. 1C) (Gated on $CD45^+$ $Lin^-$ $F4/80^-$ $CD11c^-$ $CD11b^+$). Furthermore, we also identified a $Ly6C^{low}Ly6G^-$ population—$Ly6C^{low}$ monocytes (FIG. 1C), which have not been reported in tumors after anti-VEGF therapy. These cells display a high level of CX3CR1, while $Ly6C^{high}$ monocytes and $Ly6G^+$ neutrophils (hereafter referred to as neutrophils) express CCR2 and CXCR2, respectively (25, 39, 44) (FIG. 10B).

Example 2. Anti-VEGFR2 Therapy Facilitates Early Infiltration of $Ly6C^{low}$ Monocytes into Tumors FACs based assays were performed to monitor and quantify infiltration of $Ly6C^{low}$ monocytes into orthotopic CRC tumors.

Results

Figures 1D, 1E:
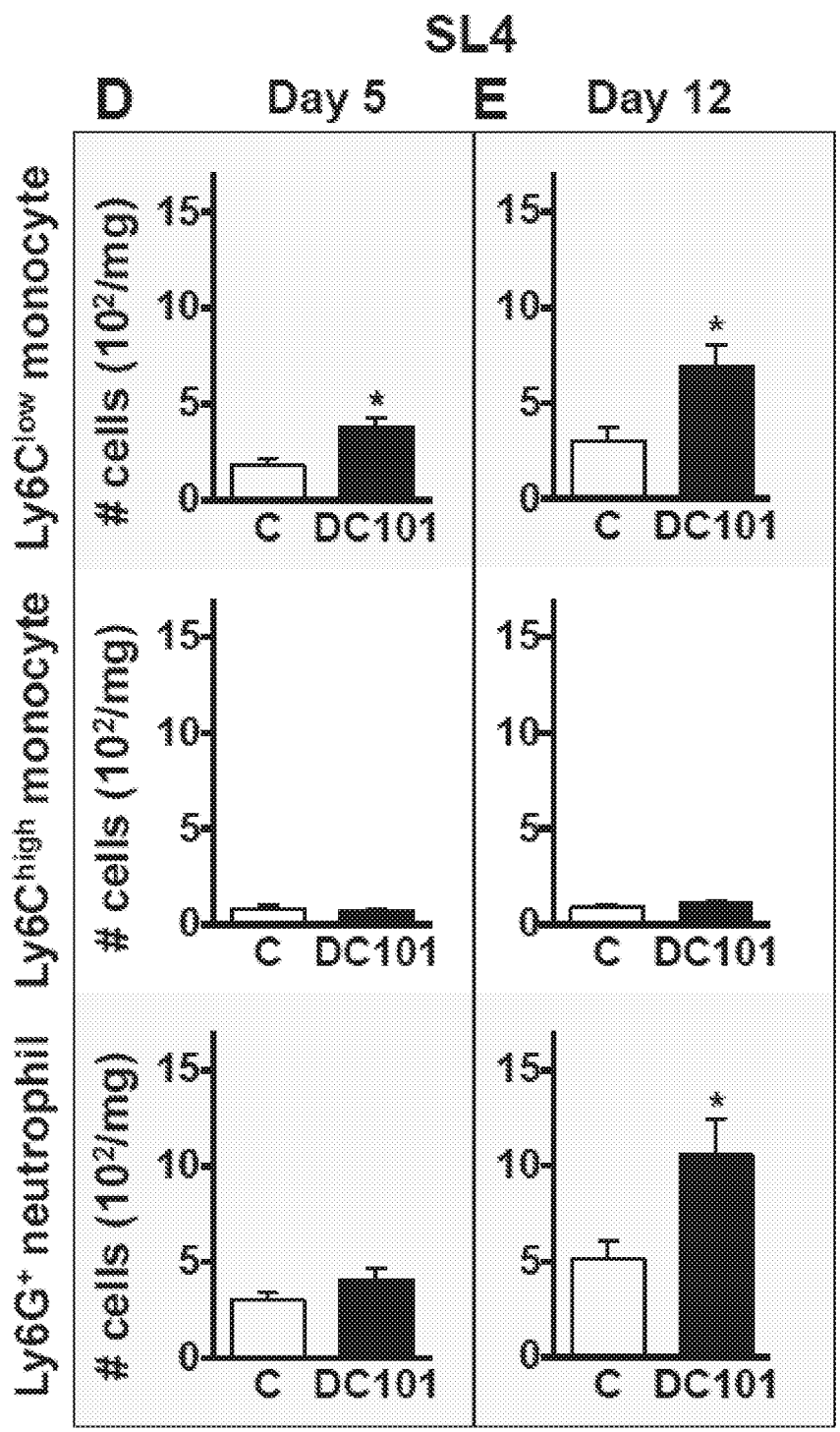
Figures 1F, 1G:
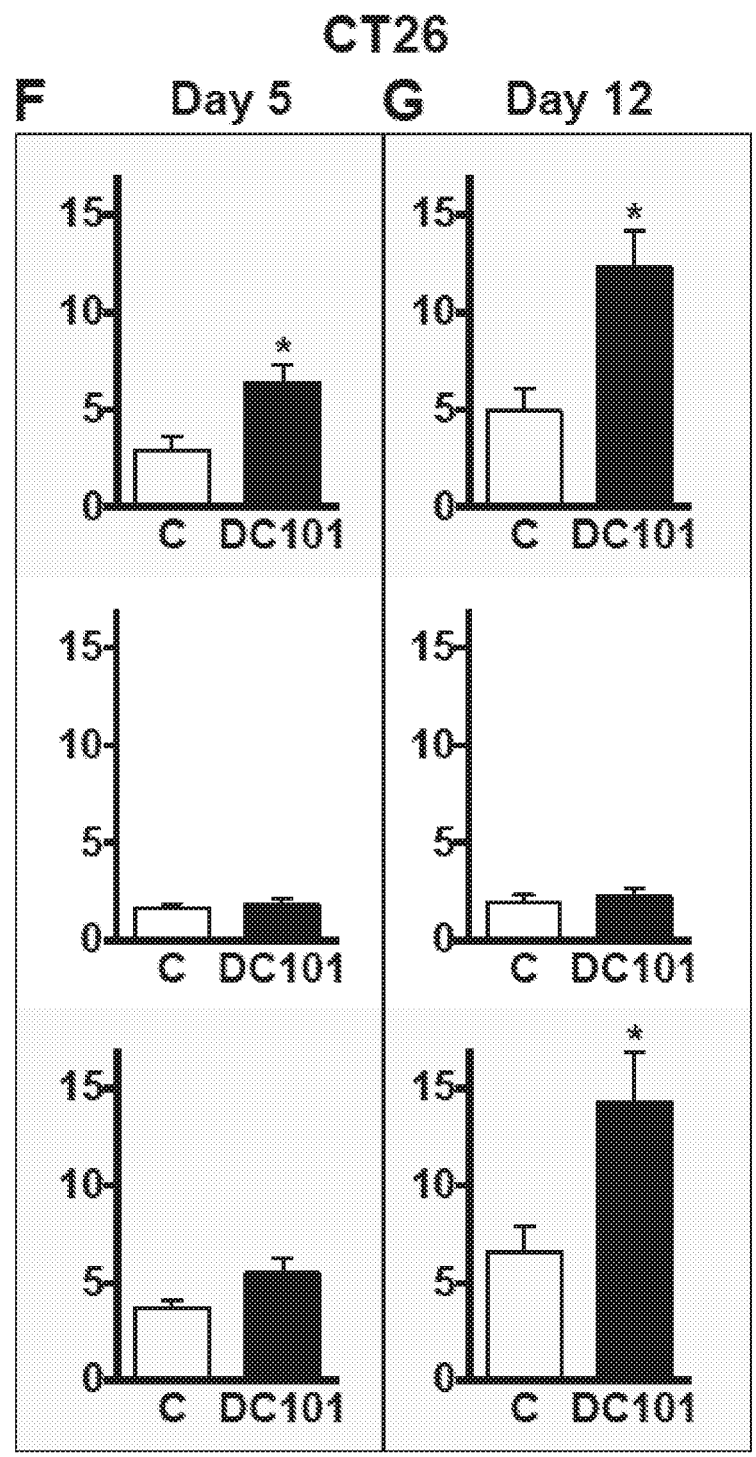

Among the three myeloid cell sub-populations found in SL4 tumors 5 days after DC101 treatment, there was a selective increase in $Ly6C^{low}$ monocytes (380±50 cells/mg) compared to the IgG control (180±40 cells/mg), while the other two myeloid cell subsets did not change significantly (FIG. 1D). On day 12, we observed a further increase in $Ly6C^{low}$ monocytes (300±70 cells/mg in control vs. 700±110 cells/mg in DC101), and also a significant increase in neutrophils (510±100 cells/mg in control vs. 1050±190 cells/mg in DC101) (FIG. 1E). $Ly6C^{high}$ monocytes remained at a similar level between treatment groups on day 12 (FIG. 1E). Given that the average size of the control group tumors harvested on Day 5 and that of DC101 group on Day 12 were similar, the difference in the number of recruited $Ly6C^{low}$ monocytes between two treatment groups is attributed to the treatment (IgG vs DC101), not to the stage of tumor progression. In CT26 tumors, DC101 treatment showed similar kinetic response of $Ly6C^{low}$ monocytes and neutrophils (FIGS. 1F and 1G). In spontaneous rectal tumors in conditional Apc mutant mice, we also observed $Ly6C^{low}$ monocytes infiltrating prior to neutrophils (FIG. 11).

Example 3. $Ly6C^{low}$ Monocytes Progressively Infiltrate into Tumors Over the Course of Anti-VEGFR2 Treatment Microscopy based assays were performed to monitor and quantify infiltration of $Ly6C^{low}$ monocytes into orthotopic CRC tumors treated with anti-VEGF therapy.

Results

Figure 2F:
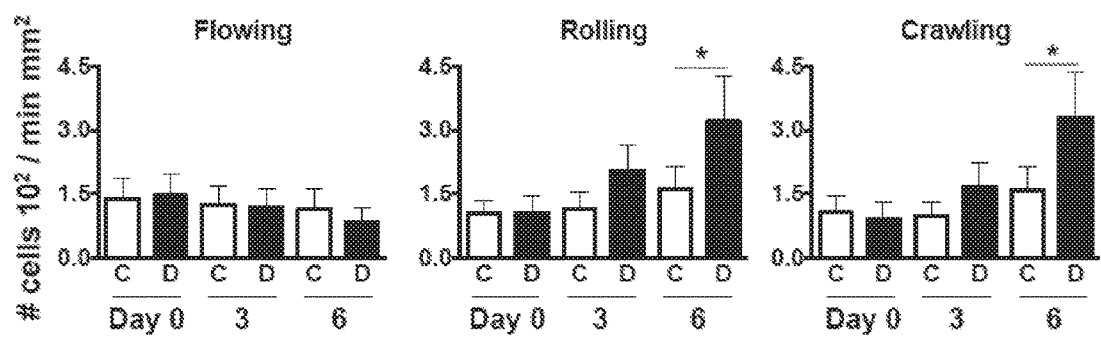
Figures 12A, 12B:
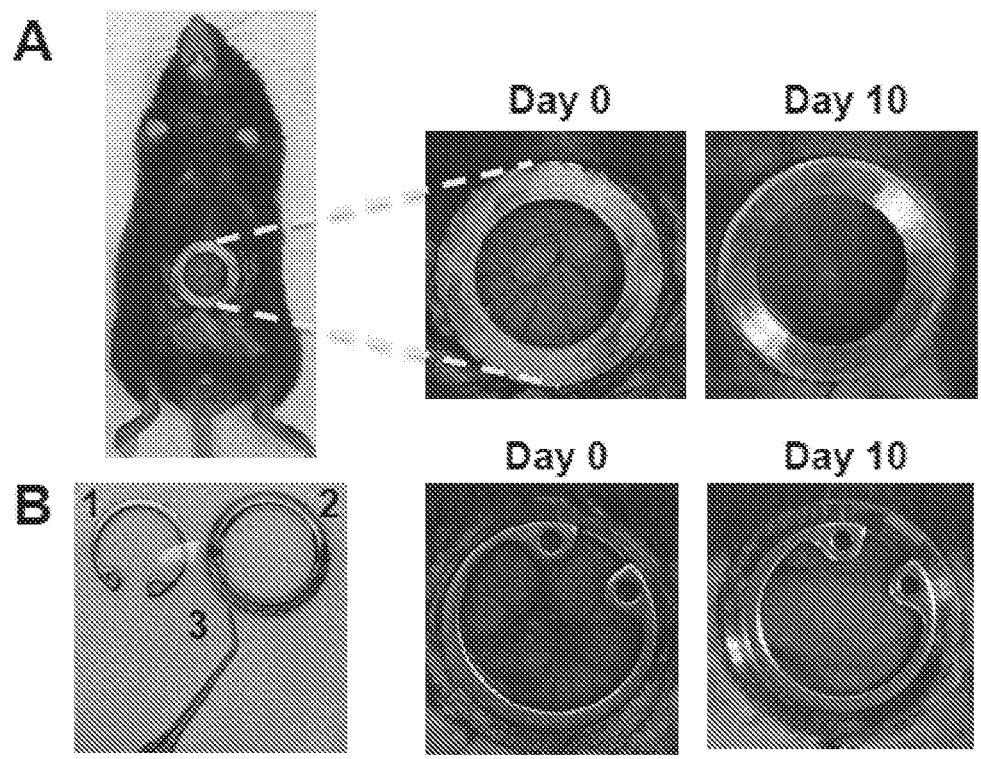
FIGS. 12A-12B. Development of the cecum window. (A) The initial version of the cecum window on a live mouse. At day 10 after implementation of the cecum window, body fluid (i.e., exudate) is accumulated. (B) Modified version of the cecum window on a live mouse. Components of the cecum window are shown; coverslip holder (1), metal ring (2), glass coverslip (3). At day 10 after implementation of the cecum window, body fluid (i.e., exudate) is cleared away by removing the old coverslip and replacing it with a new coverslip. The unique cecum window developed for this study allows longitudinal imaging for over 4 weeks, unparalleled by other imaging windows applicable only for acute or short-term monitoring.
Figure 13:
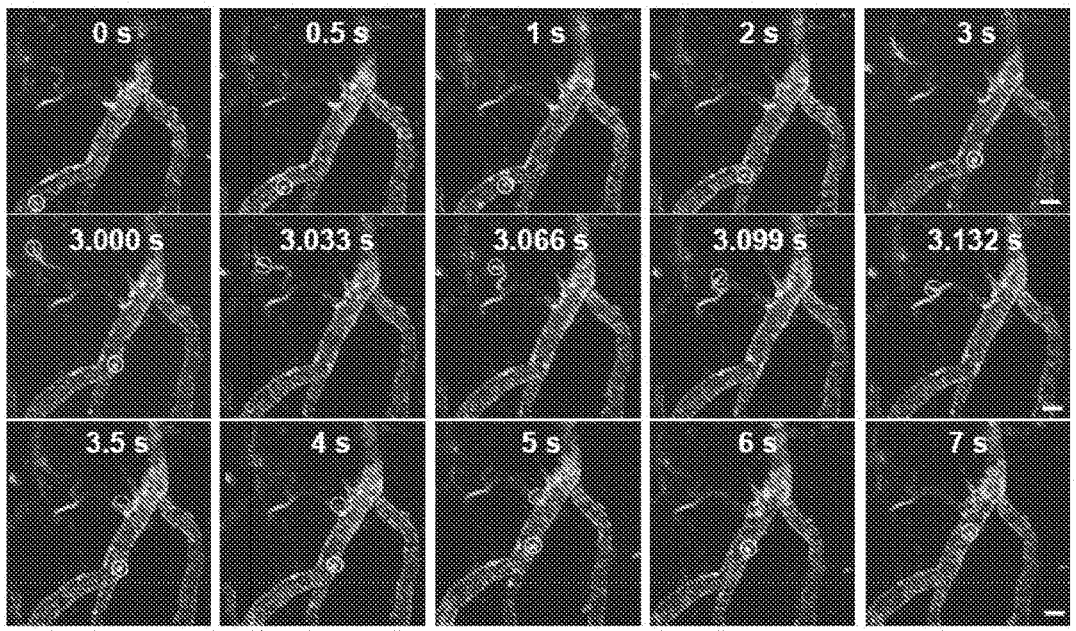
FIG. 13. In vivo real-time monitoring of $CX3CR1^+$ Ly6Clow monocytes in CRCs during anti-VEGFR2 therapy. Snapshot images of a movie showing various behaviors of $CX3CR1^+$ Ly6Clow monocytes inside the blood vessels. Scale bar, 50 µm.

To investigate the dynamic infiltration of $Ly6C^{low}$ monocytes into orthotopic CRC tumors during anti-angiogenic treatment, we surgically implanted a novel abdominal imaging window. (FIGS. 2A and 12). Unlike previous windows (45, 46), the coverslip is removable for aspirating accumulated fluid, allowing clearer imaging of the gut for over 4 weeks using a custom-built video-rate multi-photon microscope (47) (FIGS. 2A-2F, 12B). $Ly6C^{low}$ monocytes express a high amount of CX3CR1 compared to other myeloid cell subsets (FIG. 10B), and $CX3CR1^+$ cells in the bloodstream are predominantly monocytic (48-50). Thus, we used $Cx3cr1^{gfp/+}$ knock-in mice implanted with SL4 tumors, in which $Ly6C^{low}$ monocytes express enhanced green fluorescence protein (EGFP) (50-52). In animals treated with DC101, we frequently observed $EGFP^+$ monocytes freely flowing in the blood that then began to interact with the vessel wall—either rolling or crawling (FIGS. 2D, 2F, and 13). Some of the crawling cells subsequently extravasated from the blood vessel (FIG. 2E). We found that DC101 significantly increased the number of rolling and crawling EGFP⁺ Ly6C$^{low}$ monocytes compared to the control on day 6 (FIG. 2F). There was no significant change in the leukocyte-endothelial cell interaction in the control tumors over time (FIG. 2F). These results show that the blood serves as the source of tumor-infiltrated Ly6C$^{low}$ monocytes—rather than local proliferation of Ly6C$^{low}$ monocytes in the tumor parenchyma—that interact with the tumor vessels and subsequently transmigrate across the endothelium in a time-dependent manner during anti-angiogenic treatment.

Example 4. Ly6C$^{low}$ Monocytes Require CX3CR1 to Infiltrate into Tumors

Figure 2G:
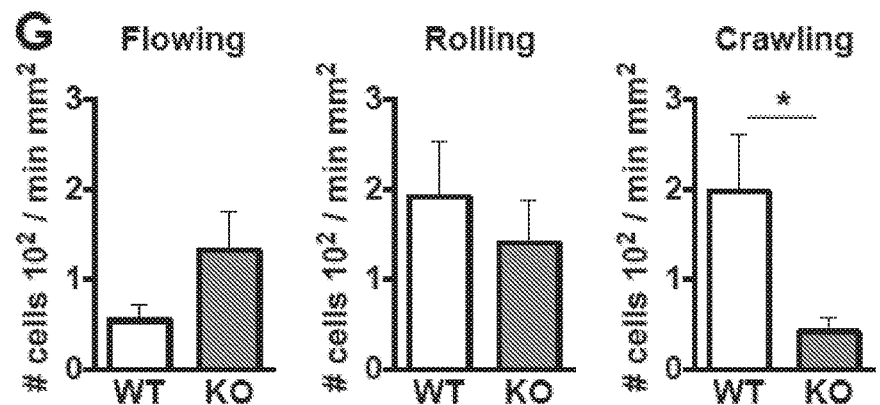

While the CX3CL1/CX3CR1 axis has long been known to be important in chemotaxis (31, 53), it has now become questionable whether CX3CR1 is important for the process of Ly6Clow monocyte recruitment or not (50). There have also been reports suggesting that CX3CR1 deficiency influences the survival of monocytes (54, 55). To determine whether CX3CR1 is critical for Ly6Clow monocyte transmigration across the endothelium, we isolated Ly6Clow monocytes from both wild-type and Cx3cr1−/− mice which were fluorescently labeled, and adoptively transferred each into DC101-treated wild-type mice bearing CRC tumors.
Results Measured by intravital microscopy, there was a significant decrease in the number of crawling Ly6C$^{low}$ monocytes isolated from Cx3cr1$^{−/−}$ mice compared to those isolated from wild-type mice (FIG. 2G). These observations suggest that CX3CR1 plays an important role in chemotaxis-driven transmigration of Ly6C$^{low}$ monocytes, especially in the process of rolling-crawling transition.

Figures 3A, 3B:
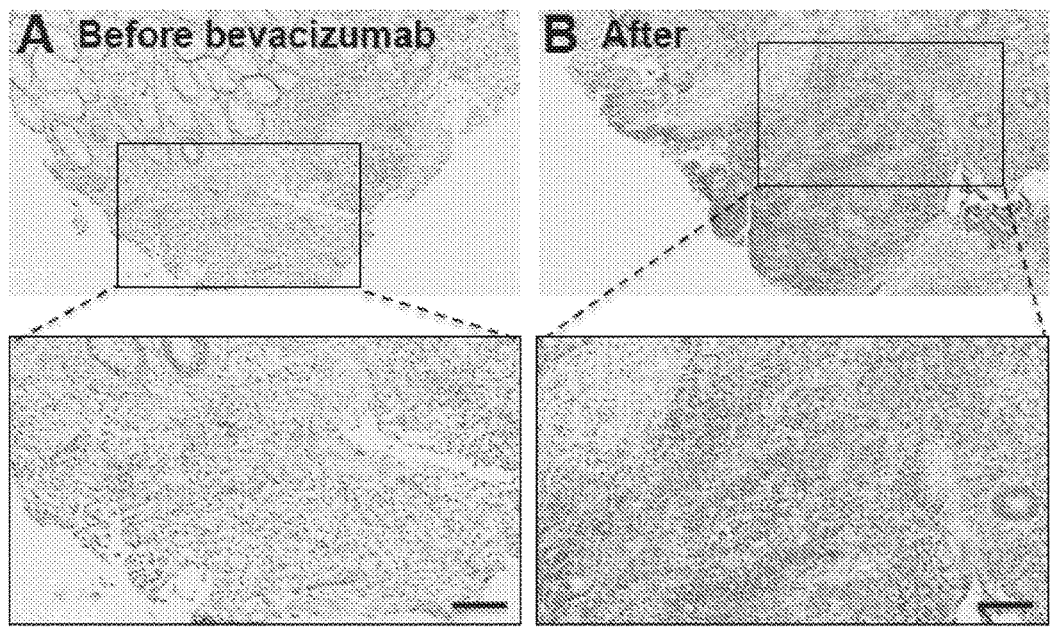
FIGS. 3A-3F. Blockade of VEGF/VEGFR2 signaling upregulates CX3CL1 in both human and mouse CRCs. (A and B) Representative images showing CX3CL1 (fractalkine) expression in human tissue sections from patients with rectal carcinomas (total 7 pairs) before (A) and after (B) bevacizumab treatment. Scale bar=100 μm. (C) Averaged percentage of CX3CL1$^+$ area out of total area from tissue sections of 7 rectal cancer patients before and after bevacizumab treatment. Two-tailed t test. n=7/group. *, P<0.05 versus before. (D) CX3CL1$^+$ area percentage of total viable area from SL4 tumors treated with either control rat IgG (C) or DC101 analyzed on day 12. n=7/group. Two-tailed t test. *, p<0.05 versus control. (E) CX3CL1 protein level measured from tissue lysates of tumors treated with either control rat IgG (C) or DC101 (D). n=5/group. Two-tailed t test. *, p<0.05 versus control. (F) Western blot analysis of CX3CL1 protein expression in endothelial cells in vitro. Serum-starved endothelial cells were treated with either recombinant VEGF-A protein, DC101, or VEGF-A protein+DC101, and CX3CL1 protein levels were measured from cell lysates. The blockade of VEGF/VEGFR2 signaling stimulates upregulation of CX3CL1 in endothelial cells. Three independent experiments showed similar findings.
Figure 3C:
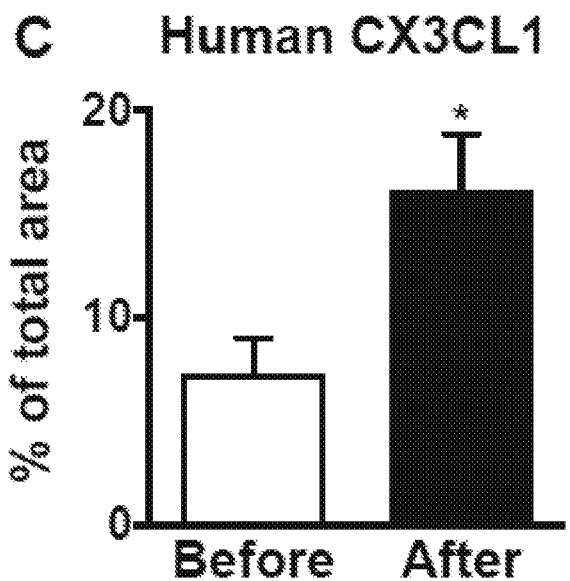

Example 5. Blockade of VEGF/VEGFR2 Signaling Upregulates CX3CL1 in Both Human and Mouse CRCs Gene expression and protein analysis (e.g. ELISA, western blotting, and immunohistochemistry) was performed to determine which factors contribute to the CX3CR1-dependent attraction of Ly6Clow monocytes after DC101 treatment.
Results CX3CL1—also known as fractalkine—is the only known ligand for CX3CR1 (31, 53). Immunohistochemistry showed that CX3CL1 is dramatically upregulated after DC101 treatment (FIG. 3). Furthermore, biopsies of rectal carcinomas from patients before and after bevacizumab treatment (56, 57) also showed a significant increase in CX3CL1 expression after bevacizumab treatment (FIGS. 3A-3C).

Figures 3D, 3E, 3F:
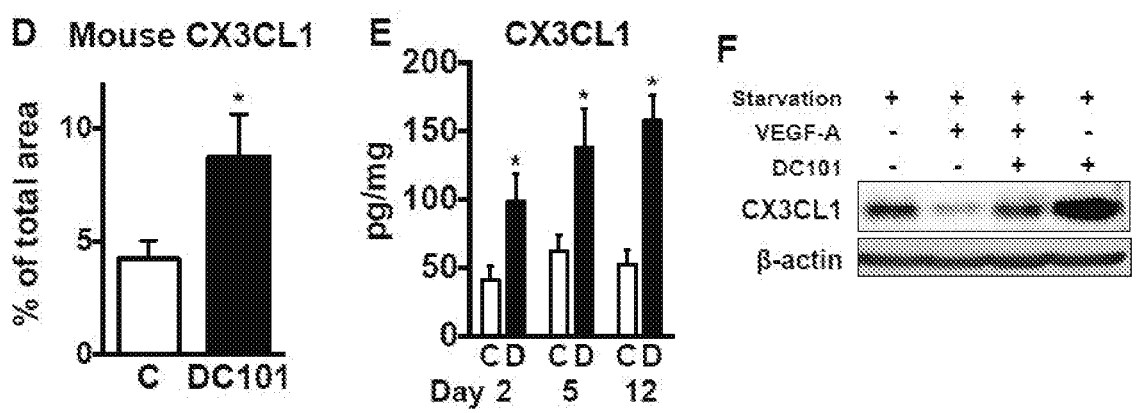

By measuring protein levels, we found an increase in CX3CL1 in tumor tissues on Day 2 onwards after DC101 treatment (FIGS. 3D and 3E). Furthermore, we found increased CX3CL1 expression in endothelial cells isolated from tumors treated with DC101 (FIGS. 3G and 7D), consistent with published data showing endothelial cells being a source of CX3CL1 (31, 58), while there was no change in CX3CL1 expression in non-endothelial cells. Interestingly, endothelial cells treated with recombinant VEGF-A protein to activate VEGF/VEGFR2 signaling in vitro showed reduced expression of CX3CL1 (FIG. 3F). The reduction of CX3CL1 level was recovered by using DC101 to block VEGF/VEGFR2 signaling (FIG. 3F). These results suggest that CX3CL1 is produced by endothelial cells and that production is regulated by VEGFR2 signaling. Furthermore, since the elevation of CX3CL1 expression precedes the induction of hypoxia (FIGS. 3E and 9D), this process may not be hypoxia-dependent, although we cannot rule out the contribution of hypoxia in the later time points. Thus, blockade of VEGF/VEGFR2 signaling stimulates robust upregulation of CX3CL1 and causes active recruitment of CX3CR1⁺ Ly6C$^{low}$ monocytes to tumors.

Figure 4A:
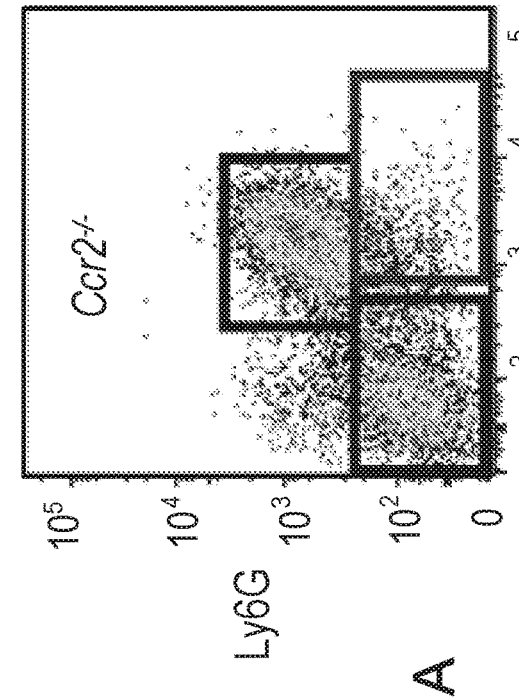
FIGS. 4A-4H. Ly6C$^{low}$ monocyte infiltration during anti-VEGFR2 treatment recruits neutrophils via CXCL5. (A to D) Representative flow cytometry plots depicting subset-specific depletion of myeloid cells in (A) wild-type (WT) control, (B) Cx3cr1$^{-/-}$ (Ly6C$^{low}$ monocyte), (C) Ccr2$^{-/-}$ (Ly6C$^{high}$ monocyte) and (D) anti-Ly6G antibody-treated mice (Ly6G$^+$ neutrophil). (E to G) Monocytes and neutrophils in SL4 tumors of (E) C57BL/6 Cx3cr1$^{-/-}$, (F) Ccr2$^{-/-}$ or (E to G), WT mice bearing SL4 tumors were treated with either control rat IgG (C), anti-Ly6G antibody (G), DC101 (D), or anti-Ly6G antibody+DC101 (G+D). Each subset of myeloid cells in tumor infiltrate was analyzed on day 12 by flow cytometry. n=8/group. Comparison between groups was made using ANOVA with Holm-Sidak post-hoc test. *, p<0.05. The graphs depict the absolute number of cells per mg of tumor tissue (E-G). Data are representative of three independent experiments. (H) In vitro migration assay. Neutrophils isolated from tumors were seeded in the upper chamber and their migration to the bottom part of the chamber was measured. The lower chamber included either tumor-isolated Ly6C$^{low}$ monocytes, Ly6C$^{high}$ monocytes, or their conditioned media with or without neutralizing antibodies for the chemokine/chemokine receptor as indicated. n=9/group. Comparison between groups was made using ANOVA with Holm-Sidak post-hoc test. *, p<0.05 versus control (first bar). #, p<0.05 versus Ly6C$^{low}$ monocytes (second bar). Data are represented as mean±SEM.
Figure 4C:
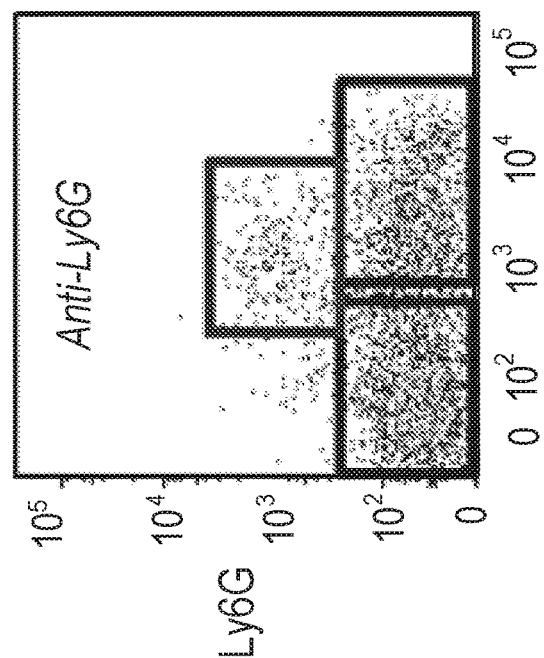
Figure 4B:
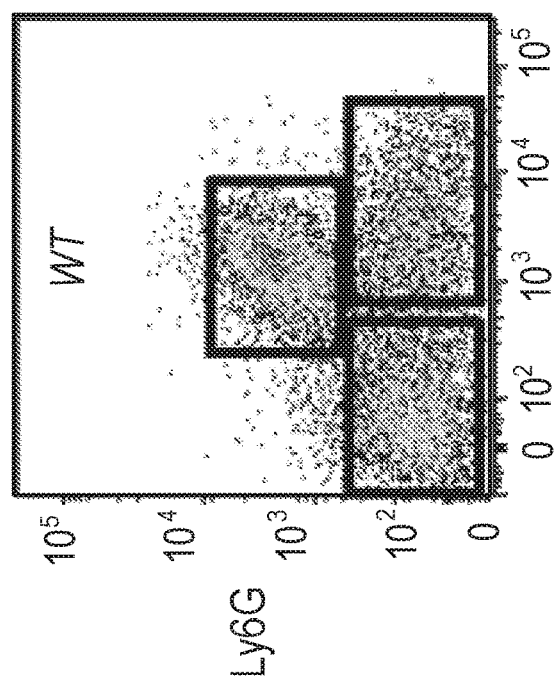
Figure 4D:
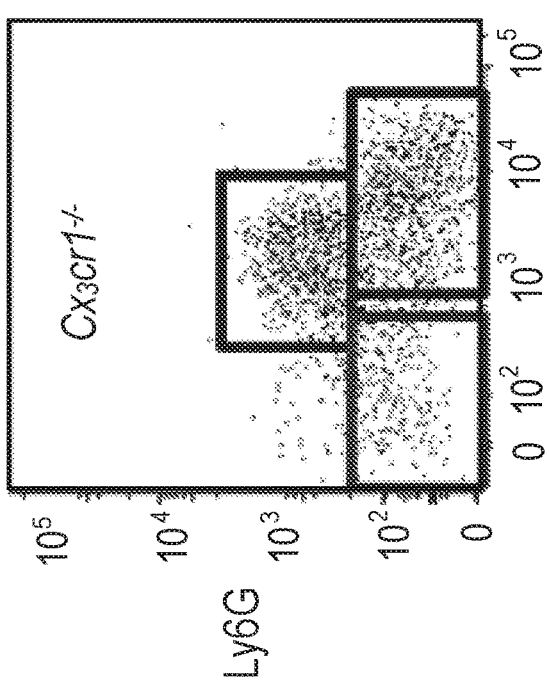
Figures 4E, 4F, 4G:
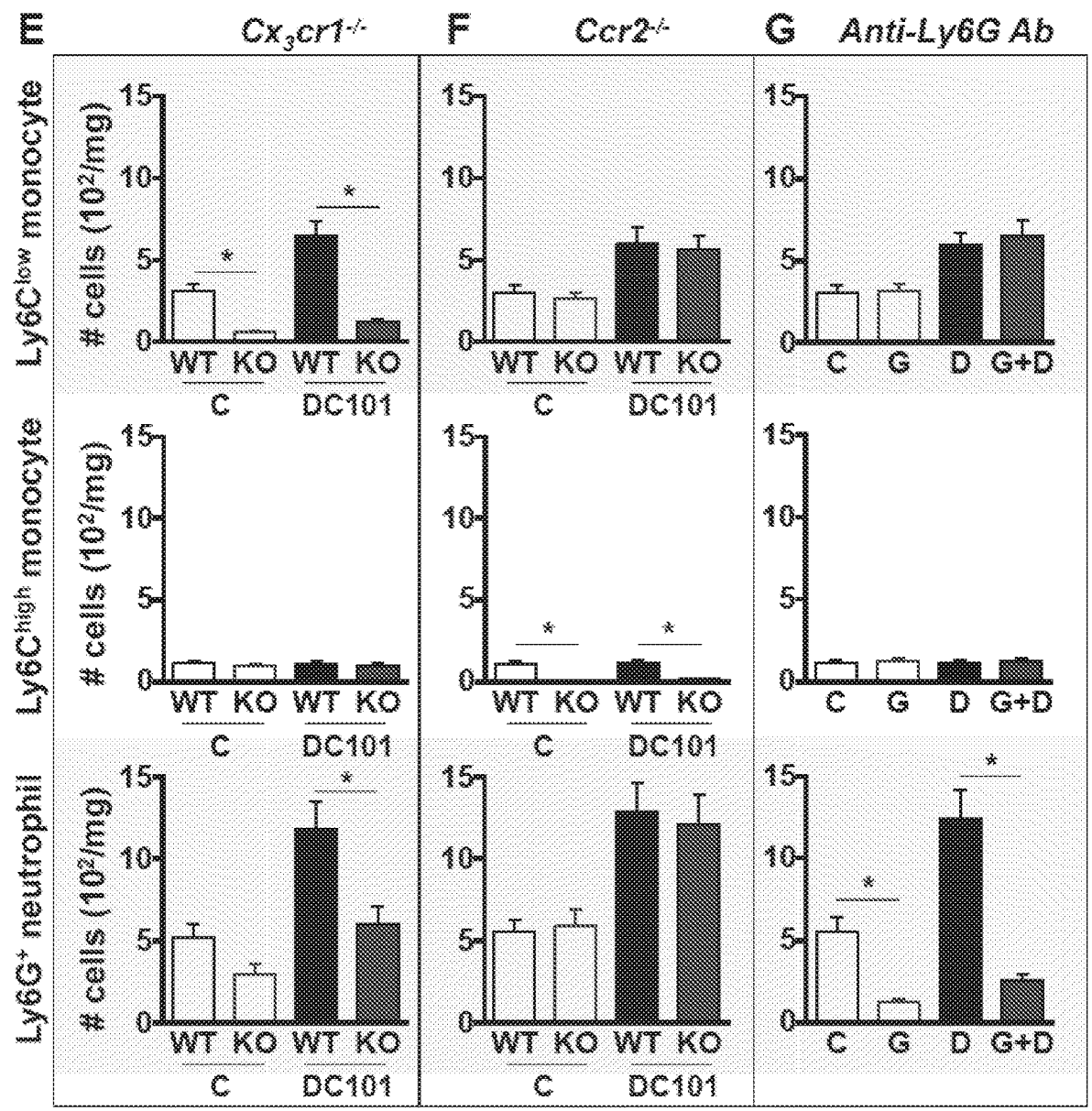
Figures 11A, 11B:
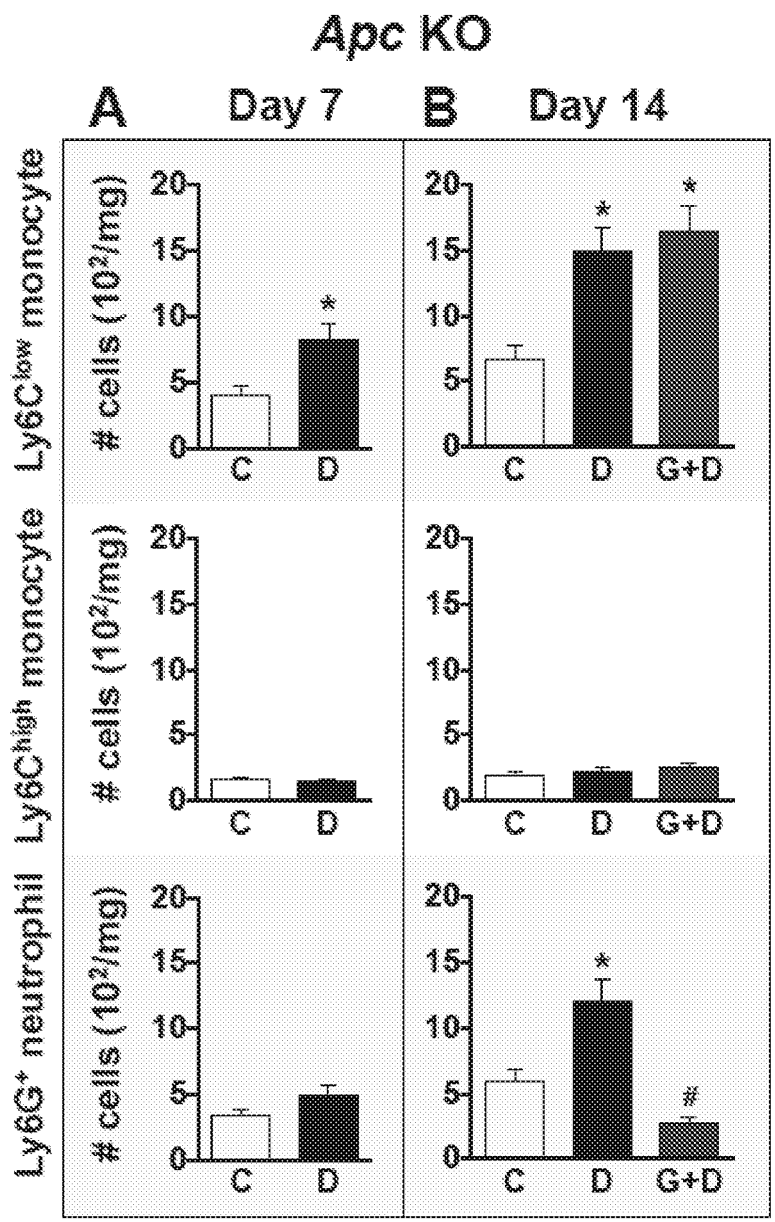

Example 6. Ly6C$^{low}$ Monocyte Infiltration During Anti-VEGFR2 Treatment Recruits Neutrophils Potentially DC101 treatment facilitates early infiltration of Ly6C$^{low}$ monocytes (day 5), which subsequently recruit neutrophils to these tumors (day 12) (FIG. 1). To test this hypothesis, we selectively inhibited the infiltration of each myeloid cell subset by taking advantage of the unique expression of specific chemokine receptors on their surface, which are critical for their migration (i.e., CX3CR1 on Ly6Clow monocytes, CCR2 on Ly6C$^{high}$ monocytes) (32, 59) (FIG. 10B).
Results There was nearly 80% depletion of Ly6C$^{low}$ monocytes in SL4 tumors growing in Cx3cr1$^{−/−}$ mice when compared with wild-type mice (FIGS. 4A, 4B, and 4E). In Ccr2$^{−/−}$ mice, there was a ~90% depletion of Ly6C$^{high}$ monocytes (FIGS. 4C and 4F). Finally, we used an anti-Ly6G neutralizing antibody to pharmacologically deplete the Ly6G⁺ neutrophils (with a depletion efficiency of ~80%) (FIGS. 4D and 4G). Interestingly, DC101-treated tumors in Cx3cr1$^{−/−}$ mice showed not only a lack of Ly6C$^{low}$ monocytes but also significantly reduced infiltration of neutrophils compared to wild-type animals (FIG. 4E). On the other hand, administration of an anti-Ly6G antibody selectively depleted Ly6G⁺ neutrophils without affecting Ly6C$^{low}$ monocytes (FIGS. 4G and 11B). These data indicate that early infiltration of Ly6C$^{low}$ monocytes during anti-VEGFR2 treatment promotes subsequent recruitment of neutrophils to tumors.

Figure 4H:
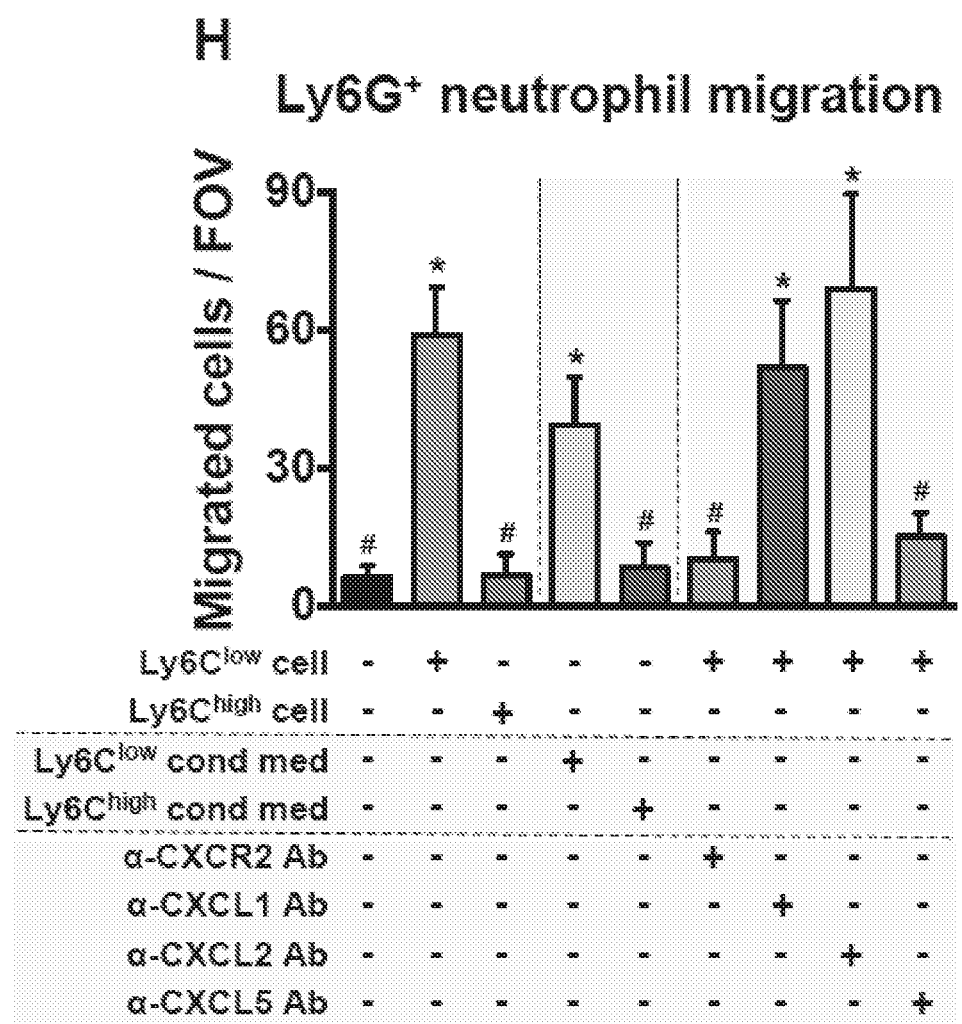

Example 7. Ly6C$^{low}$ Monocytes Attract Neutrophils Via CXCL5 During Anti-VEGFR2 Treatment in CRCs Towards elucidating the underlying mechanisms of how Ly6C$^{low}$ monocytes attract neutrophils in the context of anti-VEGF therapies, a series of neutrophil infiltration assays were performed.
Results Ly6C$^{low}$ monocytes grown in vitro significantly increased the number of neutrophils which migrate to the bottom part of a Boyden chamber, while Ly6C$^{high}$ monocytes did not (FIG. 4H). DC101-treated tumors, characterized by abundant infiltration of Ly6C$^{low}$ monocytes compared to the control (FIGS. 1D-1G), had a significantly higher level of CXCL5—a chemokine known to attract CXCR2⁺ cells (FIG. 10D). Ly6C$^{low}$ monocytes secrete high-levels of CXCL5 compared to Ly6C$^{high}$ monocytes (FIG. 10C). Since neutrophils express CXCR2 on their surface (FIG. 10B), we hypothesized that CXCL5 from Ly6C$^{low}$ monocytes is a main chemoattractant for neutrophil recruitment. To verify this, we used an anti-CXCR2 and anti-CXCL5 neutralizing antibodies and measured impaired neutrophil migration toward Ly6C$^{low}$ monocytes (FIG. 4H). Other chemokines known to bind to CXCR2 (i.g. CXCL1 and CXCL2) did not seem to be crucial for attracting neutrophils in our models (FIG. 4H). These results support our hypothesis that Ly6C$^{low}$ monocytes secrete CXCL5 to recruit neutrophils expressing CXCR2.

Figures 5A, 5B:
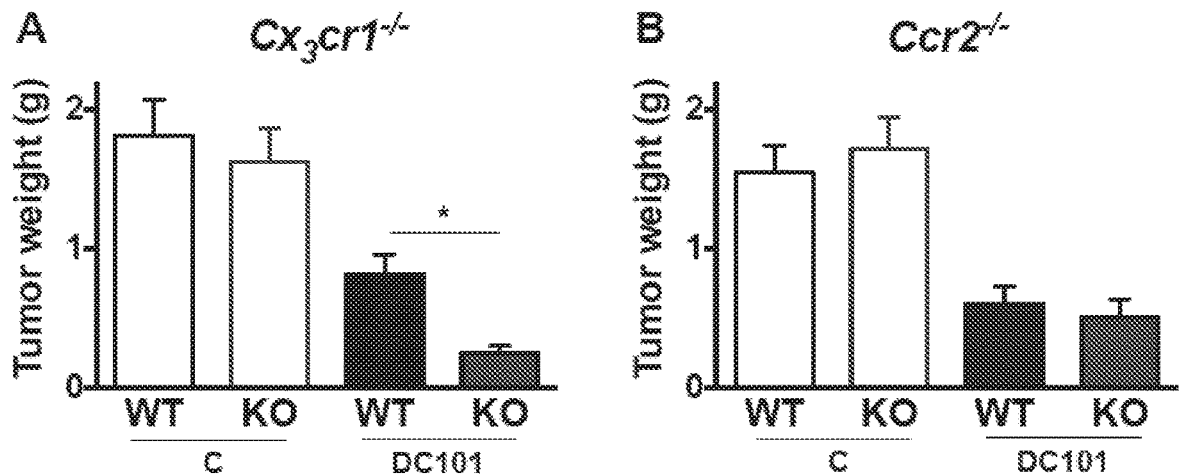
FIGS. 5A-5D. Blockade of CX3CR1-dependent infiltration of Ly6C$^{low}$ monocytes improves efficacy of anti-VEGFR2 therapy. (A) SL4 tumors were grown in C57BL/6 WT mice or Cx$_3$cr1$^{-/-}$ (CX3CR1 KO) mice and treated with either control rat IgG (C) or DC101. Tumor weight was measured on day 12 after treatment (A-D). (B) SL4 tumors were grown in C57BL/6 WT mice or Ccr2$^{-/-}$ (CCR2 KO) mice and treated as indicated. (C) SL4 tumor-bearing C57BL/6 WT mice were treated with either control rat IgG (C), anti-Ly6G antibody (G), DC101 (D), or anti-Ly6G antibody+DC101 (G+D). Data are represented as mean±SEM. n=8/group. Comparison between groups was made using ANOVA with Holm-Sidak post-hoc test. *, p<0.05. Data are representative of three independent experiments (A-C). (D) DC101-treated $Cx_3cr1^{-/-}$ mice received adoptive transfer of either tumor-isolated WT Ly6C$^{low}$ monocytes (Ly6C$^{low}$), WT Ly6C$^{high}$ monocytes (Ly6C$^{high}$), or Ly6C$^{low}$ monocytes isolated from tumors of $Cx_3cr1^{-/-}$ mice (KO Ly6C$^{low}$) twice a week from the beginning of DC101 treatment. Data are represented as mean±SEM. n=8/group. Comparison between groups was made using ANOVA with Holm-Sidak post-hoc test. *, p<0.05 versus without cell transfer; #, p<0.05 versus $Cx_3cr1^{-/-}$ control mice without cell transfer.
Figures 5C, 5D:
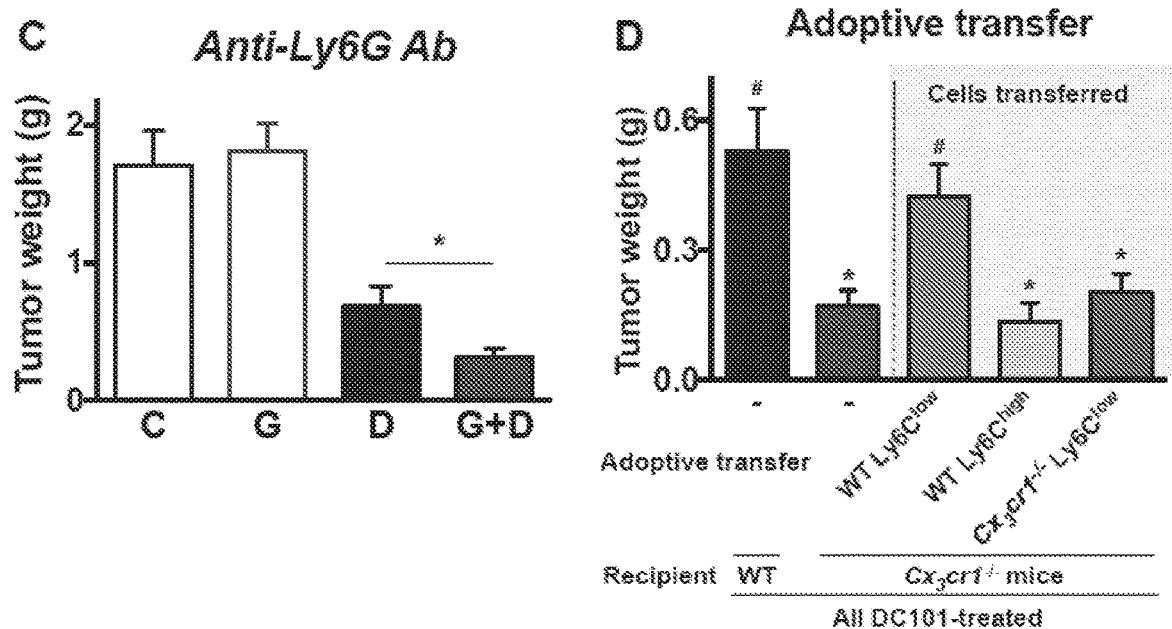
Figures 14A, 14B, 14C:
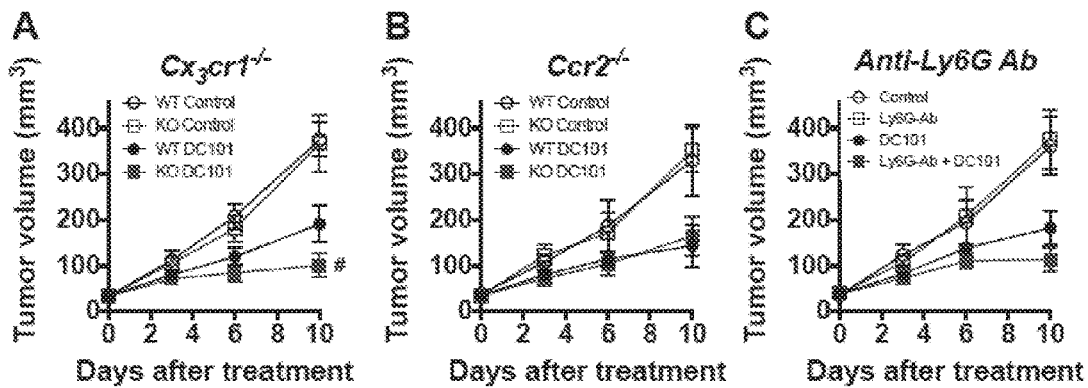
FIGS. 14A-14F. Blockade of CX3CR1-dependent infiltration of Ly6Clow monocytes improves efficacy of anti-VEGFR2 therapy. (A to C) SL4 tumor growth. Tumor volume was measured using a high-frequency ultrasound imaging system for C57BL/6 mice bearing orthotopically grown syngeneic SL4 tumors. (A) The effect of CX3CR1 deletion on SL4 tumor growth. SL4 tumors were grown in C57BL/6 WT mice or Cx3cr1−/− (CX3CR1 KO) mice and treated with either control rat IgG or DC101. Data are represented as mean±SEM. n=8/group. ANOVA with Holm-Sidak post-hoc test. #, p<0.05 versus WT DC101. (B) The effect of CCR2 deletion on SL4 tumor growth. SL4 tumors were grown in C57BL/6 WT mice or Ccr2−/− (CCR2 KO) mice and treated as indicated. Data are represented as mean±SEM. n=8/group. (C) The effect of administration of anti-Ly6G antibody on SL4 tumor growth. SL4 tumor-bearing C57BL/6 WT mice were treated with either control rat IgG; anti-Ly6G antibody, DC101, or anti-Ly6G antibody+DC101. Data are represented as mean±SEM. n=8/group. Data are representative of three independent experiments. (D to F) Monocytes and neutrophils in SL4 tumors (FIG. 5D). DC101-treated Cx3cr1−/− mice received adoptive transfer of either tumor-isolated WT Ly6Clow monocytes (Ly6Clow), WT Ly6Chigh monocytes (Ly6Chigh), or Ly6Clow monocytes isolated from tumors of Cx3cr1−/− mice (KO Ly6Clow). Each subset of myeloid cells in tumor infiltrate was analyzed on day 12 by flow cytometry. Data are represented as mean±SEM. ANOVA with Holm-Sidak post-hoc test. n=8/group. *, p<0.05 versus Cx3cr1−/− control mice without cell transfer. The graphs depict data for the absolute number of cells per mg of tumor tissue.

Example 8. Blockade of CX3CR1-Dependent Infiltration of Ly6C$^{low}$ Monocytes Improves Efficacy of Anti-VEGFR2 Therapy To determine the in vivo function of each myeloid cell subset in context of anti-VEGF treatment to specifically inhibit their infiltration into tumor environments, a series of infiltration assays were performed.
Results In Cx3cr1$^{-/-}$ mice, which have reduced tumor infiltration of Ly6C$^{low}$ monocytes and neutrophils (FIG. 4E), DC101 monotherapy exerted an enhanced anti-tumor effect compared to the same treatment in wild-type mice (FIGS. 5A and 14A). On the other hand, depletion of Ly6C$^{high}$ monocytes in Ccr2$^{-/-}$ mice did not change the treatment efficacy of DC101 compared to wild-type mice (FIGS. 5B and 14B). Administration of an anti-Ly6G antibody—causing a significant reduction in Ly6G$^+$ neutrophils—enhanced the anti-tumor effect of DC101, independent of monocyte infiltration (FIGS. 5C and 14C). Taken together, we conclude that the hindrance of either DC101-induced early infiltration of Ly6C$^{low}$ monocytes or subsequent recruitment of neutrophils is sufficient to improve the anti-tumor efficacy of anti-VEGFR2 therapy.

Figures 14D, 14E, 14F:
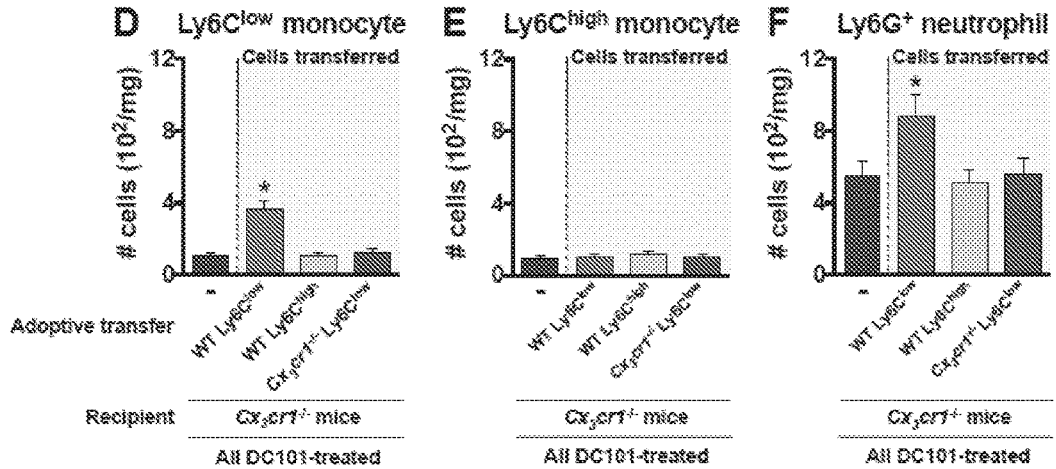

Example 9. Adoptive Transfer of Ly6C$^{low}$ Monocytes Abrogates Improved Efficacy of Anti-VEGFR2 Therapy in Cx3cr1$^{-/-}$ Mice To determine whether Ly6Clow monocytes could "rescue" the phenotype in Cx3cr1-/- mice a series of adoptive transfer experiments were performed.
Results Tumor weight of DC101-treated Cx3cr1-/- mice that received adoptive transfer of wild-type Ly6Clow monocytes was significantly higher than that of DC101-treated Cx3cr1-/- mice without cell transfer (FIG. 5D). We confirmed that the adoptive transfer increased the numbers of Ly6C$^{low}$ monocytes and neutrophils in the tumors in Cx3cr1$^{-/-}$ mice (FIGS. 14D-14F). We also adoptively transferred Ly6C$^{low}$ monocytes isolated from Cx3cr1$^{-/-}$ mice. Since Ly6C$^{low}$ monocytes from Cx3cr1$^{-/-}$ mice lack CX3CR1 expression on their surface, these adoptively transferred cells did not infiltrate into tumors and tumor weights were not increased (FIGS. 5D and 14D). Also, adoptive transfer of Ly6C$^{high}$ monocytes did not increase the tumor weight compared to the DC101-treated Cx$_3$cr1$^{-/-}$ mice without cell transfer (FIG. 5D). These data suggest that CX3CR1 signaling is the key mechanism driving Ly6C$^{low}$ monocyte infiltration in CRCs and that Ly6C$^{low}$ monocytes influence tumor growth.

Figures 9A, 9B, 9C, 9D:
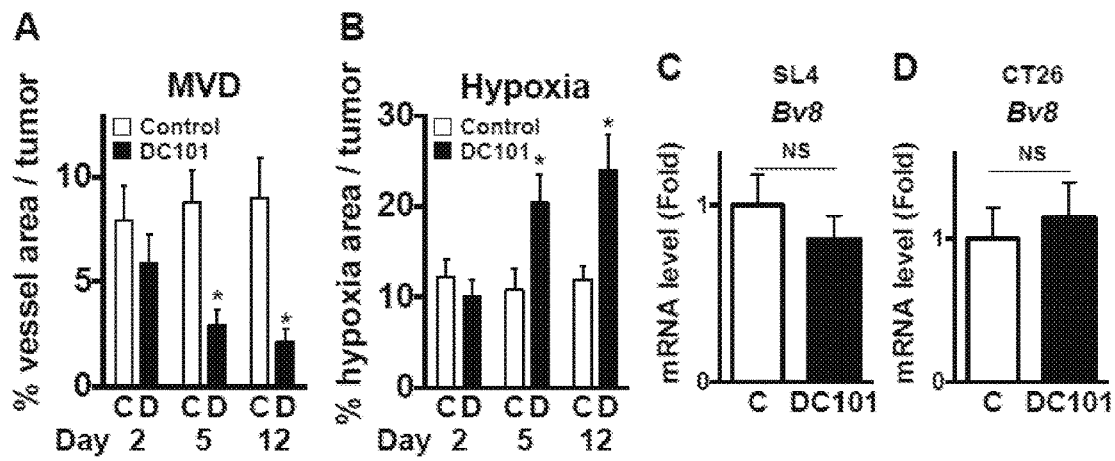
FIGS. 9A-9F. Anti-VEGFR2 therapy induces vessel regression and hypoxia in CRCs. (A) CD31+ area percentage of total viable area (microvessel density) from SL4 tumors of control (C) and DC101 (D) groups. Data are represented as mean±SEM. n=5/group. Two-tailed t test. *, p<0.05 versus control. (B) Hypoxic area percentage of total viable area (hypoxia) from SL4 tumors of control (C) and DC101 (D) groups. Data are represented as mean±SEM. n=5/group. Two-tailed t test. *, p<0.05 versus control. (C and D) Relative gene expression levels of Bv8 in SL4 (E) and CT26 tumors (F) were determined by quantitative real-time PCR, normalized against GAPDH. C57BL/6 and BALB/c WT mice bearing orthotopically grown syngeneic CRCs were treated with either control rat IgG (C) or DC101, and mRNA levels were analyzed on day 12. Data are represented as mean±SEM. n=5/group. Two-tailed t test. NS, non-significant.
Figures 9E, 9F:
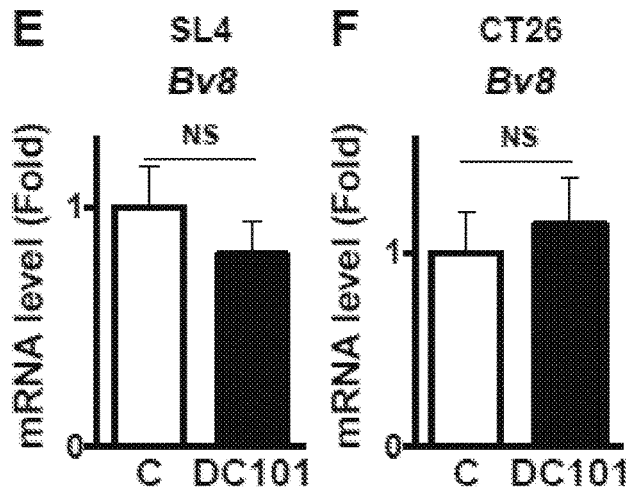

Example 10. Ly6C$^{low}$ Monocytes Drive Immunosuppression During Anti-VEGFR2 Treatment in CRCs To determine if anti-angiogenic therapy-induced Ly6Clow monocyte-infiltration supports tumor growth we performed assays with anti-VEGF and DC101 treated tumors.]
Results As shown in FIG. 9C, we observed vessel regression on Day 5 and 12 after DC101 treatment without any rebound of vessel density, suggesting that tumor-infiltrating Ly6C$^{low}$ monocytes or neutrophils do not seem to promote tumor angiogenesis. Consistent with this, we did not observe any significant difference in levels of Bv8 expression—previously implicated in the anti-angiogenesis therapy resistance process by promoting angiogenesis (23)—between DC101-treated and control tumors in our models (FIGS. 9E and 9F).

Figure 15A:
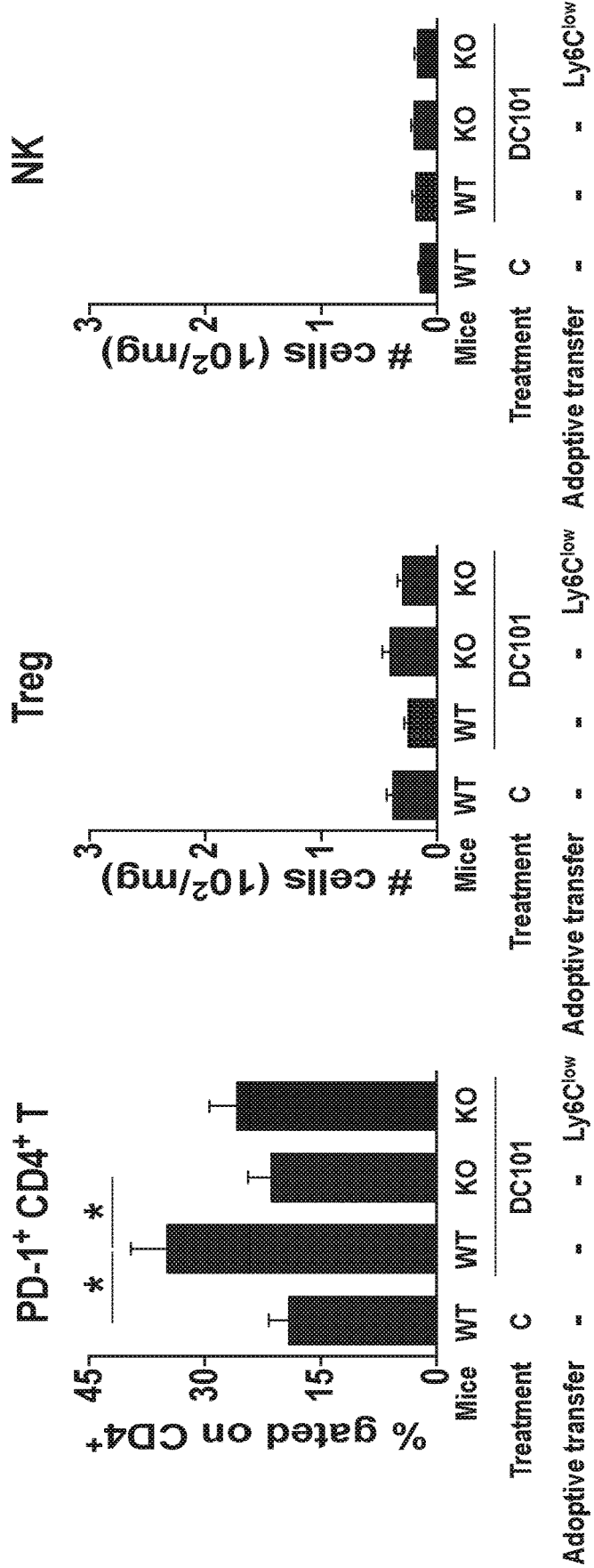
FIGS. 15A-15C. Ly6Clow monocytes drive immunosuppression during anti-VEGFR2 treatment in CRCs. (A) Flow cytometric analysis of PD-1+ CD4+ T cells, regulatory T cells (Treg), and NK cells in SL4 tumors as indicated; WT mice bearing SL4 tumors treated with control rat IgG; WT mice bearing SL4 tumors treated with DC101; Cx3cr1−/− mice bearing SL4 tumors treated with DC101 without cell transfer; DC101-treated Cx3cr1−/− mice received adoptive transfer of tumor-isolated WT Ly6Clow monocytes. The PD-1+ CD4+ T graphs depict data for PD-1+ populations relative to total CD4+ T cells. The Treg and NK graphs depict data for the absolute number of cells per mg of tumor tissue. The lymphocyte infiltrate in the tumor was analyzed on day 12 by flow cytometry. Data are represented as mean±SEM. n=8/group. ANOVA with Holm-Sidak post-hoc test. *, p<0.05. (B) Representative flow cytometric analyses of nonactivated or activated CD8+ T cell proliferation. CellTrace-labeled splenic CD8+ T cells from syngeneic mice were activated and cocultured with either tumor-isolated Ly6Clow monocytes, Ly6Chigh monocytes, or Ly6G+ neutrophils. Data are representative of three independent experiments. (C) Representative flow cytometric analyses of nonactivated or activated CD4+ T cell proliferation. CellTrace-labeled splenic CD4+ T cells from syngeneic mice were activated and co-cultured with either tumor-isolated Ly6Clow monocytes, Ly6Chigh monocytes, or Ly6G+ neutrophils. All data are representative of three independent experiments.
Figure 15B:
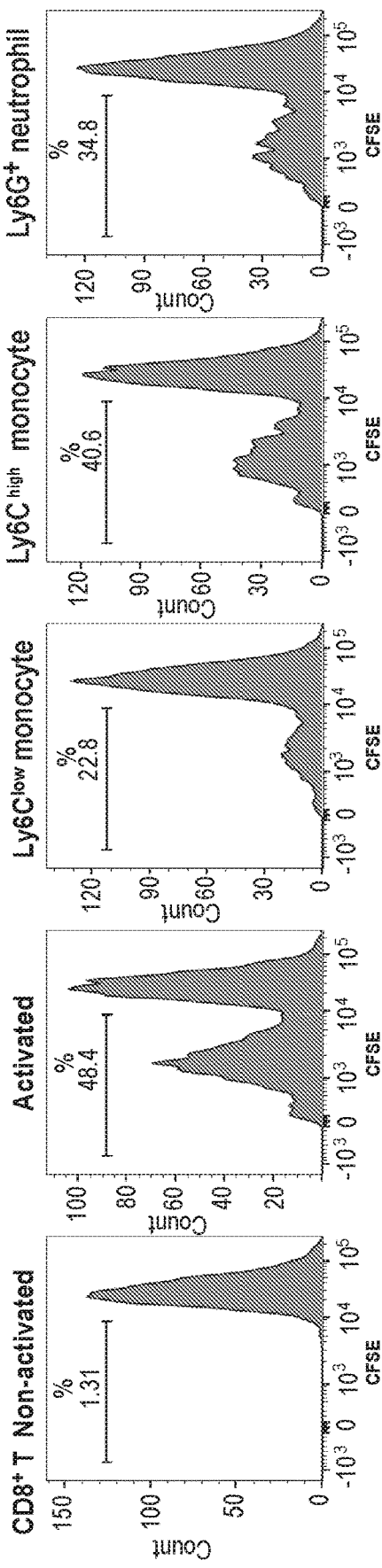
Figure 15C:
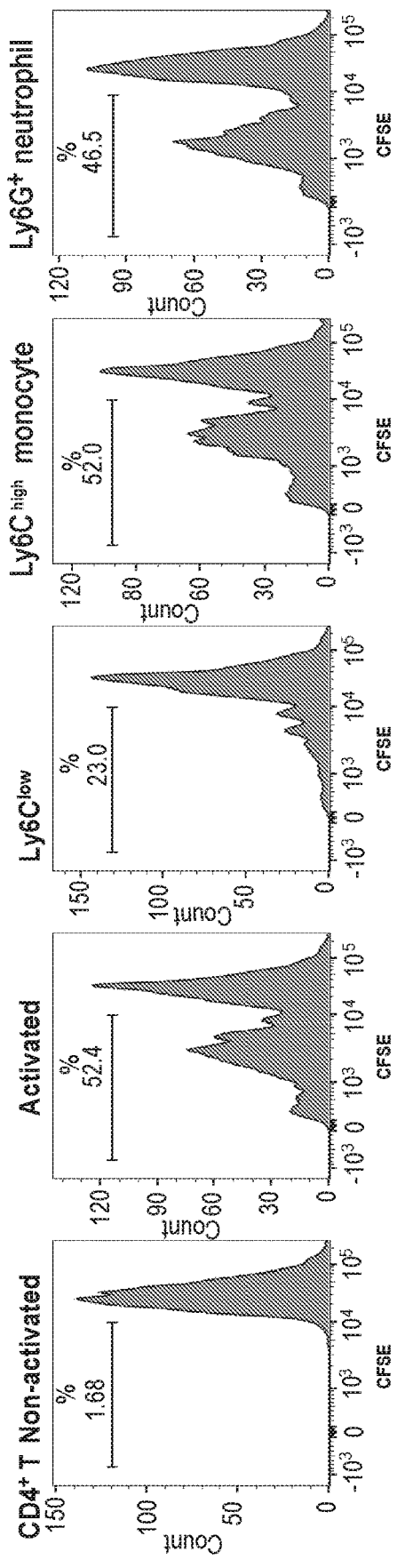

We next asked whether the tumor-infiltrated Ly6C$^{low}$ monocytes are able to modulate the tumor immune microenvironment. We found that expression levels of immunosuppressive cytokines (i.e., IL-10 and TGF-β1) were high in both Ly6C$^{low}$ monocytes and neutrophils in vitro (FIGS. 10B and 10C). In vivo, we measured higher levels of immunosuppressive cytokines in DC101-treated tumors, which are abundantly infiltrated by Ly6C$^{low}$ monocytes and neutrophils, than in the control. Further, immunostimulatory cytokines (i.e., TNF-α and IL-2) are downregulated upon DC101 treatment (FIGS. 6A and 10D). Flow cytometry analyses showed that DC101-treated tumors have significantly fewer effector CD4$^+$ and CD8$^+$ T cells compared to control (FIGS. 6B and 6C). Interestingly, lymphocytes in DC101-treated tumors expressed more PD-1, while lymphocytes in control treated tumors showed more Granzyme B expression (FIGS. 6D, 6E and 15A). Furthermore, tumors from DC101-treated Cx3cr1$^{-/-}$ mice, which showed delayed tumor growth (FIG. 5A), had higher numbers of CD4$^+$ and CD8$^+$ T cells—with more Granzyme B and less PD-1 expression—compared to DC101-treated wild-type animals (FIGS. 6B-6E and 15A). Importantly, the higher numbers of CD4$^+$ and CD8$^+$ T cells in Cx3cr1$^{-/-}$ mice was ablated when we adoptively transferred wild-type Ly6C$^{low}$ monocytes into Cx3cr1$^{-/-}$ mice (FIGS. 6B-6E). These data strongly support that mechanism that Ly6C$^{low}$ monocytes are directly involved in the regulation of adaptive immunity. These data suggest that DC101-treated tumors became skewed toward an immunosuppressive phenotype by infiltration of Ly6C$^{low}$ monocytes (FIGS. 6A-6E and 15).

Example 11. Ly6C$^{low}$ Monocytes and Neutrophils Produce IL-10 and Inhibit T Lymphocyte Proliferation Since Ly6Clow monocytes and neutrophils were more abundant in tumors with an immunosuppressive microenvironment, we further evaluated their capacity to suppress the proliferation of activated T lymphocytes.
Results An in vitro CFSE assay revealed that both Ly6C$^{low}$ monocytes and neutrophils inhibited CD8$^+$ T cell proliferation (FIG. 6F). Ly6C$^{low}$ monocytes also prevented the proliferation of CD4$^+$ T lymphocytes (FIG. 6G). Furthermore, motivated by the findings that Ly6C$^{low}$ monocytes and neutrophils express a high amount of IL-10 (FIGS. 10B and 10C), treatment with an anti-IL-10 neutralizing antibody prevented Ly6C$^{low}$ monocytes and neutrophils from inhibiting T cell proliferation (FIGS. 6F and 6G). Thus, we hypothesize that DC101-induced recruitment of Ly6C$^{low}$ monocytes and neutrophils producing IL-10 inhibits effector T cell activation, leading to a shift of the tumor microenvironment towards immunosuppression and thus to an attenuated immune response against the tumor.

Figure 7A:
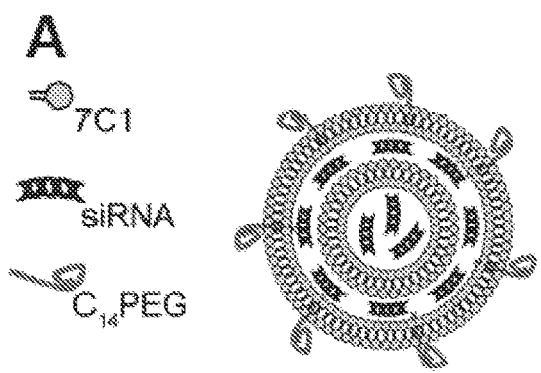
FIGS. 7A-7F. In vivo nanoparticle delivery of siCX3CL1 inhibits Ly6C$^{low}$ monocyte infiltration and enhances efficacy of anti-VEGFR2 therapy. (A) Schematic of 7C1 nanoparticle formulated with siRNA. (B) In vitro screening of siCX3CL1 candidate duplexes. Relative CX3CL1 expression level normalized to siLuc (Luciferase) control is plotted for candidate duplexes in 0.1 nM or 10 nM. Each siRNA was transfected twice and mRNA analysis was run in triplicates. Box bar plots indicate the best duplex selected for large-scale synthesis, and subsequent nanoparticle formulation. (C to F) C57BL/6 WT mice bearing orthotopically grown syngeneic SL4 CRCs were treated with either control rat IgG (C), 7C1-Axo-siCX3CL1 (7C1), DC101 (D), or 7C1-Axo-siCX3CL1+DC101 (7+D). (C) Relative CX3CL1 mRNA expression levels in endothelial cells isolated from SL4 tumors were determined by quantitative real-time PCR, normalized against GAPDH. Data are represented as mean±SEM. n=8/group. Comparison between groups was made using ANOVA with Holm-Sidak post-hoc test. *, p<0.05. (D) Western blot analysis of CX3CL1 protein expression in SL4 tumors treated as indicated. CX3CL1 protein levels were measured on day 12 after treatment. (E) Ly6C$^{low}$ monocytes in SL4 tumors treated as indicated. Ly6C$^{low}$ monocytes in tumor infiltrate were analyzed on day 12 after treatment by flow cytometry. n=8/group. The graphs depict the absolute number of cells per mg of tumor tissue. (F) Tumor volume of SL4 measured on day 12 after treatment. n=8/group. Data are represented as mean±SEM. Comparison between groups was made using ANOVA with Holm-Sidak post-hoc test. *, p<0.05. NS, non-significant.

Example 12. In Vivo Nanoparticle Delivery of siCX3CL1 Inhibits Ly6C$^{low}$ Monocyte Infiltration and Enhances Efficacy of Anti-VEGFR2 Therapy To determine whether CX3CL1 is an initiating molecule to DC101 tumor resistance, we developed a novel gene therapy method that can be potentially translated into an effective adjunct to anti-VEGF therapy in the clinic using nanoparticles (7C1) delivering small interfering RNA (siRNA) to target endothelial cells in vivo (60) (FIG. 7A).

Results

Figure 7B:
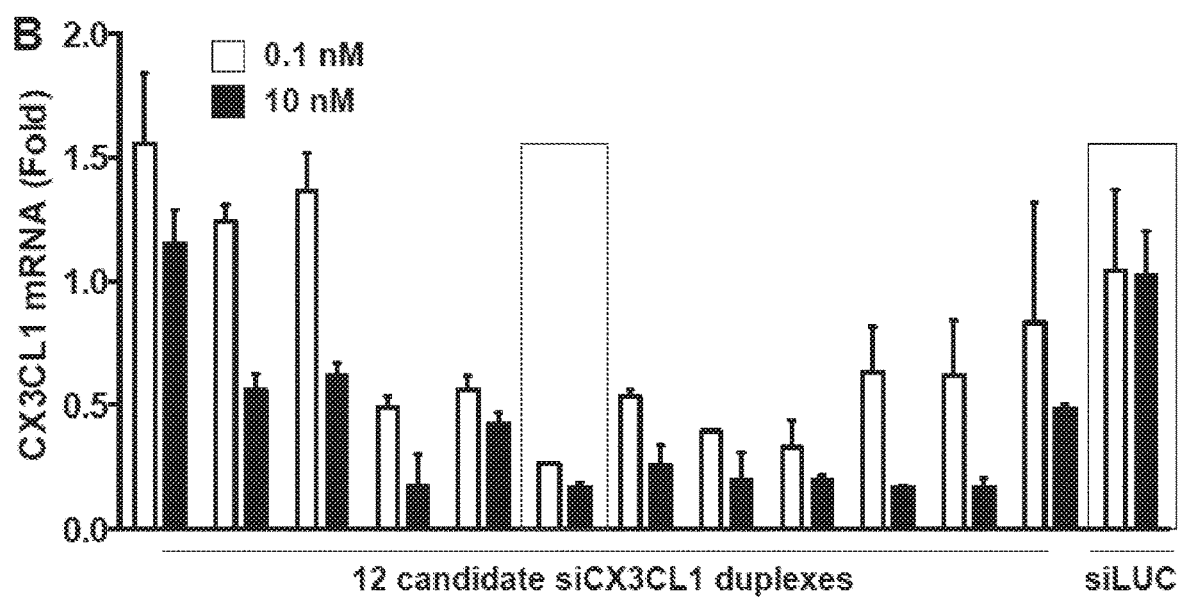
Figure 16A:
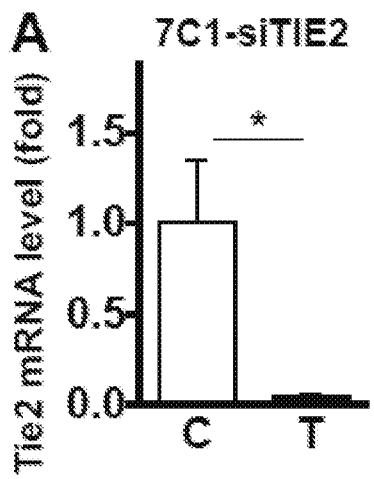
FIGS. 16A-16H. In vivo nanoparticle delivery of siCX3CL1 inhibits Ly6Clow monocyte infiltration and enhances efficacy of anti-VEGFR2 therapy. (A) C57BL/6 WT mice bearing orthotopically grown syngeneic SL4 CRCs were treated with either control vehicle or 7C1-siTie2. Relative Tie2 mRNA expression levels in endothelial cells isolated from SL4 tumors were determined on day 2 after treatment by quantitative real-time PCR, normalized against GAPDH. Data are represented as mean±SEM. n=5/group. Two-tailed t test. *, p<0.05. (B) The dose-response curve for the duplex that performed best in the In vitro screening of siCX3CL1 candidate duplexes which was selected for in vivo use (Axo-siCX3CL1, indicated by boxed bar plot in FIG. 7B). Relative CX3CL1 mRNA expression level in endothelial cells in vitro normalized to siLUC (Luciferase) control. Data are represented as mean±SEM. Data are representative of three independent experiments. (C) Comparison of the knock-down efficiency of our Axo-siCX3CL1 and another siRNA against CX3CL1 (siCX3CL1) from a recent publication (Moran et al., 2014). Data are represented as mean±SEM. Each siRNA was transfected twice and mRNA analysis was run in triplicates. Two-tailed t test. *, p<0.05 versus siCX3CL1. (D) Ly6Clow monocytes in SL4 tumors treated with either control rat IgG (C), 7C1-siLUC (LUC), DC101 (D), or 7C1-siLUC+DC101 (L+D). Ly6Clow monocytes in tumor infiltrate were analyzed on day 12 after treatment by flow cytometry Data are represented as mean±SEM. n=5/group. ANOVA with Holm-Sidak post-hoc test. *, p<0.05. NS, non-significant. (E) Tumor volume of SL4 measured on day 12 after treatment as indicated. n=5/group. Data are represented as mean±SEM. ANOVA with Holm-Sidak post-hoc test. *, p<0.05. NS, non-significant. (F) SL4 tumor growth. Tumor volume was measured using a high-frequency ultrasound imaging system for C57BL/6 mice bearing orthotopically grown syngeneic SL4 tumors treated as indicated. Data are represented as mean±SEM. n=8/group. (G and H) Ly6Chigh monocytes (G) and Ly6G+ neutrophils (H) in SL4 tumors treated with either control rat IgG (C), 7C1-Axo-siCX3CL1 (7C1), DC101 (D), or 7C1-Axo-siCX3CL1+DC101 (7+D). Ly6Chigh monocytes and Ly6G+ neutrophils in tumor infiltrate were analyzed on day 12 after treatment by flow cytometry. Data are represented as mean±SEM. n=8/group. ANOVA with Holm-Sidak post-hoc test. *, p<0.05. The graphs depict data for the absolute number of cells per mg of tumor tissue.
Figure 16B:
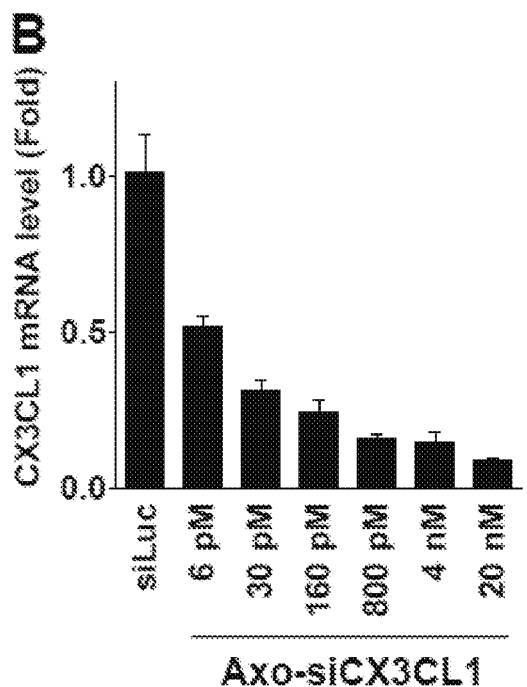
Figure 16C:
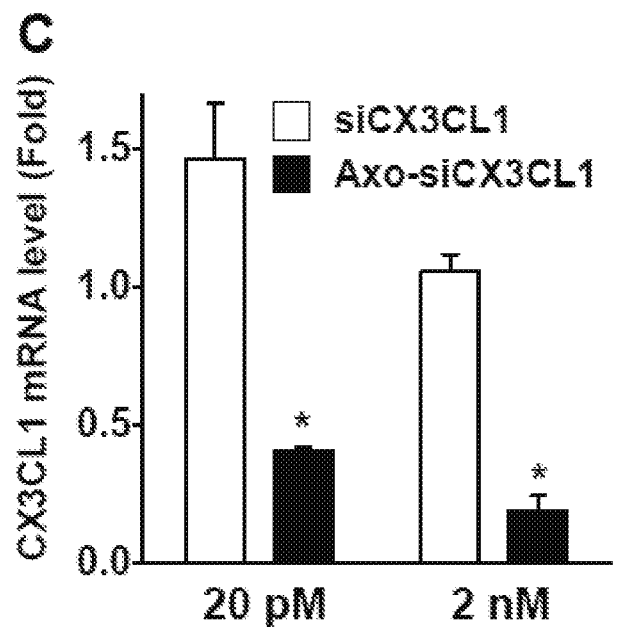

To validate whether the application of 7C1 nanoparticles was feasible for targeting endothelial cells in the tumor microenvironment, we first used nanoparticles formulated with siTIE2, which has already been proven to be efficacious in silencing Tie2 mRNA in several tissues (60). There was a significant decrease in Tie2 expression level after 7C1-siTIE2 treatment in CRCs (FIG. 16A). Next, we needed to harness specific siRNA sequences with superior knock-down efficacy against CX3CL1 (siCX3CL1), especially when applied in vivo. We performed in vitro screening with 12 candidate sequences—identified as lead siRNA molecules by in silico predictions of target specificity and activity (FIG. 7B). The best duplex with sequence 5'-gcuuGcGAGAGGGuuuAAAdTsdT-3' (sense; SEQ ID NO:15) and 5'-UUuAAACCCUCUCGcAAGCdTsdT-3' (anti-sense; SEQ ID NO:16) was selected for large-scale synthesis, and subsequent nanoparticle formulation (FIGS. 7B and 16B). Importantly, when we compared the knock-down efficiency of our siCX3CL1 (hereafter referred to as Axo-siCX3CL1) and another siRNA against CX3CL1 from a recent publication (61), there was a dramatic enhancement in silencing efficiency for Axo-siCX3CL1 (FIG. 16C).

Figure 7C:
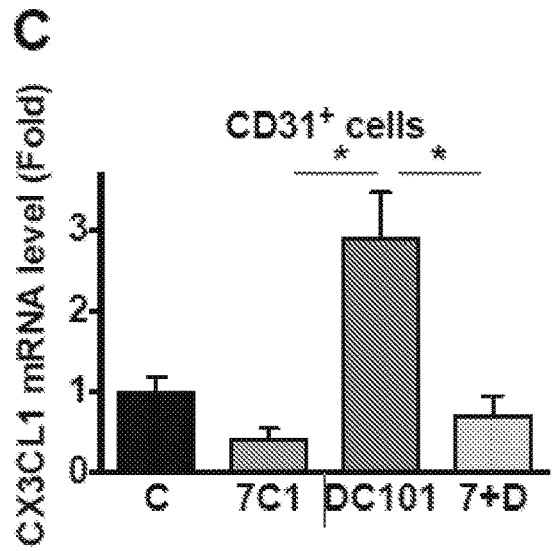
Figure 7D:
Figures 7E, 7F:
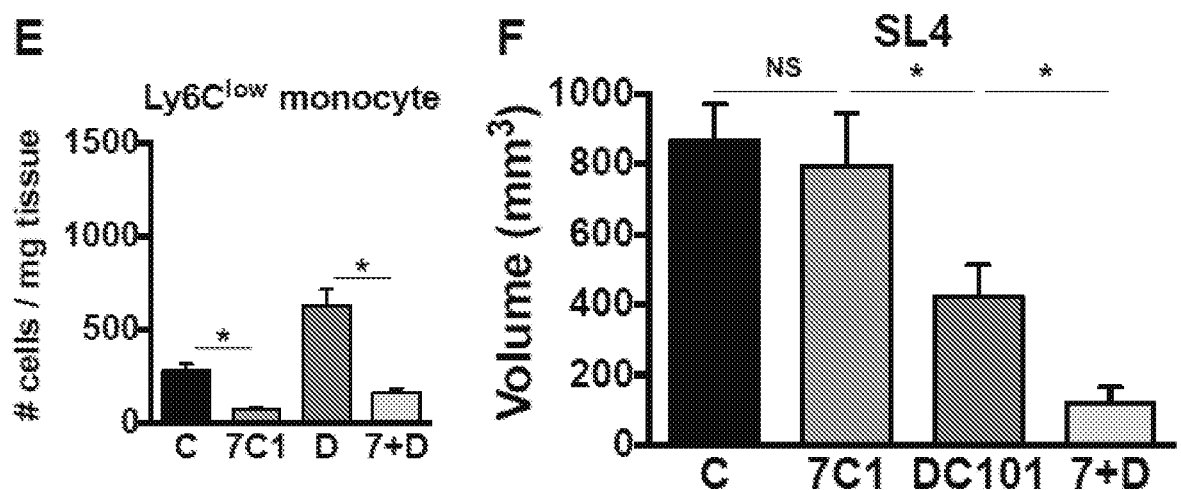
Figures 16D, 16E:
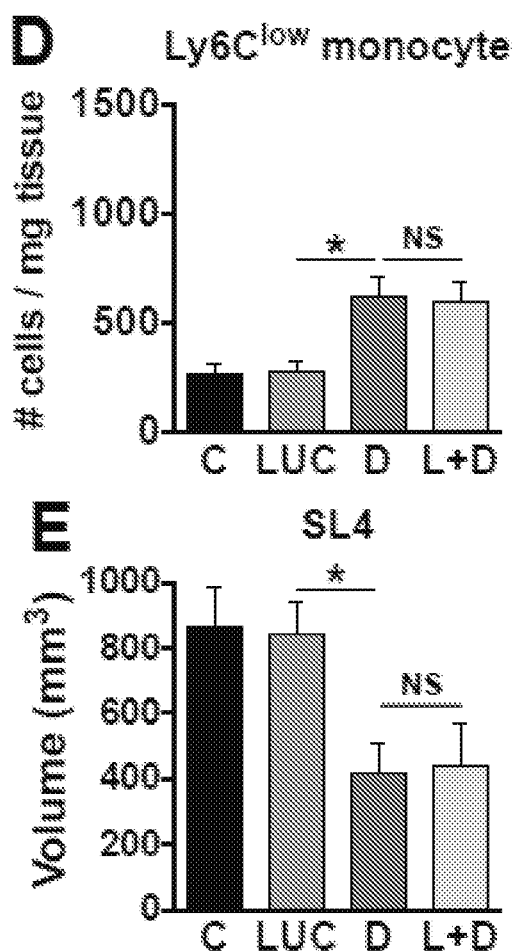
Figures 16F, 16G, 16H:
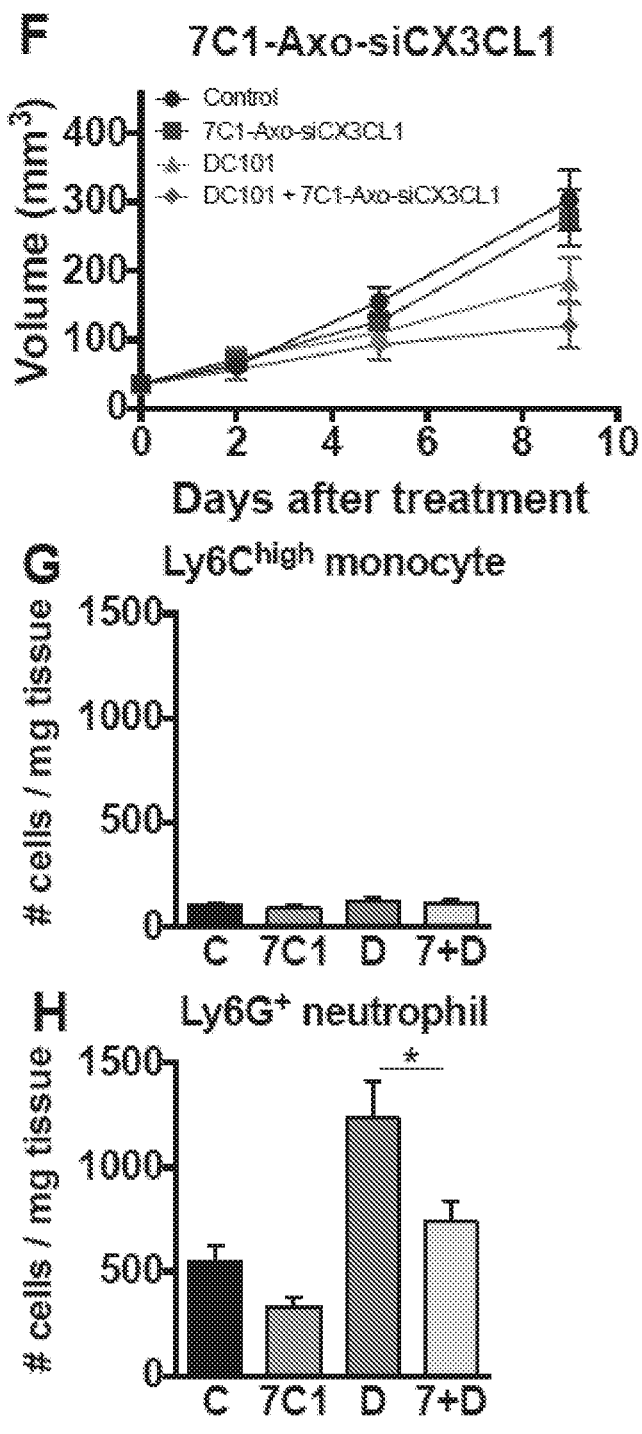

Next, we examined the effect of 7C1-Axo-siCX3CL1 in combination with DC101 in CRCs. Treatment with the negative control 7C1-siLUC (silencing Luciferase mRNA) did not change tumor growth or immune cell infiltration, and there was no difference between DC101 group and 7C1-siLUC+DC101 group (FIGS. 16D and 16E). We found that treating with 7C1-Axo-siCX3CL1 significantly enhanced the anti-tumor effect of anti-VEGFR2 therapy, even though there was negligible effect with 7C1-Axo-siCX3CL1 alone (FIGS. 7F and 16F). We confirmed that treatment of 7C1-Axo-siCX3CL1 markedly reduced DC101-induced upregulation of CX3CL1 in endothelial cells by measuring both mRNA and protein levels (FIGS. 7C and 7D). We also observed that in vivo knock-down of CX3CL1 mRNA significantly inhibited the infiltration of Ly6C$^{low}$ monocytes into DC101-treated tumors, and that subsequent tumor growth was delayed compared to control with only DC101 treatment (FIGS. 7E and 7F). Consistent with our experiments using Cx3cr1$^{-/-}$ mice, 7C1-Axo-siCX3CL1-treated tumors also showed subsequent decrease in Ly6G$^+$ neutrophils but did not alter Ly6C$^{high}$ monocytes (FIGS. 4E, 16G and 16H). These data confirm that CX3CL1 is an important chemoattractant for Ly6C$^{low}$ monocytes and contributes to the process of anti-VEGF therapy resistance.

REFERENCES

1. Jain R K. Antiangiogenesis Strategies Revisited: From Starving Tumors to Alleviating Hypoxia. *Cancer cell.* 2014; 26(5):605-22.
2. Carmeliet P, and Jain R K. Molecular mechanisms and clinical applications of angiogenesis. *Nature.* 2011; 473(7347):298-307.
3. Sitohy B, Nagy J A, and Dvorak H F. Anti-VEGF/VEGFR therapy for cancer: reassessing the target. *Cancer research.* 2012; 72(8):1909-14.
4. Weis S M, and Cheresh D A. Tumor angiogenesis: molecular pathways and therapeutic targets. *Nature medicine.* 2011; 17(11):1359-70.
5. Ferrara N, and Adamis A P. Ten years of anti-vascular endothelial growth factor therapy. *Nat Rev Drug Discov.* 2016; 15(6):385-403.
6. Chung A S, Wu X, Zhuang G, Ngu H, Kasman I, Zhang J, Vernes J M, Jiang Z, Meng Y G, Peale F V, et al. An interleukin-17-mediated paracrine network promotes tumor resistance to anti-angiogenic therapy. *Nature medicine.* 2013; 19(9):1114-23.
7. Hanahan D, and Coussens L M. Accessories to the crime: functions of cells recruited to the tumor microenvironment. *Cancer cell.* 2012; 21(3):309-22.
8. Casazza A, Laoui D, Wenes M, Rizzolio S, Bassani N, Mambretti M, Deschoemaeker S, Van Ginderachter J A, Tamagnone L, and Mazzone M. Impeding macrophage entry into hypoxic tumor areas by Sema3A/Nrp1 signaling blockade inhibits angiogenesis and restores antitumor immunity. *Cancer cell.* 2013; 24(6):695-709.
9. Rigamonti N, Kadioglu E, Keklikoglou I, Wyser Rmili C, Leow C C, and De Palma M. Role of angiopoietin-2 in adaptive tumor resistance to VEGF signaling blockade. *Cell reports.* 2014; 8(3):696-706.
10. Noy R, and Pollard J W. Tumor-associated macrophages: from mechanisms to therapy. *Immunity.* 2014; 41(1):49-61.
11. Kim C, Yang H, Fukushima Y, Saw P E, Lee J, Park J S, Park I, Jung J, Kataoka H, Lee D, et al. Vascular RhoJ is an effective and selective target for tumor angiogenesis and vascular disruption. *Cancer cell.* 2014; 25(1):102-17.
12. Franklin R A, Liao W, Sarkar A, Kim M V, Bivona M R, Liu K, Pamer E G, and Li M O. The cellular and molecular origin of tumor-associated macrophages. *Science.* 2014; 344(6186):921-5.
13. Rivera L, Pandika M, and Bergers G. Escape mechanisms from antiangiogenic therapy: an immune cell's perspective. *Advances in experimental medicine and biology.* 2014; 772(83-99.
14. Pardoll D M. The blockade of immune checkpoints in cancer immunotherapy. *Nature reviews Cancer.* 2012; 12(4):252-64.
15. Schmid M C, and Varner J A. Myeloid cells in tumor inflammation. *Vascular cell.* 2012; 4(1):14.
16. Finisguerra V, Di Conza G, Di Matteo M, Serneels J, Costa S, Thompson A A, Wauters E, Walmsley S, Prenen H, Granot Z, et al. MET is required for the recruitment of anti-tumoural neutrophils. *Nature.* 2015; 522(7556):349-53.
17. Buchbinder E I, and Hodi F S. Melanoma in 2015: Immune-checkpoint blockade—durable cancer control. *Nat Rev Clin Oncol.* 2016; 13(2):77-8.
18. Baumeister S H, Freeman G J, Dranoff G, and Sharpe A H. Coinhibitory Pathways in Immunotherapy for Cancer. *Annu Rev Immunol.* 2016; 34(539-73.
19. Topalian S L, Taube J M, Anders R A, and Pardoll D M. Mechanism-driven biomarkers to guide immune checkpoint blockade in cancer therapy. *Nature reviews Cancer.* 2016; 16(5):275-87.
20. D'Angelo S P, Larkin J, Sosman J A, Lebbe C, Brady B, Neyns B, Schmidt H, Hassel J C, Hodi F S, Lorigan P, et al. Efficacy and Safety of Nivolumab Alone or in Combination With Ipilimumab in Patients With Mucosal Melanoma: A Pooled Analysis. *Journal of clinical oncology.* 2017; 35(2):226-35.
21. Ratcliffe M J, Sharpe A, Midha A, Barker C, Scott M, Scorer P, Al-Masri H, Rebelatto M, and Walker J. Agreement between Programmed Cell Death Ligand-1 Diagnostic Assays across Multiple Protein Expression Cut-Offs in Non-Small Cell Lung Cancer. *Clinical cancer research.* 2017.
22. Kim J E, Patel M A, Mangraviti A, Kim E S, Theodros D, Velarde E, Liu A, Sankey E W, Tam A, Xu H, et al.

Combination Therapy with Anti-PD-1, Anti-TIM-3, and Focal Radiation Results in Regression of Murine Gliomas. *Clinical cancer research.* 2017; 23(1):124-36.

23. Shojaei F, Wu X, Malik A K, Zhong C, Baldwin M E, Schanz S, Fuh G, Gerber H P, and Ferrara N. Tumor refractoriness to anti-VEGF treatment is mediated by CD11b$^+$Gr1$^+$ myeloid cells. *Nature biotechnology.* 2007; 25(8):911-20.

24. Rivera L B, Meyronet D, Hervieu V, Frederick M J, Bergsland E, and Bergers G. Intratumoral myeloid cells regulate responsiveness and resistance to antiangiogenic therapy. *Cell reports.* 2015; 11(4):577-91.

25. Talmadge J E, and Gabrilovich D I. History of myeloid-derived suppressor cells. *Nature reviews Cancer.* 2013; 13(10):739-52.

26. Kumar V, Patel S, Tcyganov E, and Gabrilovich D I. The Nature of Myeloid-Derived Suppressor Cells in the Tumor Microenvironment. *Trends Immunol.* 2016; 37(3):208-20.

27. Bronte V, Brandau S, Chen S H, Colombo M P, Frey A B, Greten T F, Mandruzzato S, Murray P J, Ochoa A, Ostrand-Rosenberg S, et al. Recommendations for myeloid-derived suppressor cell nomenclature and characterization standards. *Nature communications.* 2016; 7(12150.

28. Peranzoni E, Zilio S, Mango I, Dolcetti L, Zanovello P, Mandruzzato S, and Bronte V. Myeloid-derived suppressor cell heterogeneity and subset definition. *Current opinion in immunology.* 2010; 22(2):238-44.

29. Movahedi K, Guilliams M, Van den Bossche J, Van den Bergh R, Gysemans C, Beschin A, De Baetselier P, and Van Ginderachter J A. Identification of discrete tumor-induced myeloid-derived suppressor cell subpopulations with distinct T cell-suppressive activity. *Blood.* 2008; 111(8):4233-44.

30. Youn J I, Nagaraj S, Collazo M, and Gabrilovich D I. Subsets of myeloid-derived suppressor cells in tumor-bearing mice. *Journal of immunology.* 2008; 181(8):5791-802.

31. Fong A M, Robinson L A, Steeber D A, Tedder T F, Yoshie O, Imai T, and Patel D D. Fractalkine and CX3CR1 mediate a novel mechanism of leukocyte capture, firm adhesion, and activation under physiologic flow. *The Journal of experimental medicine.* 1998; 188(8):1413-9.

32. Nahrendorf M, Swirski F K, Aikawa E, Stangenberg L, Wurdinger T, Figueiredo J L, Libby P, Weissleder R, and Pittet M J. The healing myocardium sequentially mobilizes two monocyte subsets with divergent and complementary functions. *The Journal of experimental medicine.* 2007; 204(12):3037-47.

33. Kim P, Chung E, Yamashita H, Hung K E, Mizoguchi A, Kucherlapati R, Fukumura D, Jain R K, and Yun S H. In vivo wide-area cellular imaging by side-view endomicroscopy. *Nature methods.* 2010; 7(4):303-5.

34. Tong R T, Boucher Y, Kozin S V, Winkler F, Hicklin D J, and Jain R K. Vascular normalization by vascular endothelial growth factor receptor 2 blockade induces a pressure gradient across the vasculature and improves drug penetration in tumors. *Cancer research.* 2004; 64(11):3731-6.

35. Highfill S L, Cui Y, Giles A J, Smith J P, Zhang H, Morse E, Kaplan R N, and Mackall C L. Disruption of CXCR2-mediated MDSC tumor trafficking enhances anti-PD1 efficacy. *Science translational medicine.* 2014; 6(237):237ra67.

36. Ali K, Soond D R, Pineiro R, Hagemann T, Pearce W, Lim E L, Bouabe H, Scudamore C L, Hancox T, Maecker H, et al. Inactivation of PI(3)K p110delta breaks regulatory T-cell-mediated immune tolerance to cancer. *Nature.* 2014; 510(7505):407-11.

37. Ries C H, Cannarile M A, Hoves S, Benz J, Wartha K, Runza V, Rey-Giraud F, Pradel L P, Feuerhake F, Klaman I, et al. Targeting tumor-associated macrophages with anti-CSF-1R antibody reveals a strategy for cancer therapy. *Cancer cell.* 2014; 25(6):846-59.

38. Stromnes I M, Brockenbrough J S, Izeradjene K, Carlson M A, Cuevas C, Simmons R M, Greenberg P D, and Hingorani S R. Targeted depletion of an MDSC subset unmasks pancreatic ductal adenocarcinoma to adaptive immunity. *Gut.* 2014; 63(11):1769-81.

39. Qin H, Lerman B, Sakamaki I, Wei G, Cha S C, Rao S S, Qian J, Hailemichael Y, Nurieva R, Dwyer K C, et al. Generation of a new therapeutic peptide that depletes myeloid-derived suppressor cells in tumor-bearing mice. *Nature medicine.* 2014; 20(6):676-81.

40. Katoh H, Wang D, Daikoku T, Sun H, Dey S K, and Dubois R N. CXCR2-expressing myeloid-derived suppressor cells are essential to promote colitis-associated tumorigenesis. *Cancer cell.* 2013; 24(5):631-44.

41. Kim K, Skora A D, Li Z, Liu Q, Tam A J, Blosser R L, Diaz L A, Jr., Papadopoulos N, Kinzler K W, Vogelstein B, et al. Eradication of metastatic mouse cancers resistant to immune checkpoint blockade by suppression of myeloid-derived cells. *Proceedings of the National Academy of Sciences of the United States of America.* 2014; 111(32):11774-9.

42. Di Mitri D, Toso A, Chen J J, Sarti M, Pinton S, Jost T R, D'Antuono R, Montani E, Garcia-Escudero R, Guccini I, et al. Tumour-infiltrating Gr-1+ myeloid cells antagonize senescence in cancer. *Nature.* 2014; 515(7525):134-7.

43. Damuzzo V, Pinton L, Desantis G, Solito S, Mango I, Bronte V, and Mandruzzato S. Complexity and challenges in defining myeloid-derived suppressor cells. *Cytometry Part B, Clinical cytometry.* 2014.

44. Gabrilovich D I, Ostrand-Rosenberg S, and Bronte V. Coordinated regulation of myeloid cells by tumours. *Nature reviews Immunology.* 2012; 12(4):253-68.

45. Ritsma L, Steller E J, Ellenbroek S I, Kranenburg O, Borel Rinkes I H, and van Rheenen J. Surgical implantation of an abdominal imaging window for intravital microscopy. *Nature protocols.* 2013; 8(3):583-94.

46. Palmer G M, Fontanella A N, Shan S, Hanna G, Zhang G, Fraser C L, and Dewhirst M W. In vivo optical molecular imaging and analysis in mice using dorsal window chamber models applied to hypoxia, vasculature and fluorescent reporters. *Nature protocols.* 2011; 6(9):1355-66.

47. Kirkpatrick N D, Chung E, Cook D C, Han X, Gruionu G, Liao S, Munn L L, Padera T P, Fukumura D, and Jain R K. Video-rate resonant scanning multiphoton microscopy: An emerging technique for intravital imaging of the tumor microenvironment. *Intravital.* 2012; 1(1).

48. Auffray C, Fogg D, Garfa M, Elain G, Join-Lambert O, Kayal S, Sarnacki S, Cumano A, Lauvau G, and Geissmann F. Monitoring of blood vessels and tissues by a population of monocytes with patrolling behavior. *Science.* 2007; 317(5838):666-70.

49. Carlin L M, Stamatiades E G, Auffray C, Hanna R N, Glover L, Vizcay-Barrena G, Hedrick C C, Cook H T, Diebold S, and Geissmann F. Nr4a1-dependent Ly6C (low) monocytes monitor endothelial cells and orchestrate their disposal. *Cell.* 2013; 153(2):362-75.
50. Saja M F, Baudino L, Jackson W D, Cook H T, Malik T H, Fossati-Jimack L, Ruseva M, Pickering M C, Woollard K J, and Botto M. Triglyceride-Rich Lipoproteins Modulate the Distribution and Extravasation of Ly6C/Gr1 (low) Monocytes. *Cell reports.* 2015; 12(11):1802-15.
51. Jung S, Aliberti J, Graemmel P, Sunshine M J, Kreutzberg G W, Sher A, and Littman D R. Analysis of fractalkine receptor CX(3)CR1 function by targeted deletion and green fluorescent protein reporter gene insertion. *Molecular and cellular biology.* 2000; 20(11):4106-14.
52. Jung K, Kim P, Leuschner F, Gorbatov R, Kim J K, Ueno T, Nahrendorf M, and Yun S H. Endoscopic time-lapse imaging of immune cells in infarcted mouse hearts. *Circulation research.* 2013; 112(6):891-9.
53. Haskell C A, Cleary M D, and Charo I F. Molecular uncoupling of fractalkine-mediated cell adhesion and signal transduction. Rapid flow arrest of CX3CR1-expressing cells is independent of G-protein activation. *The Journal of biological chemistry.* 1999; 274(15):10053-8.
54. Landsman L, Bar-On L, Zernecke A, Kim K W, Krauthgamer R, Shagdarsuren E, Lira S A, Weissman I L, Weber C, and Jung S. CX3CR1 is required for monocyte homeostasis and atherogenesis by promoting cell survival. *Blood.* 2009; 113(4):963-72.
55. Kim K W, Vallon-Eberhard A, Zigmond E, Farache J, Shezen E, Shakhar G, Ludwig A, Lira S A, and Jung S. In vivo structure/function and expression analysis of the CX3C chemokine fractalkine. *Blood.* 2011; 118(22): e156-67.
56. Willett C G, Duda D G, di Tomaso E, Boucher Y, Ancukiewicz M, Sahani D V, Landenranta J, Chung D C, Fischman A J, Lauwers G Y, et al. Efficacy, safety, and biomarkers of neoadjuvant bevacizumab, radiation therapy, and fluorouracil in rectal cancer: a multidisciplinary phase II study. *Journal of clinical oncology.* 2009; 27(18):3020-6.
57. Xu L, Duda D G, di Tomaso E, Ancukiewicz M, Chung D C, Lauwers G Y, Samuel R, Shellito P, Czito B G, Lin P C, et al. Direct evidence that bevacizumab, an anti-VEGF antibody, up-regulates SDFlalpha, CXCR4, CXCL6, and neuropilin 1 in tumors from patients with rectal cancer. *Cancer research.* 2009; 69(20):7905-10.
58. Geissmann F, Jung S, and Littman D R. Blood monocytes consist of two principal subsets with distinct migratory properties. *Immunity.* 2003; 19(1):71-82.
59. Qian B Z, Li J, Zhang H, Kitamura T, Zhang J, Campion L R, Kaiser E A, Snyder L A, and Pollard J W. CCL2 recruits inflammatory monocytes to facilitate breast-tumour metastasis. *Nature.* 2011; 475(7355):222-5.
60. Dahlman J E, Barnes C, Khan O F, Thiriot A, Jhunjunwala S, Shaw T E, Xing Y, Sager H B, Sahay G, Speciner L, et al. In vivo endothelial siRNA delivery using polymeric nanoparticles with low molecular weight. *Nat Nanotechnol.* 2014; 9(8):648-55.
61. Moran J, Anhe G F, Nascimento L F, de Moura R F, Razolli D, Solon C, Guadagnini D, Souza G, Mattos A H, Tobar N, et al. Fractalkine (CX3CL1) is involved in the early activation of hypothalamic inflammation in experimental obesity. *Diabetes.* 2014; 63(11):3770-84.
62. Yang L, Huang J, Ren X, Gorska A E, Chytil A, Aakre M, Carbone D P, Matrisian L M, Richmond A, Lin P C, et al. Abrogation of TGF beta signaling in mammary carcinomas recruits Gr-1+CD11b+ myeloid cells that promote metastasis. *Cancer cell.* 2008; 13(1):23-35.
63. Huang Y, Yuan J, Righi E, Kamoun W S, Ancukiewicz M, Nezivar J, Santosuosso M, Martin J D, Martin M R, Vianello F, et al. Vascular normalizing doses of antiangiogenic treatment reprogram the immunosuppressive tumor microenvironment and enhance immunotherapy. *Proceedings of the National Academy of Sciences of the United States of America.* 2012; 109(43):17561-6.
64. Pernot S, Terme M, Voron T, Colussi O, Marcheteau E, Tartour E, and Taieb J. Colorectal cancer and immunity: what we know and perspectives. *World J Gastroenterol.* 2014; 20(14):3738-50.
65. Rahbari N N, Kedrin D, Incio J, Liu H, Ho W W, Nia H T, Edrich C M, Jung K, Daubriac J, Chen I, et al. Anti-VEGF therapy induces ECM remodeling and mechanical barriers to therapy in colorectal cancer liver metastases. *Science translational medicine.* 2016; 8(360): 360ra135.
66. Hanna R N, Cekic C, Sag D, Tacke R, Thomas G D, Nowyhed H, Herrley E, Rasquinha N, McArdle S, Wu R, et al. Patrolling monocytes control tumor metastasis to the lung. *Science.* 2015; 350(6263):985-90.
67. Morimoto-Tomita M, Ohashi Y, Matsubara A, Tsuiji M, and Irimura T. Mouse colon carcinoma cells established for high incidence of experimental hepatic metastasis exhibit accelerated and anchorage-independent growth. *Clinical & experimental metastasis.* 2005; 22(6):513-21.
68. Zhang Y, Davis C, Ryan J, Janney C, and Pena M M. Development and characterization of a reliable mouse model of colorectal cancer metastasis to the liver. *Clinical & experimental metastasis.* 2013; 30(7):903-18.
69. Chung E, Yamashita H, Au P, Tannous B A, Fukumura D, and Jain R K. Secreted Gaussia luciferase as a biomarker for monitoring tumor progression and treatment response of systemic metastases. *PloS one.* 2009; 4(12): e8316.
70. Tannous B A. Gaussia luciferase reporter assay for monitoring biological processes in culture and in vivo. *Nature protocols.* 2009; 4(4):582-91.
71. Hu Y L, DeLay M, Jahangiri A, Molinaro A M, Rose S D, Carbonell W S, Aghi M K. Hypoxia-induced autophagy promotes tumor cell survival and adaptation to antiangiogenic treatment in glioblastoma. *Cancer Research.* 2012; 72(7):1773-83.
72. Milosevic M F, Townsley C A, Chaudary N, Clarke B, Pintilie M, Fan S, Glicksman R, Haider M, Kim S, MacKay H, Yeung I, Hill R P, Fyles A, Oza A M. Sorafenib Increases Tumor Hypoxia in Cervical Cancer Patients Treated With Radiation Therapy: Results of a Phase 1 Clinical Study. *Int J Radiat Oncol Biol Phys.* 2016; 94(1):111-7.
73. Chiu D K, Xu I M, Lai R K, Tse A P, Wei L L, Koh H Y, Li L L, Lee D, Lo R C, Wong C M, Ng 10, Wong C C. Hypoxia induces myeloid-derived suppressor cell recruitment to hepatocellular carcinoma through chemokine (C-C motif) ligand 26. *Hepatology.* 2016; 64(3):797-813.
74. Rivera L B and Bergers G. Intertwined regulation of angiogenesis and immunity by myeloid cells. *Trends in Immunology.* 2015; 36(4):240-9.
75. Willett C G, Duda D G, di Tomaso E, Boucher Y, Ancukiewicz M, Sahani D V, Landenranta J, Chung D C, Fischman A J, Lauwers G Y, et al. Efficacy, safety, and biomarkers of neoadjuvant bevacizumab, radiation therapy, and fluorouracil in rectal cancer: a multidisciplinary phase II study. Journal of clinical oncology: official journal of the American Society of Clinical Oncology. 2009; 27(18):3020-6.

76. Xu L, Duda D G, di Tomaso E, Ancukiewicz M, Chung D C, Lauwers G Y, Samuel R, Shellito P, Czito B G, Lin P C, et al. Direct evidence that bevacizumab, an anti-VEGF antibody, up-regulates SDFlalpha, CXCR4, CXCL6, and neuropilin 1 in tumors from patients with rectal cancer. Cancer research. 2009; 69(20):7905-10.
77. Huang Y, Yuan J, Righi E, Kamoun W S, Ancukiewicz M, Nezivar J, Santosuosso M, Martin J D, Martin M R, Vianello F, et al. Vascular normalizing doses of antiangiogenic treatment reprogram the immunosuppressive tumor microenvironment and enhance immunotherapy. Proceedings of the National Academy of Sciences of the United States of America. 2012; 109(43):17561-6.
78. Kirkpatrick N D, Chung E, Cook D C, Han X, Gruionu G, Liao S, Munn L L, Padera T P, Fukumura D, and Jain R K. Video-rate resonant scanning multiphoton microscopy: An emerging technique for intravital imaging of the tumor microenvironment. Intravital. 2012; 1(1).
79. Dahlman J E, Barnes C, Khan O F, Thiriot A, Jhunjunwala S, Shaw T E, Xing Y, Sager H B, Sahay G, Speciner L, et al. In vivo endothelial siRNA delivery using polymeric nanoparticles with low molecular weight. Nat Nanotechnol. 2014; 9(8):648-55.
80. Chen D, Love K T, Chen Y, Eltoukhy A A, Kastrup C, Sahay G, Jeon A, Dong Y, Whitehead K A, and Anderson D G. Rapid discovery of potent siRNA-containing lipid nanoparticles enabled by controlled microfluidic formulation. J Am Chem Soc. 2012; 134(16):6948-51.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising one or more inhibitory nucleic acids that comprises a siRNA or a locked nucleic acid (LNA) that bind to and reduce expression or activity of C-X3-C chemokine ligand 1 (CX3CL1), encapsulated within or linked to an endothelial cell delivery vehicle that comprises a lipid nanoparticle that comprises 7C1 nanoparticles, SAINT-C 18 lipoplexes, PEGylated SAINT-C18 lipoplexes, polyethyleneimine (PEI) PEGylated with an Arg-Gly-Asp (RGD) peptide (RGD-PEG-PEI) (RPP-nanoplexes), or Polycation Liposome-encapsulated Calcium Phosphate nanoparticles (PLCP).

2. The composition of claim 1, wherein the siRNA is chemically modified to have increased siRNA half-life.

3. The composition of claim 1, wherein the one or more inhibitory nucleic acids are linked to a cell-penetrating peptide.

4. A pharmaceutical composition comprising the composition of claim 1, and a pharmaceutically acceptable carrier.

5. The pharmaceutical composition of claim 4, further comprising an anti-angiogenic agent.

6. The pharmaceutical composition of claim 5, wherein the anti-angiogenic agent is a VEGF inhibitor.

7. A method of treating a solid cancer, the method comprising administering to a subject in need thereof a therapeutically effective amount of the pharmaceutical composition of claim 4.

8. The method of claim 7, further comprising administering a therapeutically effective amount of an anti-angiogenic agent to the subject.

9. The method of claim 7, wherein the subject has been treated with an anti-angiogenic agent prior to administration of the pharmaceutical composition of claim 4.

10. The method of claim 8, wherein the cancer is resistant to the anti-angiogenic.

11. The method of claim 8, wherein the anti-angiogenic agent is a VEGF inhibitor.

12. The method of claim 8, wherein the anti-angiogenic agent is administered prior to or concurrently with the pharmaceutical composition.

13. The method of claim 7, wherein the cancer is a carcinoma.

14. The method of claim 13, wherein the carcinoma is a colorectal, breast, or lung carcinoma.

15. The method of claim 7, wherein the cancer is colorectal carcinoma.

16. The composition of claim 1, wherein the endothelial cell delivery vehicle comprises 7C1 nanoparticles.

\* \* \* \* \*